United States Patent
Ivachtchenko et al.

(10) Patent No.: US 9,655,886 B2
(45) Date of Patent: May 23, 2017

(54) SUBSTITUTED 2,3,4,5-TETRAHYDRO-1H-PYRIDO[4,3-B]INDOLES, METHODS FOR USE THEREOF

(71) Applicants: Alexandre Vasilievich Ivachtchenko, Encinitas, CA (US); Andrey Alexandrovich Ivashchenko, Moscow (RU); Nikolay Filippovich Savchuk, Moscow (RU)

(72) Inventors: Alexandre Vasilievich Ivachtchenko, Encinitas, CA (US); Andrey Alexandrovich Ivashchenko, Moscow (RU); Nikolay Filippovich Savchuk, Moscow (RU)

( * ) Notice: Subject to any disclaimer, the term of this patent is extended or adjusted under 35 U.S.C. 154(b) by 0 days.

(21) Appl. No.: 14/791,280

(22) Filed: Jul. 3, 2015

(65) Prior Publication Data

US 2017/0000773 A1    Jan. 5, 2017

(51) Int. Cl.
  A61K 31/44    (2006.01)
  A61K 31/437   (2006.01)
  C07D 471/04   (2006.01)
  A61K 31/444   (2006.01)

(52) U.S. Cl.
  CPC ......... *A61K 31/437* (2013.01); *A61K 31/444* (2013.01); *C07D 471/04* (2013.01)

(58) Field of Classification Search
  CPC .................................................. A61K 31/437
  USPC ...................................................... 514/292
  See application file for complete search history.

(56) References Cited

U.S. PATENT DOCUMENTS 7,071,206 B2 *  7/2006  Zefirov ............... A61K 49/006
                                                       514/292

FOREIGN PATENT DOCUMENTS

WO        2005055951     *  6/2005

OTHER PUBLICATIONS

Jensen Klaus, 1960, pp. 293-305, The effect of antiserotonin (cyproheptadine) and antihistamine on cutaneous allergy.*
Okun I et al. From Anti-Allergic to Anti-Alzheimer's: Molecular Pharmacology of Dimebon, 2010.*

* cited by examiner

*Primary Examiner* — Raymond Henley, III

(57)    ABSTRACT

The present invention relates to a method of antagonizing a $5\text{-}HT_6$ serotonin receptor, comprising administering to the cell a compound of formula 1.2, or a pharmaceutically acceptable salt thereof,

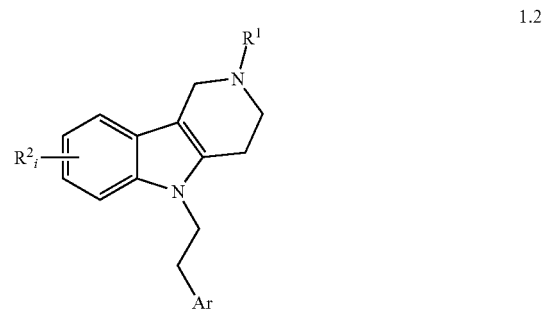

1.2 wherein: $R^1$ is a $C_1\text{-}C_5$ alkyl;
$R^2_i$ is independently hydrogen, halogen, a $C_1\text{-}C_3$ alkyl, $CF_3$, $OCF_3$ or $OCH_3$;
i is 1, 2, 3 or 4;
Ar is an unsubstituted phenyl or a substituted phenyl substituted with halogen, $C_1\text{-}C_6$ alkyl, $C_1\text{-}C_6$ alkoxy, substituted amino group or trifluoromethyl; or Ar is a substituted or unsubstituted 6-membered aromatic heterocycle with one or two nitrogen atoms in the heterocycle.

Figure 1:
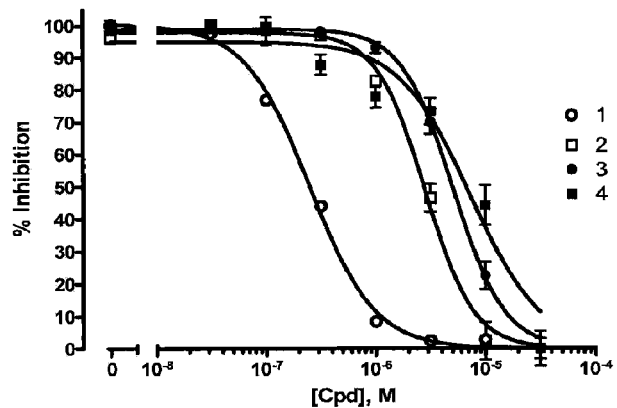

The invention also relates to pharmaceutical compositions and method for treating a cognitive disorder or neurodegenerative disease in a subject in need thereof comprising administering an effective dose to the subject of a compound of formula 1.2 according to claim 1, or a pharmaceutically acceptable salt thereof.

8 Claims, 11 Drawing Sheets

SUBSTITUTED 2,3,4,5-TETRAHYDRO-1H-PYRIDO[4,3-B]INDOLES, METHODS FOR USE THEREOF

CROSS REFERENCE TO RELATED APPLICATIONS

This application is a Division of application Ser. No. 13/844,825, filed Mar. 16, 2013, which is a Division of application Ser. No. 12/594,453, filed Oct. 2, 2009 which claims benefit of priority to the International application PCT/RU2008/000196 filed Apr. 1, 2008, which claims benefit of foreign priority to the Russian Federation application RU 2007112666 of May 4, 2007. The priority applications are hereby incorporated by reference in their entirety.

FIELD OF THE INVENTION

The invention relates to the novel chemical compounds, methods for their preparation and use as antagonists of $5\text{-HT}_6$ receptors, simultaneously regulating homeostasis of calcium ions in cells. More specifically, the invention relates to the novel annelated azaheterocycles—2,3,4,5-tetrahydro-1H-pyrido[4,3-b]indoles, optical and geometrical isomers, racemic mixtures, pharmaceutically acceptable salts and/or hydrates thereof, to methods for their preparation, to pharmaceutical compositions, including these compounds as active substances, and to methods of treatment and profylaxis of various diseases, among them neurodegenerative diseases such as schizophrenia or Alzheimer's disease, concerned with the elevated penetration of calcium ions into nerve cells, that initiates the whole number of pathological metabolic processes, finally inducing death of neurones [D. W. Choi, *Neurone*, 1988; 1:623-634].

PRIOR ART

The origin of pharmacological action of 2,3,4,5-tetrahydro-1H-pyrido[4,3-b]indoles lays in their ability to reduce effectively the cytozolic concentration of calcium ions, when intracellular concentration of calcium ions has become elevated as a result of various pathological processes. Besides, these compounds are effective antagonists of $5\text{-HT}_6$ serotonin receptors, playing an important role in treatment diseases associated with central nervous system (CNS), such as Alzheimer's disease, Hungtinton's disease, schizophrenia or other neurodegenerative diseases and obesity.

Maintenance of low concentration of calcium ions is extremely important for normal cell functioning, because the prolonged enhancement of $Ca^{+2}$ level in cytozole leads to apoptosis. Such mechanism of apoptpsis is a characteristic feature of all neurodegenerative diseases, that is why searching for farmacological remedies preventing elevated penetration of $Ca^{+2}$ ions into neurones is one of the most important direction of neuroprotector development [Kiewert C., Hartmann J., Stoll J., Thekkumkara T. J., Van der Schyf C. J., Klein J. NGP1-01 is a Brain-permeable Dual Blocker of Neuronal Voltage- and Ligand-operated Calcium Channels. *Neurochem Res.* 2006 May 3]. Cytozolic $Ca^{+2}$ concentration in eucariotic cells is regulated by transmembrane transport and by cytoplasmic calcium binding [Sayer R. J. Intracellular Ca2+ handling. *Adv Exp Med Biol.* 2002; 513:183-96].

Obviously, the various proteins supporting calcium homeostasis in cytoplasm play an extraordinary role in patogenesis of such neuralgic disorders as hypoxia-ischemia, hypoglycemia, convulsive conditions, cerebral traumas and also chronic neurodegenerative diseases (including Alzheimer's disease, Hungtinton's chorea, lathyrism, lateral amyotrophic sclerosis). [J. W. McDonald, M. V. Johnston—*Brain Res. Rev.*, 1990; 15:41-70; Stys P. K. General mechanisms of axonal damage and its prevention. *J Neurol Sci.* 2005; 233(1-2):3-13]. The possibility of pool regulation of intracellular $Ca^{+2}$ accounts for great pharmacological role of selective blockers/activators of various potential dependent calcium channels (for example, T-, L-, N-, P-, Q- and R-channels) and specific antagonist/modulator of ligand-gated channels (for example, NMDA-, AMPA-, nAChR-, P2X-receptors) [Barry P. H., Lynch J. W. Ligand-gated channels. IEEE Trans Nanobioscience. 2005; 4(1):70-80]. At present a great number of such calcium transport effectors are offered as highly effective medicines. For example, calcium antagonists—is a group of drugs the common feature of which is the ability to reversible blocking of calcium flow through potential-dependent calcium channels. Judging by their chemical structure these drugs could be devided into two large subgroups—dihydropyridines (Nifedipine, Amlodipine, Felodipine and others), in the properties of which the effect of peripheric vasodilatation is predominated, and non-dihydropyridines (Verapamil and Diltiazem), the main properties of which is negative chrono- and inotropic action and the ability to reduce atrioventricular conductibility as well [Sica D. A. Pharmacotherapy review: calcium channel blockers. J Clin Hypertens (Greenwich). 2006; 8(1):53-6]. An example of a drug blocking an excessive penetration of calcium ions into neurones through ligand-gated channels (NMDA) is Memantine, widely used at present in the treatment of Alzheimer's disease [Rogawski M. A., Wenk G. L. The neuropharmacological basis for the use of memantine in the treatment of Alzheimer's disease. *CNS Drug Rev.* 2003; 9(3):275-308]. Nearly all mentioned drugs prevent the penetration of calcium ions into cells, however, calcium homeostsis modulators capable for effective reducing of calcium cytosolic concentration which became elevated as a result of some pathologic processes have not been known yet Use of effective and selective antagonists of $5\text{-HT}_6$ receptors for treatment diseases associated with CNS, in particular, schizophrenia, Alzheimer's disease and other neurodegenerative diseases is a perspective direction for development of novel medicines [Holenz J., Pauwels P. J., Diaz J. L., Merce R., Codony X., Buschmann H. Medicinal chemistry strategies to $5\text{-HT}_6$ receptor ligands as potential cognitive enhancers and antiobesity agents. *Drug Disc. Today.* 2006; 11:283-299]. At mammals these receptors are found exclusively in the central nervous system (CNS), mainly, in the parts of brain responsible for training and memory [Ge'rard C., Martres M.-P., Lefe'vre K., Miquel M.-C., Verge' D., Lanfumey L., Doucet E., Hamon M., El Mestikawy S. Immuno-localisation of serotonin $5\text{-HT}_6$ receptor-like material in the rat central nervous system. *Brain Research.* 1997; 746:207-219]. Moreover, it was shown [Dawson L. A., Nguyen H. Q., Li P. The 5-HT(6) receptor antagonist SB-271046 selectively enhances excitatory neurotransmission in the rat frontal cortex and hippocampus. *Neuropsychopharmacology.* 2001; 25:662-668], that 5-HT$_6$ receptors are modulators of several neuromediator systems, including cholinergic, noradrenergic, glutamatergic and dopaminergic. Bearing in mind the fundamental role of these systems in normal cognitive processes and also their disfunction at neurodegeneration, it becomes obvious an exclusive role of 5-NT$_6$ receptors in the finctioning of normal or "pathological" memory. In many current publication it was shown, that blocking of 5-HT$_6$ receptors leads to considerable enhancement of memory consolidation in various animal models of training—memorising—reproduction [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100. Riemer C., Borroni E., Levet-Trafit B., Martin J. R., Poli S., Porter R. H., Bos M. Influence of the 5-HT6 receptor on acetylcholine release in the cortex: pharmacological characterization of 4-(2-bromo-6-pyrrolidin-1-ylpyridine-4-sulfonyl)phenylamine, a potent and selective 5-HT$_6$ receptor antagonist. *J. Med. Chem.* 2003; 46:1273-1276. King M. V., Woolley M. L., Topham I. A., Sleight A. J., Marsden C. A., Fone K. C. 5-HT6 receptor antagonists reverse delay-dependent deficits in novel object discrimination by enhancing consolidation an effect sensitive to NMDA receptor antagonism. Neuropharmacology 2004; 47:195-204]. It was also shown significant improvement of cognitive functions of aged rats in a model of water Morrison's labyrinth under the action of 5-HT$_6$ receptor antagonists [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100]. Recently, not merely the more fundamental understanding of 5-HT$_6$ receptors role in cognitive processes was achieved, but also more unambiguous conception concerning pharmacophoric possibilities of their antagonists [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299]. It resulted in creation of high-affinity selective ligandes ("molecular tools"), and then clinical candidates. Now the whole number of 5-HT$_6$ receptor antagonists are at various stages of clinical tests as drug candidates for treatment of Alzheimer's disease, Hungtinton's disease, schizophrenia (antipsychotics) and other neurodegenerative and cognitive diseases (Table 1) [http://integrity.prous.com].

TABLE 1

Antagonists of 5-HT$_6$ receptors as drug candidates.

| Drug | Clinical phase of testing | Sponsor | Therapeutic group |
|---|---|---|---|
| Dimebon ™ | Phase III | Medivation (USA) | Treatment of Alzheimer's disease |
| SGS-518 | Phase II | Lilly, Saegis | Treatment of cognitive diseases |
| SB-742457 | Phase II | GlaxoSmithKline | Treatment of Alzheimer's disease; Antipsychotic |

TABLE 1-continued

Antagonists of 5-HT$_6$ receptors as drug candidates.

| Drug | Clinical phase of testing | Sponsor | Therapeutic group |
|---|---|---|---|
| Dimebon* | Phase I/IIa | Medivation (USA) | Treatment of Huntington's disease |
| Dimebon* | Phase II | (Russia) | Antipsychotic |
| PRX-07034 | Phase I | Epix Pharm. | Treatment of overweight; Antipsychotic; Treatment of cognitive diseases |
| SB-737050A | Phase II | GlaxoSmithKline | Antipsychotic |
| BVT-74316 | Phase I | Biovitrum | Treatment of overweight |
| SAM-315 | Phase I | Wyeth Pharm. | Treatment of Alzheimer's disease |
| SYN-114 | Phase I | Roche, Synosis Ther. | Treatment of cognitive diseases |
| BGC-20-761 | Preclinical phase | BTG (London) | Antipsychotic; Treatment of cognitive diseases |
| FMPO | Preclinical phase | Lilly | Antipsychotic |
| Dimebon ™ | Preclinical phase | (Russia) | Treatment of insult |

*during this investigation the authors discovered for the first time that Dimebon is 5-HT$_6$ receptor antagonist and simultaneously regulates homeostasis of calcium ions in cells.

Another attractive property of antagonists of 5-HT$_6$ receptors is their ability to suppress appetite that can lead to creation principally new remedies for treatment of overweight and obesity on their bases [Vicker S. P., Dourish C. T. Serotonin receptor ligands and the treatment of obesity. *Curr. Opin. Investig. Drugs.* 2004; 5:377-388]. This effect was confirmed in many investigations [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299. of 5-HT$_6$ receptors and increasing α-melanocyte-stimulating hormone emission, that, eventually, leads to reduction of food consumption [Woolley M. L. 5-ht6 receptors. *Curr. Drug Targets CNS Neurol. Disord.* 2004; 3:59-79]. At present two antagonists of 5-HT$_6$ receptors are at the first phase of clinical testing as drug candidates for weight-reducing treatment (Table 1) [http://integrity.prous.com].

In this connection searching for effective neuroprotectors capable to prevent the neurotoxic action of excessive cytosolic calcium and also searching for effective serotonin 5-HT$_6$ receptor antagonists are seemed to be original and perspective approach to design of new medicines for treatment of broad spectrum of neuralgic and neurodegenerative diseases.

There are many publications concerning various biologically active 2,3,4,5-tetrahydro-1H-pyrido[4,3-b]indoles, some of them are represented in Table 2.

TABLE 2

Some examples of known 2,3,4,5-tetrahydro-1H-pyrido[4,3-b]indoles

| N° | Formula | Pharmacological activity | Reference |
|---|---|---|---|
| A1 | 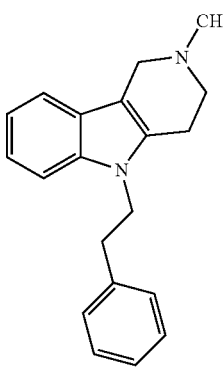 | Antihistaminic substance | Horlein, Ulrich; Hecht, Gerhard. Med. -Chem., Abhandl. Medl.-Chem. Forschungsstatten Farbenfabriken Bayer (1956), 5, 267-80. |
| A2 | 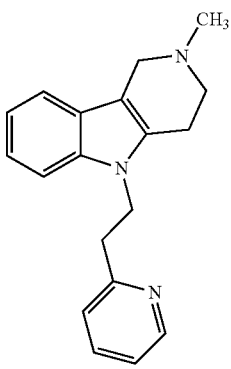 [SMILES: CN1CCc2c(c3ccccc3n2CCc2ccccn2)C1] | | Kost, J. Gen. Chem. USSR (Eng. Transl.), v. 33, 1963, p. 3538. |
| A3 | 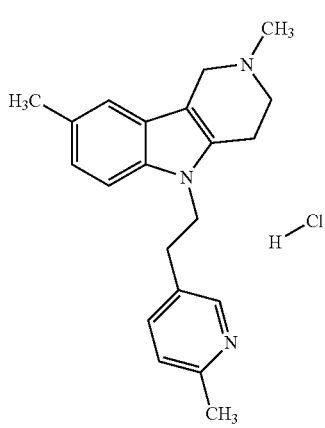 [SMILES: Cc1ccc2c(c1)c1c(n2CCc2ccc(C)nc2)CCN(C)C1 ; Cl] | Antagonist NMDA-brain receptors. Antichistaminic and neuroprotective substance, Alzheimer's disease | Mashkovsky M.D. Pharmaceutical. Pub. 13. Kharkov: Torsing, 1998. v.1, p. 280-281. *Bull Exp Biol Med.* 2000, 129(6), 544-546. U.S. Pat. No. 6,187,785 (2001) JP 09216882 (1997) RU 2140417 (1999) |

TABLE 2-continued

Some examples of known 2,3,4,5-tetrahydro-1H-pyrido[4,3-b]indoles

| N° | Formula | Pharmacological activity | Reference |
|---|---|---|---|
| A4 | 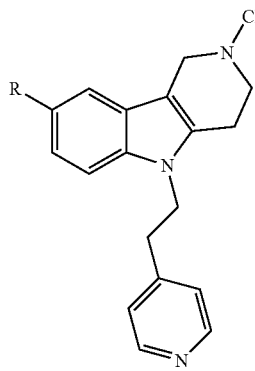<br>R = H, CH$_3$, CF$_3$, CO$_2$H,<br>CO$_2$C$_2$H$_5$ | Analgesics | U.S. Pat. No. 3,502,688 (1972) |

For the purpose of searching for new highly efficient neuroprotective medicines the authors of the invention carried out a broad investigation in the series of substituted 2,3,4,5-tetrahydro-1H-pyrido[4,3-b]indoles; as a result of it new biologically active substances, which are substituted in a certain manner 2,3,4,5-tetrahydro-1H-pyrido[4,3-b]indoles, among them the novel ones, were found.

DISCLOSURE OF THE INVENTION

In the context of the present invention, the terms are generally defined as follows:
"Azaheterocycle" means an aromatic or nonaromatic mono- or polycyclic system with at least one nitrogen atom. Azaheterocycle may have one or more "cyclic system substituents".
"Aliphatic radical" radical means the radical derived at removal of hydrogen atom from nonaromatic C—H bond. Aliphatic radical may additionally contain any substituens— aliphatic or aromatic radicals, the meanings of which are defined in this section. The representatives of aliphatic radicals include: alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, heteroaralkenyl, annelated arylcycloalkyl, annelated heteroarylcycloalkyl, annelated arylcycloalkenyl, annelated heteroarylcycloalkenyl, annelated arylheterocyclyl, annelated heteroarylheterocyclyl, annelated arylheterocyclenyl, annelated heteroarylheterocyclenyl.
"Alkenyl" means an aliphatic straight- or branched-hydrocarbon chain with 2-7 carbon atoms including C═C double bond. "Branched" means that one or more lower alkyl substituents, such as methyl, ethyl or propyl are attached to the straight alkenyl chain. Alkyl substituent may have one or more substituents such as: halogen, alkenyloxy, cycloalkyl, cyano; hydroxy, alkoxy, carboxy, alkynyloxy, aralkoxy, aryloxy, aryloxycarbonyl, alkylthio, heteroarylkyloxy, heterocyclyl, heterocyclylalkyloxy, alkoxycarbonyl, aralkoxycarbonyl, heteroaralkoxycarbonyl or $R_k{}^a R_{k+1}{}^a N$—, $R_k{}^a R_{k+1}{}^a NC(=O)$—, $R_k{}^a R_{k+1}{}^a NSO_2$—, where $R_k{}^a$ and $R_{k+1}{}^a$ independently of each other represent "amino group substituents", the meaning of which are defined in this section, for example, hydrogen, alkyl, aryl, aralkyl, heteroaralkyl, heterocyclyl or heteroaryl, or $R_k{}^a$ and $R_{k+1}{}^a$ together with the N-atom they are attached to, form through $R_k{}^a$ and $R_{k+1}{}^a$ 4-7-membered heterocyclyl or heterocyclenyl. The preferred alkyl groups are methyl, trifluoromethyl, cyclopropylmethyl, cyclopentylmethyl, ethyl, n-propyl, isopropyl, n-butyl, tert-butyl, n-pentyl, 3-pentyl, methoxyethyl, carboxymethyl, methoxycarbonylmethyl, benzyloxycarbonylmethyl, and pyridylmethyloxycarbonylmethyl. The preferred alkenyl groups are ethenyl, propenyl, n-butenyl, isobutenyl, 3-methylbuten-2-yl, n-pentenyl and cyclohexylbutenyl.
"Alkenyloxy" means alkenyl-O-group, in which alkenyl is defined in this section. Allyloxy and 3-butenyloxy are the preferred alkenyloxy groups.
"Alkenyloxyalkyl" means alkenyl-O-alkyl group, in which alkyl and alkenyl are defined in this section.
"Alkyl" means aliphatic hydrocarbon straight or branched chain with 1-12 carbon atoms. Branched means that the alkyl chain has one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k{}^a R_{k+1}{}^a N$—, $R_k{}^a R_{k+1}{}^a NC(=O)$—, $R_k{}^a R_{k+1}{}^a NC(=S)$—, $R_k{}^a R_{k+1}{}^a NSO_2$—, where $R_k{}^a$ and $R_{k+1}{}^a$ independently of each other represent "amino group substituents", the meanings of which are defined in this section, for example, hydrogen, alkyl, aryl, aralkyl, heteroaralkyl, heterocyclyl or heteroaryl, or $R_k{}^a$ and $R_{k+1}{}^a$ together with the N-atom, they are attached to, form through $R_k{}^a$ and $R_{k+1}{}^a$ 4-7-membered heterocyclyl or heterocyclenyl.

The preferred alkyl group are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl and pyridilmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k^a R_{k+1}^a N—$, $R_k^a R_{k+1}^a NC(=O)—$, annelated arylheterocyclenyl, annelated arylheterocyclyl.

"Alkyloxyalkyl" means alkyl-O-alkyl group, wherein alkyl groups are independent of one another and defined in this section. The preferred alkyloxyalkyl groups are methoxyethyl, ethoxymethyl, n-butoxymethyl, methoxypropyl and iso-propyloxyethyl.

"Alkoxycarbonyl" means alkyl-O—C(=O)-group, wherein alkyl is defined in this section. The preferred alkoxycarbonyl groups are methoxycarbonyl, ethoxycarbonyl, n-butoxycarbonyl, iso-propyloxycarbonyl, benzyloxycarbonyl and phenethyloxycarbonyl.

"Alkylthio" means alkyl-S group, wherein alkyl group is defined in this section.

"Alkoxy" means alkyl-O-group, wherein alkyl is defined in this section. The preferred alkoxy groups are methoxy, ethoxy, n-propoxy, iso-propoxy and n-butoxy.

"Alkoxycarbonylalkyl" means alkyl-O—C(=O)-alkyl-group, wherein alkyl is defined in this section. The preferred alkoxycarbonylalkyl groups are methoxy-carbonylmethyl, ethoxycarbonylmethyl, methoxy-carbonylethyl and ethoxycarbonylethyl.

"Amino group" means $R_k^a R_{k+1}^a N$-group substituted or not by "amino group substituent", the meanings of $R_k^a$ and $R_{k+1}^a$ are defined in this section, for example, amino ($NH_2$), methylamino, diethylamino, pyrrolidino, morpholino, benzylamino or phenethylamino.

"Amino acid" means a natural amino acid or non-natural amino acid, the meaning of the latter is defined in this section. The preferred amino acids are amino acids containing α- or β-amino group. Examples of natural amino acids are α-amino acids, and also alanine, valine, leucine, isoleucine, proline, phenylalanine, triptophane, methionine, glycine, serine, threonine, and cysteine.

"Amino-cyano-methylene" means $(NR_k^a R_{k-1}^a)(CN)C=$ group (radical) substituted or not by "amino group substituent" $R_k^a$ and $R_{k+1}^a$ the meanings of are defined in this section, for example, amino.

"Annelated cyclic structure" (condensed cyclic structure) means bi- or polycyclic system in which the annelated cyclic structure and cyclic structure, or polycycic structure to which it is "annelated" have at least two common atoms.

"Annelated arylheterocycloalkenyl" means an annelated aryl and heterocycloalkenyl, the meanings of which are defined in this section. Annelated arylheterocycloalkenyl may be bound through any possible atom of the cyclic system. The prefixes "aza", "oxa" or "thia" preceding the word "heterocycloalkenyl" indicate the presence of a nitrogen atom, an oxygen atom, or a sulfur atom, respectively, in the cyclic system. Annelated arylheterocycloalkenyl may have one or more "cyclic system substituents" of the same or different structure. Nitrogen and sulfur atoms in the heterocycloalkenyl part may be oxidized to an N-oxide, an S-oxide or an S-dioxide. Annelated arylheterocycloalkenyl are represented by indolinyl, 1H-2-oxoquinolinyl, 2H-1-oxoisoquinolinyl, 1,2-dihydroquinolinyl, and so on.

"Annelated arylheterocycloalkyl" means an annelated aryl and heterocycloalkyl the meanings of which are defined in this section. Annelated arylheterocycloalkyl may be bound through any possible atom of the cyclic system. The prefixes "aza", "oxa" or "thia" preceding the word "heterocycloalkyl" indicate the presence of a nitrogen atom, an oxygen atom, or a sulfur atom, respectively, in the cyclic system. Annelated arylheterocycloalkyl may have one or more "cyclic system substituens" of the same or different structure. Nitrogen and sulfur atoms in the heterocyclyl part may be oxidized to an N-oxide, an S-oxide and an S-dioxide. Annelated arylheterocycloalkyls are represented by indolyl, 1,2,3,4-tetrahydroisoquinolinyl, 1,3-benzodiocolyl, and so on.

"Annelated arylcycloalkenyl" means an annelated aryl and cycloalkenyl, the meanings of which are defined in this section. Annelated arylcycloalkenyl may be bound through any possible atom of the cyclic system. Annelated arylcycloalkenyl may have one or more "cyclic system substituents" of the same or different structure. Annelated arylcycloalkenyls are represented by 1,2-dihydronaphthalenyl, indenyl and so on.

"Annelated arylcycloalkyl" means an annelated aryl and cycloalkyl, the meanings of which are defined in this section. Annelated arylcycloalkyl may be bound through any possible atom of the cyclic system. Annelated arylcycloalkyl may have one or more "cyclic system substituens" of the same or different structure. Annelated arylcycloalkyl are represented by indaninyl, 1,2,3,4-tetrahydronaphthyl, 5,6,7,8-tetrahydronapht-1-yl, and so on.

"Annelated heteroarylcycloalkenyl" means an annelated heteroaryl and cycloalkenyl, the meanings of which are defined in this section. Annelated heteroarylcycloalkenyl may be bound through any possible atom of the cyclic system. The prefixes "aza", "oxa" or "thia" preceding the word "heteroaryl" indicate the presence of a nitrogen atom, an oxygen atom, or a sulfur atom, respectively, in the cyclic system. Annelated heteroarylcycloalkenyl may have one or more "cyclic system substituents" of the same or different structure. The nitrogen atom in the heteroaryl part may be oxidized to N-oxide. Annelated heteroarylcycloalkenyls are represented by 5,6-dihydroquinolinyl, 5,6-dihydroisoquinolinyl, 4,5-dihydro-1H-benzimidazolyl, and so on.

"Annelated heteroarylcycloalkyl" means an annelated heteroaryl and cycloalkyl the value of which is defined in this section. Annelated heteroarylcycloalkyl may be bound through any possible atom of the cyclic system. The prefixes "aza", "oxa" or "thia" preceding the word "heteroaryl" indicate the presence of a nitrogen atom, an oxygen atom, or a sulfur atom, respectively, in the cyclic system. Annelated heteroarylcycloalkyl may have one or more "cyclic system substituens" that may be identical or different. Nitrogen atom in the heteroaryl part may be oxidized to an N-oxide. Annelated heteroarylcycloalkyls are represented by 5,6,7,8-tetrahydroquinolinyl, 5,6,7,8-tetrahydroisoquinolinyl, 4,5,6,7-tetrahydro-1H-benzimidazolyl, and so on "Annelated heteroarylheterocyclenyl" means an annelated heteroaryl and heterocyclenyl, the value of which is defined in this section. Annelated heteroarylheterocyclenyl may be bound through any possible atom of the cyclic system. The prefixes "aza", "oxa" or "thia" preceding the word "heteroaryl" indicate the presence of a nitrogen atom, an oxygen atom, or a sulfur atom, respectively, in the cyclic system. Annelated heteroarylheterocyclenyl may have one or more "cyclic system substituents" that may be identical or different. The nitrogen atom in the heteroaryl part may be oxidized to an N-oxide. The nitrogen atom and the sulfur atom in the heterocyclenyl part may be oxidized to an N-oxide, an S-oxide and an S-dioxide. Annelated heteroaryl-heterocyclenyls are represented by 1,2-dihydro[2,7]naphthiridinyl, 7,8-dihydro[1,7]naphthiridinyl, 6,7-dihydro-3H-imidazo[4,5-c]pyridyl, and so on.

"Annelated heteroarylheterocyclyl" means an annelated heteroaryl and heterocyclyl, the value of which is defined in this section. Annelated heteroarylheterocyclyl may be bound through any possible atom of the cyclic system. The prefixes "aza", "oxa" or "thia" preceding the word "heteroaryl" indicate the presence of a nitrogen atom, an oxygen atom, or a sulfur atom, respectively, in the cyclic system. Annelated heteroarylheterocyclyl may have one or more "cyclic system substituents" that may be identical or different. The nitrogen atom in the heteroaryl part may be oxidized to an N-oxide. The nitrogen atom and the sulfur atom in the heterocyclyl part may be oxidized to an N-oxide, an S-oxide and an S-dioxide. Annelated heteroarylheterocyclyls are represented by 2,3-dihydro-1H-pyrrolo[3,4-b]quinolin-2-yl, 2,3-dihydro-1H-pyrrolo[3,4-b]indol-2-yl, 1,2,3,4-tetrahydro[1,5]naphthiridinyl, and so on.

"Antagonists" mean ligandes which is related with definite receptors and does not cause active cellular response. Antagonists prevent linkage agonists and receptors and by that blocking specific transfer of the signal.

"Antidepressant" means a medicine intended for treatment of depression.

"Anxiolytic" (tranquilizer) means a medicine intended for treatment of anxious disorders.

"Aralkenyl" means aryl-alkenyl group, wherein aryl and alkenyl are defined in this section. For example, 2-phenethenyl is aralkenyl group.

"Aralkyl" means alkyl group substituted by one or more aryl groups, wherein aryl and alkyl are defined in this section. For example, benzyl-, 2,2-diphenylethyl- or phenethyl- are aralkyl groups.

"Aralkylamino" means aryl-alkyl-NH-group, wherein aryl and alkyl are defined in this section.

"Aralkylsulfinyl" means aralkyl-SO-group, wherein aralkyl is defined in this section.

"Aralkylsulfonyl" means aralkyl-SO$_2$-group, wherein aralkyl is defined in this section.

"Aralkylthio" means aralkyl-S-group, wherein aralkyl is defined in this section.

"Aralkoxy" means aralkyl-O-group, wherein aralkyl is defined in this section. For example, benzyloxy or 1- or 2-naphthylenmethoxy are aralkyl groups.

"Aralkoxyalkyl" means aralkyl-O-alkyl-group, wherein aralkyl and alkyl are defined in this section. For example, benzyloxyethyl is aralkyl-O-alkyl group.

"Aralkoxycarbonyl" means aralkyl-O—C(═O)-group, wherein aralkyl is defined in this section. Benzyloxycarbonyl is an example of aralkoxycarbonyl group.

"Aralkoxycarbonylalkyl" means aralkyl-O—C(═O)-alkyl-group, wherein aralkyl and alkyl are defined in this section. Benzyloxycarbonylmethyl or benzyloxycarbonylethyl are examples of aralkoxycarbonylalkyl groups.

"Aryl" means an aromatic monocyclic or polycyclic system containing 6 to 14 carbon atoms, preferably from 6 to 10 carbon atoms. Aryl may contain one or more "cyclic system substituents" that may be identical or different. Aryl groups are represented by phenyl or naphthyl, substituted phenyl or substituted naphthyl. Aryl may be annelated to non-aromatic cyclic system or heterocyclic structure.

"Arylcarbamoyl" means aryl-NHC(═O)-group, wherein aryl is defined in this section.

"Aryloxy" means aryl-O-group, wherein aryl is defined in this section. Phenoxy- and 2-naphthyloxy- are the representatives of aryloxy groups.

"Aryloxycarbonyl" means aryl-O—C(═O)-group, wherein aryl is defined in this section. Phenoxycarbonyl and 2-naphthoxycarbonyl are the representatives of aryloxycarbonyl groups.

"Arylsulfinyl" means aryl-SO-group, wherein aryl is defined in this section.

"Arylsulfonyl" means aryl-SO$_2$-group, wherein aryl is defined in this section.

"Arylthio" means aryl-S-group, wherein aryl is defined in this section. Phenylthio- and 2-naphthylthio- are the representatives of arylthio groups.

"Aroylamino" means aroyl-NH-group, wherein aroyl is defined in this section.

"Aroyl" means aryl-C(═O)-group, wherein aryl is defined in this section. Benzoyl-, 1- and 2-naphthoyl- are the representatives of aroyl groups.

"Aromatic radical" means a radical obtained by dropping a hydrogen atom from the aromatic C—H bond. "Aromatic" radical contains aryl and heteroaryl cyclic structures defined in this section. Aryl and heteroaryl cyclic structures may further contain substituents, such as aliphatic or aromatic radicals defined in this section. Aromatic radicals are represented by aryl, annelated cycloalkenylaryl, annelated cycloalkylaryl, annelated heterocyclylaryl, annelated heterocyclenylaryl, heteroaryl, annelated cycloalkylheteroaryl, annelated cycloalkenylheteroaryl, annelated heterocyclenylheteroaryl and annelated heterocyclylheteroaryl.

"Aromatic cyclic structure" means a planar cyclic system in which all cyclic system atoms are involved in forming a common conjugation system containing, according to Hückel's rule, (4n+2) π-electrons (n is a non-negative number). Examples of aromatic cyclic structures are benzene, naphthalene, anthracene, and so on. In the case of "heteroaromatic cyclic structures", the conjugation system involves π-electrons and p-electrons of heteroatoms, their total number being (4n+2) as well. Examples of such cyclic structures are pyridine, thiophene, pyrrole, furan, thiazole, and so on. The aromatic cyclic structure may have one or more "cyclic system substituents" and may be annelated to non-aromatic cyclic structure, heteroaromatic or heterocyclic system.

"Acyl" means H—C(═O)—, alkyl-C(═O)—, cycloalkyl-C(═O), heterocyclyl-C(═O)—, heterocyclyl-alkyl-C(═O)—, aryl-C(═O)—, arylalkyl-C(═O)—, heteroaryl-C(═O)—, heteroarylalkyl-C(═O)— groups, wherein alkyl-, cycloalkyl-, heterocyclyl-, heterocyclylalkyl-, aryl-, arylalkyl-, heteroaryl-, heteroarylalkyl are defined in this section.

"Acylamino" means acyl-NH-group wherein acyl is defined in this section.

"Bifunctional reagent" means a chemical compound with two reaction centers, both of them taking part in the reactions simultaneously or consecutively. For example, reagents containing carboxy and aldehyde or keto groups are bifunctional reagents such as 2-formylbenzoic acid, 2-(2-oxo-ethylcarbamoyl)-benzoic acid, 2-(3-formylthiophen-2-yl)-benzoic acid or 2-(2-formylphenyl)-thiophene-3-carboxylic acid.

"1,2-Ethenyl radical" means —CH═CH-group with one or more "alkyl substituents" that may be identical or different, the value of which are defined in this section.

"Halogen" means fluorine, chlorine, bromine and iodine. Preference is given to fluorine, chlorine and bromine.

"Heteroannelated cyclic structure" means that the cyclic structure that is attached (annelated or condenced) to another cyclic or polycyclic structure contains at least one heteroatom.

"Heteroaralkenyl" means heteroaryl-alkenyl-group, wherein heteroaryl and alkenyl are defined in this section. Preferably, heteroarylalkenyl contains the lower alkenyl group. Heteroarylalkenyls are represented by 4-pyridylethenyl, thienylethenyl, imidazolylethenyl, pyrazinylethenyl, and so on.

"Heteroaralkyl" means heteroaryl-alkyl-group, wherein heteroaryl and alkyl are defined in this section. Heteroaralkyls are represented by pyridylmethyl, thienylmethyl, furylmethyl, imidazolylmethyl, pyrazinylmethyl, and so on.

"Heteroaralkyloxy group" means heteroarylalkyl-O-group, wherein heteroarylalkyl is defined in this section. Heteroaralkyloxy group are represented by 4-pyridylmethyloxy, 2-thienylmethyloxy, and so on.

"Heteroaryl" means aromatic monocyclic or polycyclic system with 5 to 14 carbon atoms, preferably 5-10 C-atoms, wherein one or more carbon atoms are substituted by one or more heteroatoms, such as N, S or O. The prefixes "aza", "oxa" or "thia" preceding the word "heteroaryl" indicate the presence of a nitrogen atom, an oxygen atom, or a sulfur atom, respectively, in the cyclic system. Nitrogen atom in the heteroaryl part may be oxidized to an N-oxide. Heteroaryl may have one or more "cyclic system substituents" that may be identical or different. Heteroaryl radicals are represented by pyrrolyl, furanyl, thienyl, pyridyl, pyrazinyl, pyrimidinyl, isooxazolyl, isothiazolyl, tetrazolyl, oxazolyl, thiazolyl, pyrazolyl, furazanyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothiazenyl, quinolinyl, imidazolyl, thienopyridyl, quinazolinyl, thienopyrimidinyl, pyrrolopyridinyl, imidazopyridinyl, isoquinolinyl, benzoazaindolyl, 1,2,4-triazinyl, thienopyrrolyl, furopyrrolyl, and so on.

"Heteroarylsulfonylcarbamoyl" means heteroaryl-SO$_2$—NH—C(=O)-group, wherein heteroaryl is defined in this section.

"Heteroaroyl"—means heteroaryl-C(=O)-group, wherein heteroaryl is defined in this section. Heteroaroyl groups are represented by nicotinoyl, thienoyl, pyrazoloyl, and so on.

"Heterocyclenyl" means non-aromatic monocyclic or polycyclic system containing 3 to 13 carbon atoms, preferably from 5 to 13 carbon atoms in which one or several carbon atoms are replaced with a heteroatom such as nitrogen, oxygen or sulfur, and which contains at least one double carbon-carbon bond or double carbon-nitrogen bond. The prefixes "aza", "oxa" or"thia" preceding the word "heterocyclenyl" indicate the presence of a nitrogen atom, an oxygen atom, or a sulfur atom, respectively, in the cyclic system. Heterocyclenyl may have one or more "cyclic system substituens" that may be identical or different. Nitrogen atom and sulfur atom in the heterocyclenyl part may be oxidized to an N-oxide, an S-oxide and an S-dioxide. Heterocyclenyl groups are represented by 1,2,3,4-tetrahydropyridinyl, 1,2-dihydropyridinyl, 1,4-dihydropyridinyl, 2-pyrrolinyl, 3-pyrrolinyl, 2-imidazolyl, 2-pyrazolinyl, dihydrofuranyl, dihydrothiophenyl, and so on.

"Heterocyclyl" means an aromatic or nonaromatic saturated monocyclic or polycyclic system containing 3 to 10 carbon atoms, preferably 5 to 6 carbon atoms, in which one or several carbon atoms are replaced with a heteroatom such as nitrogen, oxygen or sulfur. The prefixes "aza", "oxa" or "thia" preceding the word "heterocyclyl" indicate the presence of a nitrogen atom, an oxygen atom, or a sulfur atom, respectively, in the cyclic system. Heterocyclyl may have one or more "cyclic system substituents" that may be identical or different. Nitrogen atom and sulfur atom in heterocyclyl fragment may be oxidized to an N-oxide, an S-oxide and an S-dioxide. Heterocyclyls are represented by piperidinyl, pyrrolidinyl, piperazinyl, morpholinyl, thiomorpholinyl, thiazolidinyl, 1,4-dioxan-2-yl, tetrahydrofuranyl, tetrahydrothiophenyl, and so on.

"Heterocyclyloxy" means heterocyclyl-O-group, wherein heterocyclyl is defined in this section.

"Hydrate" means stoichiometric or nonstoichiometric compositions of the compounds or their salts with water.

"Hydroxyalkyl" means HO-alkyl-group, wherein alkyl is defined in this section.

"Depression" means big depression; the incidental, chronic and recurring form of the big depression; dysthymic disorder (dysthymia); cyclotymias; affective disorder; a syndrome of seasonal affective disorder; bipolar disorder, including bipolar disorders of I and II type; and also other depressive disorders and conditions. Depression also means the depressions accompanying Alzheimer's disease, a vascular dementia; disorder of the mood induced by alcohol and substances; schizoaffective disorder of depressive type; disorder of adaptation. Except for that, depression includes a depression of oncologic patients; a depression at Parkinson's disease; depressions after a myocardial infarction; depressions of fruitless women; pediatric depression; postnatal depression; the depressions accompanying somatic, neuralgic and other diseases "Substituent" means a chemical radical that is attached to a scaffold (fragment), for example, "alkyl substituent", "amino group substituent", "carbamoyl substituent", and "cyclic system substituent", the values of which are defined in this section.

"Alkyl substituent" means a chemical radical that is attached to alkyl or alkenyl group, the meanings of which are defined in this section. It may be selected from hydrogen, alkyl, halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonyl, heteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k^a R_{k+1}^a N$—, $R_k^a R_{k+1}^a NC(=O)$—, $R_k^a R_{k+1}^a NSO_2$—, wherein $R_k^a$ and $R_{k+1}^a$ are, independently from one another, "amino group substituent", the meanings of which are defined in this section, for example, hydrogen, alkyl, aryl, aralkyl, heteroaralkyl, heterocyclyl or heteroaryl, or $R_k^a$ and $R_{k+1}^a$ together with a nitrogen atom to which they are bound, form through $R_k^a$ and $R_{k+1}^a$ a four- to seven-member heterocyclyl or heterocyclenyl. The preferred alkyl groups are represented by methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl, methoxycarbonylmethyl, and pyridylmethyloxycarbonylmethyl. The preferred "alkyl substituents" are represented by cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k^a R_{k+1}^a N$—, $R_k^a R_{k+1}^a NC$ (=O)—, annelated arylheterocyclenyl, annelated arylheterocyclyl. The meanings of "alkyl group substituents" are defined in this section.

"Amino group substituent" means a substituent attached to an amino group. Amino group substituent represents hydrogen, alkyl, cycloalkyl, aryl, heteroaryl, heterocyclyl, acyl, aroyl, alkylsulfonyl, arylsulfonyl, heteroarylsulfonyl, alkylaminocarbonyl, arylaminocarbonyl, heteroarylaminocarbonyl, heterocyclylaminocarbonyl, alkylaminothiocarbonyl, arylaminothiocarbonyl, heteroarylaminothiocarbonyl, heterocyclylaminothiocarbonyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonylalkyl, aralkoxycarbonylalkyl, heteroaralkyloxycarbonylalkyl. The meanings of "amino group substituents" are defined in this section.

"Carbamoyl substituent" means a substituent attached to carbamoyl group, the meaning of which is defined in this section. Carbamoyl substituent may be selected from hydrogen, alkyl, cycloalkyl, aryl, heteroaryl, heterocyclyl, alkoxycarbonylalkyl, aralkoxycarbonylalkyl, heteroaralkyloxycarbonylalkyl or $R_k^a R_{k+1}^a N$—, $R_k^a R_{k+1}^a NC(=O)$-alkyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl. The preferred "carbamoyl substituents" are represented by alkyl, cycloalkyl, aryl, heteroaryl, heterocyclyl, alkoxycarbonylalkyl, aralkoxycarbonylalkyl, heteroaralkyloxycarbonylalkyl or $R_k^a R_{k+1}^a N$—, $R_k^a R_{k+1}^a NC(=O)$-alkyl, annelated arylheterocyclenyl, annelated arylheterocyclyl. The meanings of "carbamoyl substituents" are defined in this section.

"Nucleophilic substituent" is a chemical radical that is attached to the scaffold as a result of a reaction with a nucleophilic reagent, for example, one selected from the group of primary or secondary amines, alcohols, phenols, mercaptans and thiophenols.

"Cyclic system substituent" means a substituent attached to an aromatic or nonaromatic cyclic system selected from hydrogen, alkyl, alkenyl, alkynyl, aryl, heteroaryl, aralkyl, heteroaralkyl, hydroxy, hydroxyalkyl, amino, aminoalkyl, alkoxy, aryloxy, acyl, aroyl, halogen, nitro, cyano, carboxy, alkoxycarbonyl, aryloxycarbonyl, aralkoxycarbonyl, alkyloxyalkyl, aryloxyalkyl, heterocyclyloxyalkyl, arylalkyloxyalkyl, heterocyclylalkyloxyalkyl, alkylsulfonyl, arylsulfonyl, heterocyclylsulfonyl, alkylsulfinyl, arylsulfinyl, heterocyclylsulfinyl, alkylthio, arylthio, heterocyclylthio, alkylsulfonylalkyl, arylsulfonylalkyl, heterocyclylsulfonylalkyl, alkylsulfinylalkyl, arylsulfinylalkyl, heterocyclylsulfinylalkyl, alkylthioalkyl, arylthioalkyl, heterocyclylthioalkyl, arylalkylsulfonylalkyl, heterocyclylalkylsulfonylalkyl, arylalkylthioalkyl, heterocyclylalkylthioalkyl, cycloalkyl, cycloalkenyl, heterocyclyl, heterocyclenyl, amidino, $R_k^a R_{k+1}^a N$—, $R_k^a N=$, $R_k^a R_{k+1}^a N$-alkyl, $R_k^a R_{k+1}^a NC(=O)$— or $R_k^a R_{k+1}^a NSO_2$—, wherein $R_k^a$ and $R_{k+1}^a$ are, independently from one another, an "amino group substituent", the meanings of which are defined in this section, for example, hydrogen, optionally substituted alkyl, optionally substituted aryl, optionally substituted aralkyl, optionally substituted heteroaralkyl or $R_k^a R_{k+1}^a N$-substituent wherein $R_k^a$ may be acyl or aroyl, the value of $R_{k+1}^a$ is defined above, or "cyclic system substituents" are $R_k^a R_{k+1}^a NC(=O)$— or $R_k^a R_{k+1}^a NSO_2$—, wherein $R_k^a$ and $R_{k+1}^a$, together with a nitrogen atom to which they are bound, form through $R_k^a$ and $R_{k+1}^a$ a four to seven-member heterocyclyl or heterocyclenyl.

"Electrophilic substituent" means a chemical radical attached to the scaffold as a result of a reaction with an electrophilic reagent, for example, one selected from a group of organic acids or their derivatives (anhydrides, imidazolides, acid chlorides), organic sulfonic acid esters or chlorides, organic haloformates, organic isocyanates and organic isothiocyanates.

"Substituted amino group" means $R_k^a R_{k+1}^a N$-group wherein $R_k^a$ and $R_{k+1}^a$ are the substituents of an amino group, the meanings of which are defined in this section.

"Substituted carboxy group" means C(O)OR-group. Substituted carboxyl has substituent R selected from alkenyl, alkyl, aryl, heteroaryl, heterocyclyl, the meanings of which are defined in this section.

"Substituted mercapto group" means SR, S(O)R or $S(O_2)R$ group wherein substituent R represents alkenyl, alkyl, aryl, heteroaryl, heterocyclyl, the meanings of which are defined in this section.

"Protective group" (PG) means a chemical radical that is attached to the scaffold or intermediate product of synthesis to provide temporary protection for amino group in multifunctional compounds, including, but not limited to: an amide substituent, such as formyl, optionally substituted acetyl (for example, trichloroacetyl, trifluoroacetyl, 3-phenylpropionyl and so on), optionally substituted benzoyl and so on; a carbamate substituent, such as: optionally substituted $C_1$-$C_7$-alkoxycarbonyl, for example, methyloxycarbonyl, ethyloxycarbonyl, tert-butyloxycarbonyl, 9-fluorenylmethyloxycarbonyl (Fmoc) and others; optionally substituted $C_1$-$C_7$-alkyl substituent, for example tert-butyl, benzyl, 2,4-dimethoxybenzyl, 9-phenylfluorenyl and others; sulfonyl substituent, for example, benzenesulfonyl, p-toluenesulfonyl, etc. More specifically "Protective groups" are described in the book: Protective groups in organic synthesis, Third Edition, Greene, T. W. and Wuts, P. G. M. 1999, p. 494-653. John Wiley & Sons, Inc., New York, Chichester, Weinheim, Brisbane, Toronto, Singapore.

"Protected primary or secondary amine" means a group of the formula $R_k^a R_{k+1}^a N$—, wherein $R_k^a$ is a protective group PG, $R_{k+1}^a$ is hydrogen, an "amino group substituent", the meaning of which is defined in this section, for example, selected from alkyl, alkenyl, aryl, aralkyl, annelated arylcycloalkenyl, annelated arylcycloalkyl, annelated arylheterocyclenyl, annelated arylheterocyclyl, cycloalkyl, cycloalkenyl, heteroaralkyl, heteroaryl, annelated heteroarylcycloalkenyl, annelated heteroarylcycloalkyl, annelated heteroarylheterocyclenyl, annelated heteroarylheterocyclyl, heterocyclenyl or heterocyclyl.

"Imino group" means $R_k^a N=$ group substituted or not by an "amino group substituent" $R_k^a$, the meaning of which is defined in this section, for example, imino (HN=), methylimino ($CH_3N=$), ethylimino ($C_2H_5N=$), benzylimino ($PhCH_2N=$) or phenethylimino ($PhCH_2CH_2N=$).

"Inert substituent" ("non-interfering substituent") means a low- or non-reactive radical, including, but not limited to: $C_1$-$C_7$ alkyl, $C_2$-$C_7$ alkenyl, $C_2$-$C_7$ alkynyl, $C_1$-$C_7$ alkoxy, $C_7$-$C_{12}$ aralkyl, substituted by inert substituents aralkyl, $C_7$-$C_{12}$ heterocyclylalkyl, substituted by inert substituents heterocyclylalkyl, $C_7$-$C_{12}$ alkaryl, $C_3$-$C_{10}$ cycloalkyl, $C_3$-$C_{10}$ cycloalkenyl, phenyl, substituted phenyl, toluyl, xylenyl, biphenyl, $C_2$-$C_{12}$ alkoxyalkyl, $C_2$-$C_{10}$ alkylsulfinyl, $C_2$-$C_{10}$ alkylsulfonyl, $(CH_2)_m$—O—($C_1$-$C_7$ alkyl), —$(CH_2)_m$—N($C_1$-$C_7$ alkyl)$_n$, aryl; aryl substituted by halogen or inert substituent, alkoxy substituted by inert substituent, fluoroalkyl, aryloxyalkyl, heterocyclyl, heterocyclyl substituted by inert substituents and nitroalkyl; where m and n are ranged from 1 to 7. The preferred "non-interfering substituents" are represented by $C_1$-$C_7$ alkyl, $C_2$-$C_7$ alkenyl, $C_2$-$C_7$ alkynyl, $C_1$-$C_7$ alkoxy, $C_7$-$C_{12}$ aralkyl, $C_7$-$C_{12}$ alkaryl, $C_3$-$C_{10}$ cycloalkyl, $C_3$-$C_{10}$ cycloalkenyl, $C_1$-$C_7$ alkyl substituted by inert substituents, phenyl; phenyl substituted by inert substituents, $(CH_2)_m$—O—($C_1$-$C_7$ alkyl), —$(CH_2)_m$—N($C_1$-$C_7$ alkyl)$_n$, aryl; aryl substituted by inert substituents, heterocyclyl and heterocyclyl substituted by inert substituents.

"Carbamoyl" means $C(=O)NR_k{}^a R_{k+1}{}^a$— group. Carbamoyl may have one or more "carbamoyl substituents" $R_k{}^a$ and $R_{k+1}{}^a$, selected from hydrogen, alkyl, alkenyl, aryl, heteroaryl, heterocyclyl, the meanings of which are defined in this section.

"Carbamoylazaheterocycle" means azaheterocycle with at least one carbamoyl group as a "cyclic system substituent". The meanings of "azaheterocycle", "cyclic system substituent", and "carbamoyl group" are defined in this section.

"Carboxy" means HOC(=O)— (carboxy) group.

"Carboxyalkyl" means HOC(=O)-alkyl group, wherein alkyl is defined in this section.

"Carbocyclic structure" means mono- or polycyclic system consisting of carbon atoms only. Carbocyclic rings can be either aromatic or alicyclic. Alicyclic polycyclic structures may have one or more common atoms. In the case of one common atom, spiro-carbocyclic compounds (for example, spiro[2,2]pentane) are formed; in the case of two common atoms, various condensed systems (for example, decaline) are produced; three common atoms result in bridged systems (for example, bicycle[3,3,1]nonane); a larger number of common atoms produce various polyhedral systems (for example, adamantane). Alicyclic structures may be "saturated", such as, for example, cyclohexane, or "partially saturated", such as, for example, tetraline.

"Cognitive disorders" or disorders of cognitive functions" mean disorder (weakness) of mental capabilities including attentiveness, memory, cogitation, cognition, education, verbal, mental, executive and creative abilities, time and space orientation; in particular, cognitive disorders associated with Alzheimer's disease, Parkinson's and Hungtington's diseases, senile dementia; age-associated memory impairment, AAMI; dysmetabolic encephalopathy; psychogenous memory impairment; amnesia; amnesic disturbances; transit global amnesia; dissociative amnesia; vascular dementia; light or mild cognitive impairment, MCI; attention deficit hyperactivity disorder (AD/HD); cognitive impairments, accompanying psychotic diseases, epilepsy, delirium, autism, psychosis, Down's syndrome, bipolar disorders and depression; AIDS-associated dementia; dementias at hypothyroidism; dementia connected with alcohol, substances causing dependability and neurotoxins; dementia accompanying neurodegenerative diseases, for example, cerebellar degeneracy and amyotrophic lateral sclerosis; cognitive disturbances connected with cerebral crisis, infectious and oncological brain diseases as well as traumatic brain injury; cognitive functions damages associated with autoimmune and endocrine diseases, and others.

"Combinatorial library" means a collection of compounds produced by parallel synthesis and intended for searching for a hit or leader compound, and for optimization of physiological activity of the hit or leader as well, each compound of the library corresponds to the common scaffold, in this way the library is a collection of related homologues or analogues.

"Medicine"—is a compound (or a mixture of compounds in the form of pharmaceutical composition), in the form of tablets, capsules, injections, ointments intended for restoration, improvement or modification of physiological functions at humans and animals, and for treatment and prophylaxis of diseases, diagnostics, anesthesia, contraception, cosmetology and others.

"Ligandes" (from latin ligo) represent chemical compounds (small molecule, peptide, protein and others) or inorganic ion, capable to interact with receptors which convert this interaction into specific signal.

"Methylene radical" means —$CH_2$-group with one or two "alkyl substituents" that may be identical or different, the values of which are defined in this section.

"Nonaromatic cyclic structure" (saturated cyclic structure or partly saturated cyclic structure) means nonaromatic cyclic or polycyclic system formally derived as a result of complete or partial hydrogenization of unsaturated —C=C— or —C=N— bonds. A nonaromatic cyclic structure may have one or more "cyclic system substituents" and may be annelated to aromatic, heteroaromatic or heterocyclic systems. Examples of nonaromatic cyclic structures are cyclohexane or piperidine; examples of partly saturated cyclic structures are cyclohexene or piperidine.

"Neuro-degenerative diseases" means specific conditions and diseases, described damage and primary destruction of populations of nervous cells to the certain areas of the central nervous system. Neuro-degenerative diseases include but are not limited: Alzheimer's disease; Parkinson disease; Huntington disease (chorea); multiocular sclerosis; cerebellar degeneracy; amyotrophic lateral sclerosis; dementias with Lewy bodies; spinal muscular atrophy; peripheral neuropathy; spongy encephalitis (Creutzfeld-Jakob Disease); AIDS dementia; multi-infract dementia; frontotemporal dementias; leukoencephalopathy (spongy degeneration of white matter); chronic neuro-degenerative diseases; cerebral crisis; ischemic, reperfussion and hypoxic brain damage; epilepsy; cerebral ischemia; glaucoma; traumatic brain injury; Down's syndrome; encephalomyelitis; meningitis; encephalitis; neuroblastoma; schizophrenia; depression. Except for neuro-degenerative diseases includes pathological states and disorders connected with hypoxia, substance abuse, causing dependability, under neurotoxins influence; infectious and oncological brain diseases as well as neuronal damages associated with autoimmune and endocrine diseases and others.

"Non-natural aminoacid" means an aminoacid of non nucleinic origin. D-isomers of natural α-aminoacids, such as aminobutyric acid, 2-aminobutyric acid, γ-aminobutyric acid, N-α-alkylaminoacids, 2,2-dialkyl-α-aminoacids, 1-aminocycloalkylcarboxylic acids, β-alanine, 2-alkyl-β-alanines, 2-cycloalkyl-β-alanines, 2-aryl-β-alanines, 2-heteroaryl-β-alanines, 2-heterocyclyl-β-alanines and (1-aminocycloalkyl)-acetic acids are the representatives of non natural aminoacids in which the meanings of alkyl, cycloalkyl, aryl, heteroaryl and heterocyclyl are defined in this section.

"Optionally aromatic cycle" means a cycle which may be either aromatic or non-aromatic, the meanings of which are defined in this section.

"Optionally substituted radical" means a radical without or with one or more substituents.

"Optionally annelated (condensed) cycle" means a condensed or non-condensed cycle, the meanings of which are defined in this section.

"Lower alkyl" means a linear or branched alkyl radical containing from 1 to 4 carbon atoms.

"Nootrops" or "Nootropics" (neurometabolic stimulats) are medicines taken for cognition enhancing.

"Parallel synthesis" means a method for carrying out a chemical synthesis of combinatorial library of individual compounds.

"1,3-Propylene radical" means —$CH_2$—$CH_2$—$CH_2$-group with one or more "alkyl substituents" that may be identical or different, the values of which are defined in this section.

"Psychotic diseases" are diseases or diseased states associated with mental disturbance and/or mentality frustration. "Psychotic diseases" includes affective disorders (bipolar affective disorders, big depression, hypomania, minor depression, maniacal syndrome, Cotard's syndrome, cyclothymia, schizo-affective disorders and so on), intellectual-mnestic disorders; manias (hypomania, graphomania, cleptomania, compulsive shopping, mania of persecution, pornographomania, erotomania and so on); disorder of multiple personality, amentia, alcoholomania, deliration, delirium syndrome, hallucinosis, hallucinations, lucinatory effects, homicidomania, delirium; illusion, querulous paranoiaclinical lycanthropy, macropsia, antagonistic delusion, micropsia, narcomania; anorexia nervosa, oneiroid syndrome, paranoid, paranoia, paraphrenia, pseudohallucinations, psychosis, Cotard's syndrome, schizoaffective disorder, shhizo typical disorder, schizophrenia, schizo-affective psychosis disorder, schizophrenomorphic disorder, Shrebera's syndrome, Daniel Paul's syndrome), phobias (agarophobia, arachnephobia, autophobia, verminophobia, hydrosophobia, hydrophobia, demophobia, zoophobia, carcinophobia, claustrophobia, climacophobia, xenophobia, misophobia, radiophobia, photophobia; skoliephobia, scotophobia, social phobia, tetraphobia, triskaidekaphobia, erotophobia); alcoholic psychosis, alcoholic palimpsest, allotriophagy, aphasia, graphomania, dissociative fugue state, dissociative disorders; dysphorias, internet-dependences, hypochondria, hysteria, kopophobia, delirium of persecution, melancholy, misanthropy, obsession, panic attacks, Asperger's syndrome, Capgras' syndrome, Munchausen's syndrome, Retta's syndrome, Fregoly's syndrome, syndrome of attention and hyperactivitydeficit, obsessive neurosis syndrome,-compulsive disorder, syndrome of chronic narcotization consequences, syndrome of psychic automatism, syndrome of infantile autism, madness, taphophilia, anxiety conditions, Hikikomory's syndrome, erotographomania and so on.

"Leader compound" (leader) means a compound of outstanding (maximum) physiological activity associated with a concrete bio-target related to a definite (or several) pathology or disease.

"Hit compound" (hit) means a compound demonstrated the desired physiological activity during the primary screening process.

"Sulfamoyl group" means $R_k^a R_{k+1}^a NSO_2$-group substituted or not by "amino group substituents" $R_k^a$ and $R_{k+1}^a$, the values of which are defined in this section.

"Sulfonyl" means R—$SO_2$-group wherein R may be selected from alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, the values of which are defined in this section.

"Template" means the common structural formula of a group of compounds or compounds contained in the "combinatorial library".

"Therapeutic cocktail" is a combination of two or more medicines administered simultaneously, which have different mechanisms of pharmacological action and are aimed at different bio-targets involved in the disease pathogenesis.

"Thiocarbamoyl" means $R_k^a R_{k+1}^a NC(=S)$-group. Thiocarbamoyl may have one or more "amino group substituents" $R_k^a$ and $R_{k+1}^a$, the values of which are defined in this section, for example, alkyl, alkenyl, aryl, heteroaryl and heterocyclyl the values of which are defined in this section.

"Anxiety disorders" means generalized (inconcrete) anxiety; acute uncontrolled anxiety; panic disorder; phobia, for a example, agoraphobia (acute fear of crowded place) or social (acute fear of humiliation at presence of other people) or any other phobia (acute fear of particular subjects, animals or situations, in the form of phobia of height, of medical procedures, lifts, open space etc.); an obsessional condition (obsessive-compulsive disorder); posttraumatic stress disorder and acute stress disorder. Besides, anxiety disorders include anxiety conditions induced by alcohol or substances; anxiety under adaptation; as well as mixed forms of anxiety disorders and depression.

"Cycloalkyl" means non-aromatic monocyclic or polycyclic system containing from 3 to 10 carbon atoms. Cycloalkyl may have one or more "cyclic system substituents" that may be identical or different. The cyclic system groups are represented by cyclopropyl, cyclobutyl, cyclopentyl, cyclohexyl, decalinyl, norbornyl, adamant-1-yl, and so on. Cycloalkyl may be annelated to aromatic cycle or heterocycle. The preferred "cyclic system substituents" are represented by alkyl, aralkoxy, hydroxy or $R_k^a R_{k+1}^a N$—, the values of which are defined in this section.

"Cycloalkylcarbonyl" means cycloalkyl-C(=O)-group, wherein the value of cycloalkyl is defined in this section. Cyclopropylcarbonyl and cyclohexylcarbonyl are the representatives of cycloalkylcarbonyl groups.

"Cycloalkoxy" means cycloalkyl-O-group, wherein the value of cycloalkyl is defined in this section.

"Pharmaceutical composition" means a composition containing a compound of formula I and at least one of the components selected from a group consisting of pharmaceutically acceptable and pharmacologically compatible fillers, solvents, diluents, auxiliary, distributing and sensing agents, delivery agents, such as preservatives, stabilizers, disintegrators, moisteners, emulsifiers, suspending agents, thickeners, sweeteners, flavoring agents, aromatizing agents, antibacterial agents, fungicides, lubricants, and prolonged delivery controllers, the choice and proportions of which depend on the nature and method of prescription and dosage. Examples of suspending agents are ethoxylated isostearyl alcohol, polyoxyethene, sorbitol and sorbitol ester, microcrystalline cellulose, aluminum metahydroxide, bentonite, agar-agar and tragacanth, and also mixtures of these substances. Protection against the effect of microorganisms can be provided by various antibacterial and antifungal agents, such as, for example, parabens, chlorobutanol, sorbic acid, and similar compounds. The composition may also contain isotonic agents, such as, for example, sugar, sodium chloride, and similar compounds. A prolonged effect of the composition may be achieved by agents slowing absorption of the active ingredient, for example, aluminum monostearate and gelatine. Examples of suitable carriers, solvents, diluents and delivery agents include water, ethanol, polyalcohols, and their mixtures, vegetable oils (such as olive oil) and for injection-grade organic esters (such as ethyl oleate). Examples of fillers are lactose, milk sugar, sodium citrate, calcium carbonate, calcium phosphate and the like. Examples of disintegrators and distributors are starch, alginic acid and its salts, and silicates. Examples of lubricants are magnesium stearate, sodium lauryl sulfate, talc and high molecular weight polyethylene glycol. A pharmaceutical composition for peroral, sublingual, transdermal, intramuscular, intravenous, subcutaneous, local or rectal administration of the active ingredient, alone or in combination with another active ingredient, may be administered to humans and animals in a standard administration form, or in a mixture with traditional pharmaceutical carriers. Suitable standard administration forms include peroral forms, such as tablets, gelatin capsules, pills, powders, granules, chewing-gums, and peroral solutions or suspensions; sublingual and transbuccal administration forms; aerosols; implants; local, transdermal, subcutaneous, intramuscular, intravenous, intranasal or intraocular forms, and rectal administration forms.

"Pharmaceutically acceptable salt" means relatively non-toxic organic and inorganic salts of acids and bases claimed in this invention. The salts may be produced in situ during synthesis, separation or purification of compounds, or to be prepared purposefully. In particular, base salts may be prepared purposefully, starting from a purified free base of a claimed compound and a suitable organic or inorganic acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, mesylates, malonates, salicilates, propionates, ethane sulphonates, benzene sulfonates, sulfamates and the like (Detailed description of the properties of such salts is given in: Berge S. M., et al., "Pharmaceutical Salts" J. Pharm. Sci., 1977, 66: 1-19). Salts of the claimed acids may be also produced by reacting a purified acids specifically with a suitable base; in which case salts of metals and amines may be synthesized. Metal salts are salts of sodium, potassium, calcium, barium, zinc, magnesium, lithium, and aluminum, sodium and potassium salts being preferred. Suitable inorganic bases from which metal salts can be produced are sodium hydroxide, carbonate, bicarbonate and hydride; potassium hydroxide, carbonate and bicarbonate, lithium hydroxide, calcium hydroxide, magnesium hydroxide, and zinc hydroxide. Organic bases from which salts of the claimed acids can be obtained are amines and amino acids of sufficient basicity to produce a stable salt and suitable for use for medical purposes (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane, and the like. Besides, salts can be formed with the use of tetraalkylammonium hydroxides, such as choline, tetramethylammonium, tetraethylammonium, and the like. Amino acids may be selected from the main amino acids—lysine, ornithine, and agrinine.

"Focused library" is a combinatorial library or a combination of several combinatorial libraries, or a combination of libraries and compounds arranged in a special way to enhance the probability of finding hits and leaders or to improve the efficiency of their optimization. The design of focused libraries is, as a rule, associated with the directed search of effectors (inhibitors, activators, agonists, antagonists and so on) of definite biotargets (enzymes, receptors, ion channels, and so on).

"Fragment" (scaffold) means the structural formula of a molecule part characteristic of a group of compounds or a molecular framework typical of a group of compounds, or compounds in the "combinatorial library".

"1,2-Ethylene radical" means —CH$_2$—CH$_2$-group containing one or more "alkyl substituents" that may be identical or different, the values of which are defined in this section.

This invention is aimed at producing new antagonists of 5-HT$_6$ receptors that simultaneously regulate homeostasis of Ca$^{+2}$ ions in the cells.

The embodiment of the present invention relates to a method of antagonizing a 5-HT$_6$ serotonin receptor and simultaneously regulating Ca$^{+2}$ ion homeostasis in a cell, comprising administering to the cell a compound of formula 1, or a pharmaceutically acceptable salt thereof,

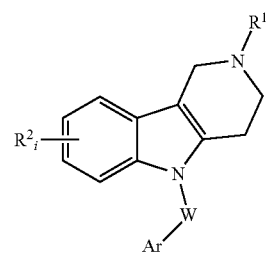

1 wherein: R$^1$ is a C$_1$-C$_5$ alkyl;

R$^2{}_i$ is independently hydrogen, halogen, a C$_1$-C$_3$ alkyl, CF$_3$, OCF$_3$ or OCH$_3$;

i is 1, 2, 3 or 4;

Ar is an unsubstituted phenyl or a substituted phenyl substituted with halogen, C$_1$-C$_6$ alkyl, C$_1$-C$_6$ alkoxy, substituted amino group or trifluoromethyl; or Ar is a substituted or unsubstituted 6-membered aromatic heterocycle with one or two nitrogen atoms in the heterocycle; and W is an ethylene group —CH$_2$—CH$_2$—, ethenyl group —CH=CH—, or ethynyl group —C≡C—.

The preferred antagonists of 5-HT$_6$ serotonin receptor are derivatives of 5-ethenyl-2,3,4,5-tetrahydro-1H-pyrido[4,3-b]indoles of the general formula 1.1

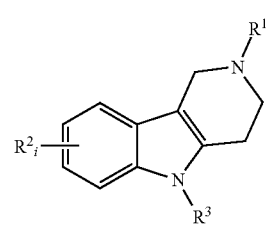

1.1 wherein:

R$^1$ and R$^2{}_i$ are as defined above;

R$^3$ represents Ar—CH=CH— group where Ar is as defined above.

The preferred antagonists are substituted cis-5-ethenyl-2,3,4,5-tetrahydro-1H-pyrido[4,3-b]indoles of the general formulas 1.1.1, 1.1.2 and substituted trans-5-ethenyl-2,3,4,5-tetrahydro-1H-pyrido[4,3-b]indoles of the general formulas 1.1.3, 1.1.4,

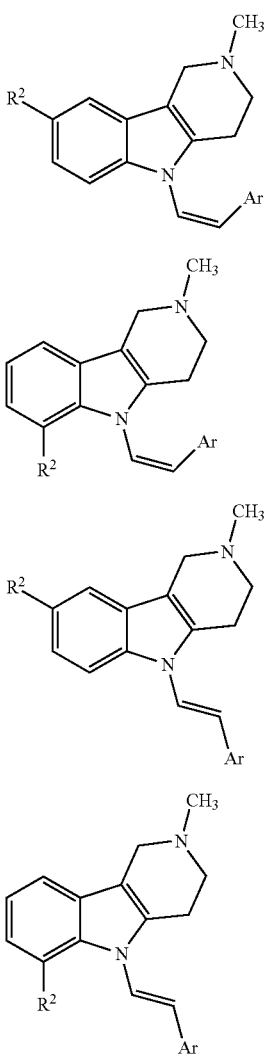

1.1.1

1.1.2

1.1.3

1.1.4 wherein:
R² is chosen from H, F, CH₃, CF₃, OCF₃;
Ar is as defined above.

The preferred antagonists of the general formulas 1.1 or pharmaceutically acceptable salts thereof are selected from the group consisting of cis-2-methyl-5-(2-phenylethenyl)-2,3,4,5-tetrahydro-1H-pyrido[4,3-b]indole 1.1(1), trans-2-methyl-5-(2-phenylethenyl)-2,3,4,5-tetrahydro-1H-pyrido[4,3-b]indole 1.1(2), trans-2-methyl-5-[2-(pyridin-4-yl)ethenyl]-2,3,4,5-tetrahydro-1H-pyrido[4,3-b]indole 1.1(3), cis-2-methyl-5-[2-(pyridin-3-yl)ethenyl]-2,3,4,5-tetrahydro-1H-pyrido[4,3-b]indole 1.1(4), trans-2-methyl-5-[2-(pyridin-2-yl)ethenyl]-2,3,4,5-tetrahydro-1H-pyrido[4,3-b]indole 1.1(5), cis-2-tert-butyl-5-[2-(pyridin-3-yl)ethenyl]-2,3,4,5-tetrahydro-1H-pyrido[4,3-b]indole 1.1(6), cis-2-methyl-5-(2-phenylethenyl)-8-fluoro-2,3,4,5-tetrahydro-1H-pyrido[4,3-b]indole 1.1.1(1), trans-2-methyl-5-(2-phenylethenyl)-8-fluoro-2,3,4,5-tetrahydro-1H-pyrido[4,3-b]indole 1.1.3(1), trans-2-methyl-5-[2-(pyridin-4-yl)ethenyl]-8-fluoro-2,3,4,5-tetrahydro-1H-pyrido[4,3-b]indole 1.1.3(2), cis-2-methyl-5-[2-(pyridin-3-yl)ethenyl]-8-fluoro-2,3,4,5-tetrahydro-1H-pyrido[4,3-b]indole 1.1.1(2), trans-2-methyl-5-[2-(pyridin-2-yl)ethenyl]-8-fluoro-2,3,4,5-tetrahydro-1H-pyrido[4,3-b]indole 1.1.3(3), cis-2,8-dimethyl-5-(2-phenylethenyl)-2,3,4,5-tetrahydro-1H-pyrido[4,3-b]indole 1.1.1(3), trans-2,8-dimethyl-5-(2-phenylethenyl)-2,3,4,5-tetrahydro-1H-pyrido[4,3-b]indole 1.1.3(4), cis-2,8-dimethyl-5-[2-(pyridin-3-yl)ethenyl]-2,3,4,5-tetrahydro-1H-pyrido[4,3-b]indole 1.1.1(4), trans-2,8-dimethyl-5-[2-(pyridin-4-yl)ethenyl]-2,3,4,5-tetrahydro-1H-pyrido[4,3-b]indole 1.1.3(5), cis-2-benzyl-5-[2-(pyridin-3-yl)ethenyl]-8-methyl-2,3,4,5-tetrahydro-1H-pyrido[4,3-b]indole 1.1.1(5), trans-2-methyl-5-[2-(4-fluorophenyl)ethenyl]-8-fluoro-2,3,4,5-tetrahydro-1H-pyrido[4,3-b]indole 1.1.3(6), cis-2-methyl-5-[2-(3-fluorophenyl)ethenyl]-8-fluoro-2,3,4,5-tetrahydro-1H-pyrido[4,3-b]indole 1.1.1(6), trans-2,8-dimethyl-5-[2-(4-trifluoromethylphenyl)ethenyl]-2,3,4,5-tetrahydro-1H-pyrido[4,3-b]indole 1.1.3(7), cis-2,8-dimethyl-5-[2-(3-trifluoromethylphenyl)ethenyl]-2,3,4,5-tetrahydro-1H-pyrido[4,3-b]indole 1.1.1(7), trans-2-methyl-5-[2-(4-trifluoromethylphenyl)ethenyl]-8-fluoro-2,3,4,5-tetrahydro-1H-pyrido[4,3-b]indole 1.1.3(8), cis-2-methyl-5-[2-(4-methoxyphenyl)ethenyl]-8-fluoro-2,3,4,5-tetrahydro-1H-pyrido[4,3-b]indole 1.1.1(8), cis-2-methyl-5-[2-(4-dimethylamino-phenyl)ethenyl]-8-fluoro-2,3,4,5-tetrahydro-1H-pyrido[4,3-b]indole 1.1.1(9), and trans-2,8-dimethyl-5-[2-(4-fluorophenyl)ethenyl]-2,3,4,5-tetrahydro-1H-pyrido[4,3-b]indole 1.1.3(9), corresponding to the structures shown below:

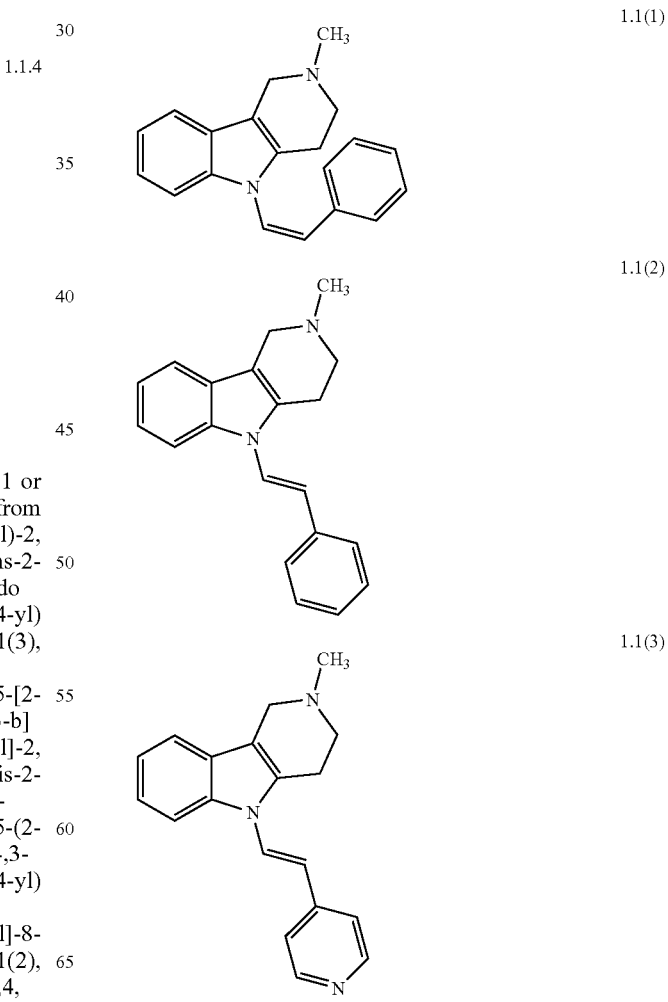

-continued
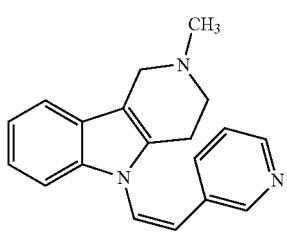
1.1(4)
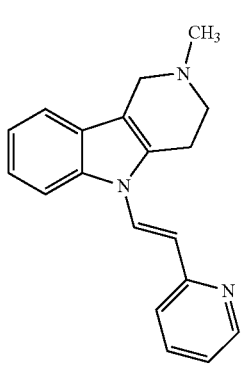
1.1(5)
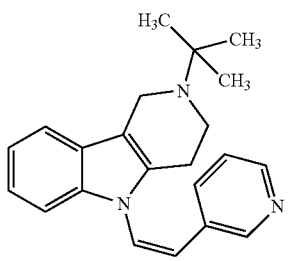
1.1(6)
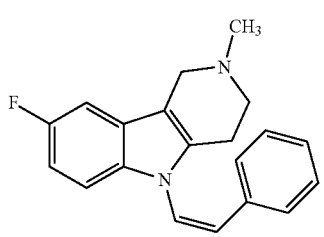
1.1.1(1)
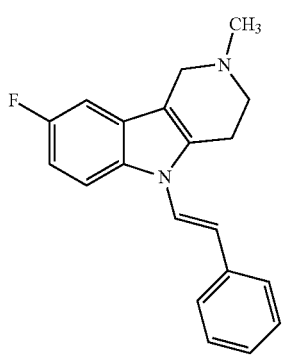
1.1.3(1)
-continued
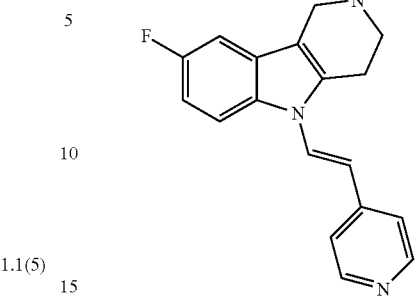
1.1.3(2)
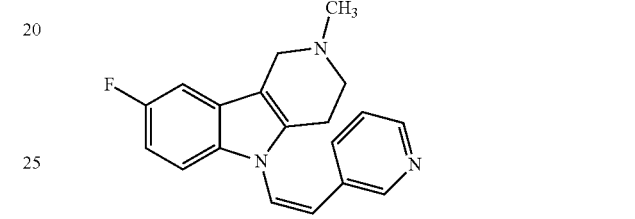
1.1.1(2)
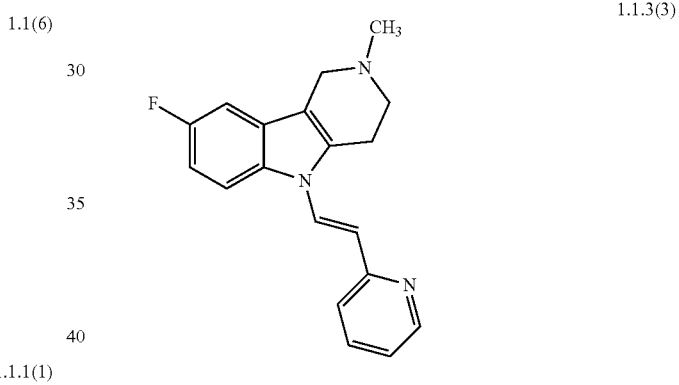
1.1.3(3)
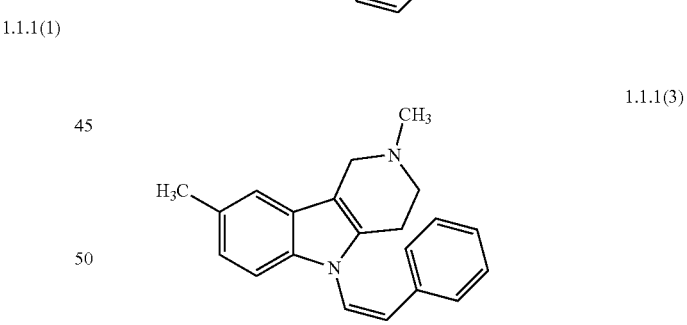
1.1.1(3)
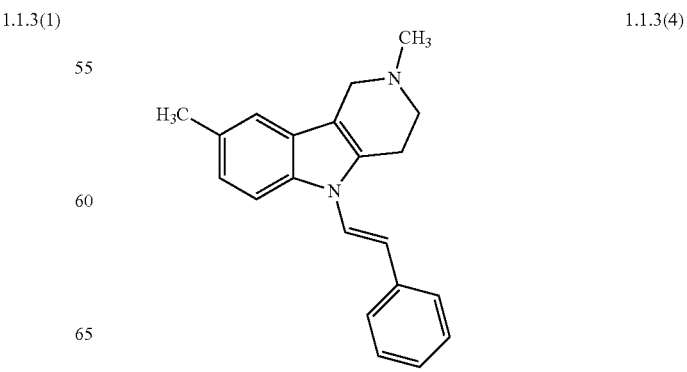
1.1.3(4)

-continued
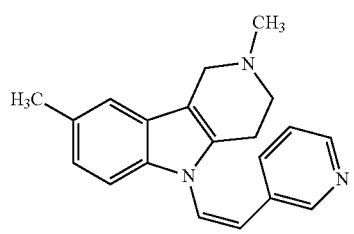
1.1.1(4)
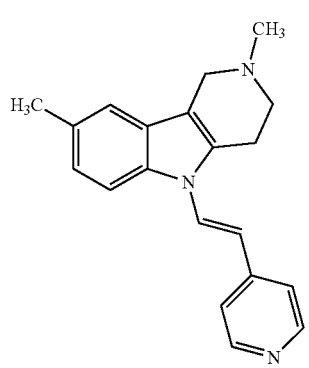
1.1.3(5)
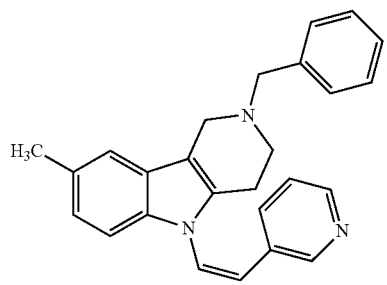
1.1.1(5)
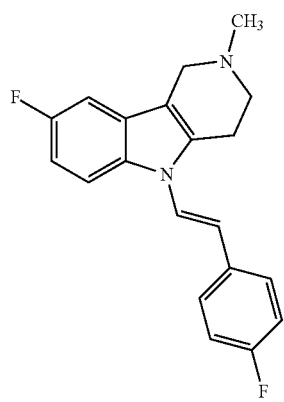
1.1.3(6)
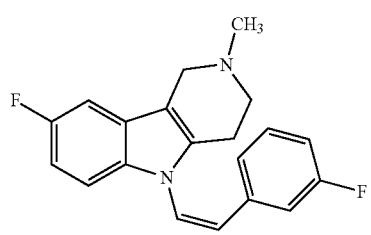
1.1.1(6)
-continued
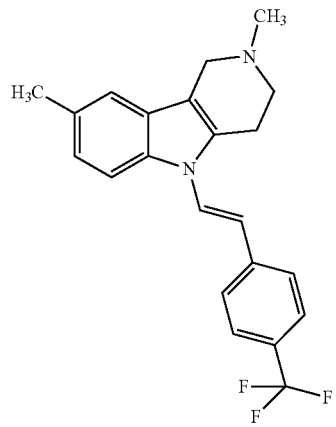
1.1.3(7)
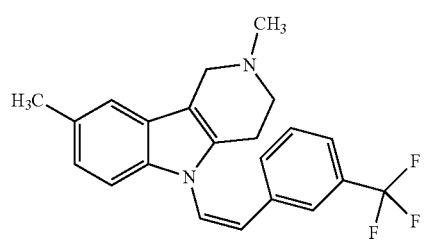
1.1.1(7)
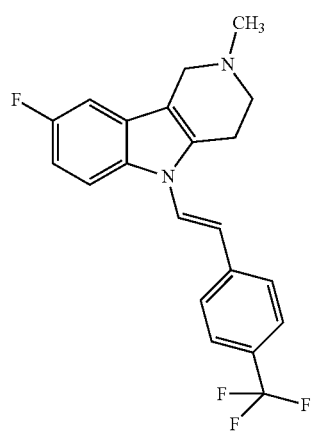
1.1.3(8)
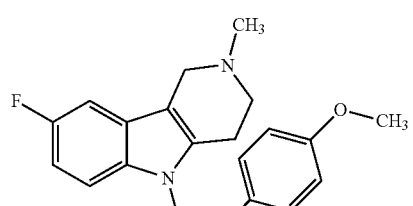
1.1.1(8)
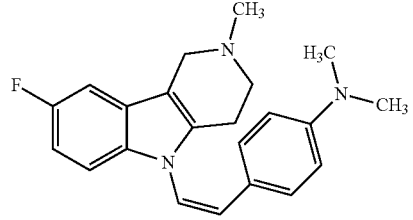
1.1.1(9)

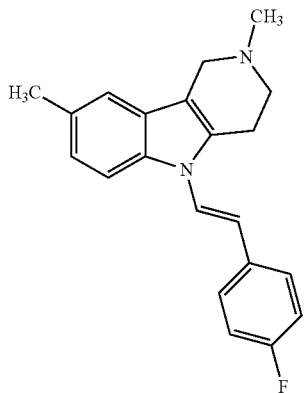

1.1.3(9)

The preferred antagonists are derivatives of 5-ethyl-2,3,4,5-tetrahydro-1H-pyrido[4,3-b]indoles of the general formula 1.2,

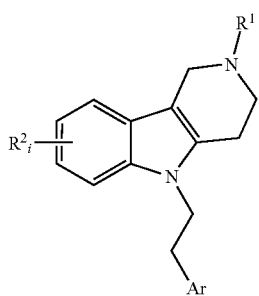

1.2 wherein:
R¹, R²ᵢ and Ar are as defined above.

The preferred antagonists are substituted 5-ethyl-2,3,4,5-tetrahydro-1H-pyrido[4,3-b]indoles of the general formulas 1.2.1, 1.2.2,

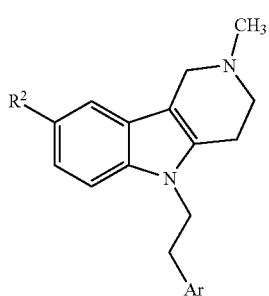

1.2.1

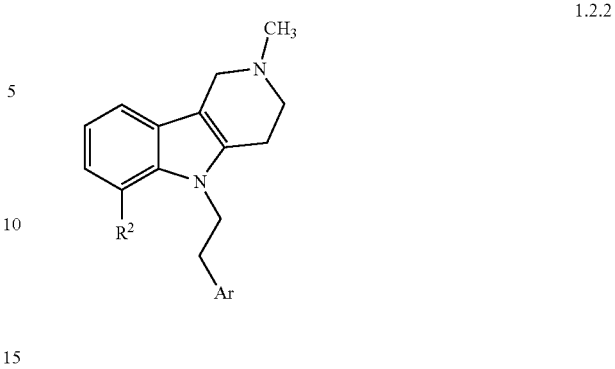

1.2.2 wherein:
R² is chosen from H, F, $CH_3$, $CF_3$, $OCF_3$;
Ar is as defined above.

The preferable antagonists of the general formula 1.2 or pharmaceutically acceptable salts thereof are selected from the group consisting of 2-methyl-5-(2-phenylethyl)-2,3,4,5-tetrahydro-1H-pyrido[4,3-b]indole 1.2(1), 2-methyl-5-[2-(pyridin-4-yl)ethyl]-2,3,4,5-tetrahydro-1H-pyrido[4,3-b]indole 1.2(2), 2-methyl-5-[2-(pyridin-3-yl)ethyl]-2,3,4,5-tetrahydro-1H-pyrido[4,3-b]indole 1.2(3), 2-methyl-5-[2-(pyridin-2-yl)ethyl]-2,3,4,5-tetrahydro-1H-pyrido[4,3-b]indole 1.2(4), 2-tert-butyl-5-[2-(pyridin-3-yl)ethyl]-2,3,4,5-tetrahydro-1H-pyrido[4,3-b]indole 1.2(5), 2-methyl-5-[2-(6-methylpyridin-3-yl)ethyl]-2,3,4,5-tetrahydro-1H-pyrido[4,3-b]indole 1.2(6), 2,8-dimethyl-5-(2-phenylethyl)-2,3,4,5-tetrahydro-1H-pyrido[4,3-b]indole 1.2.1(1), 2,8-dimethyl-5-[2-(pyridin-4-yl)ethyl]-2,3,4,5-tetrahydro-1H-pyrido[4,3-b]indole 1.2.1(2), 2,8-dimethyl-5-[2-(pyridin-3-yl)ethyl]-2,3,4,5-tetrahydro-1H-pyrido[4,3-b]indole 1.2.1(3), 2,8-dimethyl-5-[2-(pyridin-2-yl)ethyl]-2,3,4,5-tetrahydro-1H-pyrido[4,3-b]indole 1.2.1(4), 2,8-dimethyl-5-[2-(6-methylpyridin-3-yl)ethyl]-2,3,4,5-tetrahydro-1H-pyrido[4,3-b]indole 1.2.1(5), 2,8-dimethyl-5-[2-(pyrazin-2-yl)ethyl]-2,3,4,5-tetrahydro-1H-pyrido[4,3-b]indole 1.2.1(6), 2-methyl-5-(2-phenylethyl)-8-fluoro-2,3,4,5-tetrahydro-1H-pyrido[4,3-b]indole 1.2.1(7), 2-methyl-5-[2-(pyridin-4-yl)ethyl]-8-fluoro-2,3,4,5-tetrahydro-1H-pyrido[4,3-b]indole 1.2.1(8), 2-methyl-5-[2-(pyridin-3-yl)ethyl]-8-fluoro-2,3,4,5-tetrahydro-1H-pyrido[4,3-b]indole 1.2.1(9), 2-methyl-5-[2-(pyridin-2-yl)ethyl]-8-fluoro-2,3,4,5-tetrahydro-1H-pyrido[4,3-b]indole 1.2.1(10), 2-methyl-5-[2-(6-methylpyridin-3-yl)ethyl]-8-fluoro-2,3,4,5-tetrahydro-1H-pyrido[4,3-b]indole 1.2.1(11), 2-methyl-5-(2-phenylethyl)-8-trifluoromethyl-2,3,4,5-tetrahydro-1H-pyrido[4,3-b]indole 1.2.1(12), 2-methyl-5-[2-(pyridin-3-yl)ethyl]-8-trifluoromethyl-2,3,4,5-tetrahydro-1H-pyrido[4,3-b]indole 1.2.1(13), 2-methyl-5-(2-phenylethyl)-6-fluoro-2,3,4,5-tetrahydro-1H-pyrido[4,3-b]indole 1.2.2(1), 2-methyl-5-(2-phenylethyl)-6-trifluoromethyl-2,3,4,5-tetrahydro-1H-pyrido[4,3-b]indole 1.2.2(2), and 2-methyl-5-[2-(pyridin-3-yl)ethyl]-6-trifluoromethyl-2,3,4,5-tetrahydro-1H-pyrido[4,3-b]indole 1.2.2(3), corresponding to the structures shown below:

1.2(1)
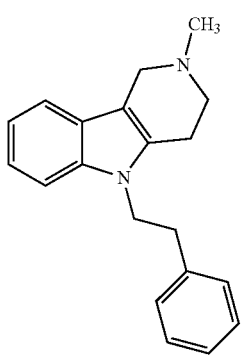
1.2(5)
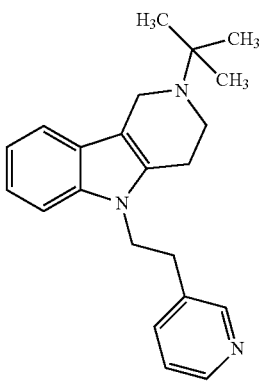
1.2(2)
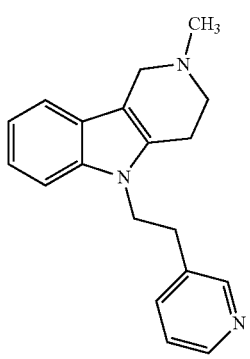
1.2(6)
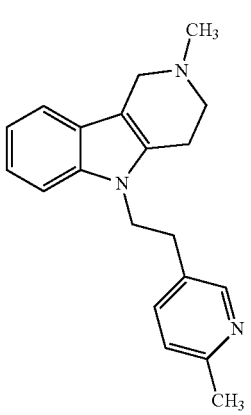
1.2(3)
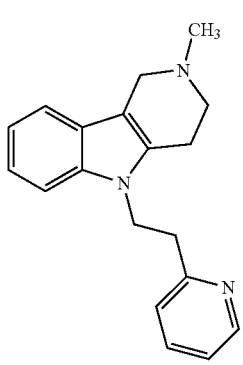
1.2.1(1)
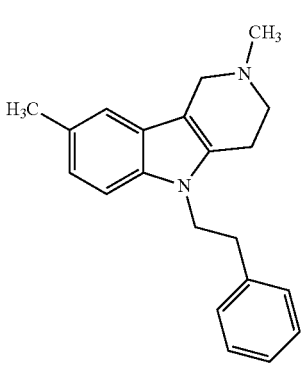
1.2(4)
1.2.1(2)

1.2.1(3)
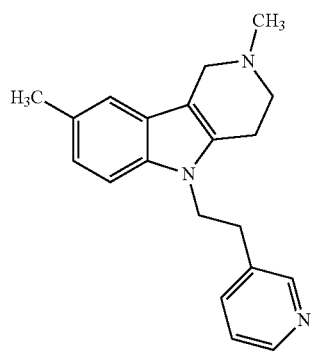
1.2.1(4)
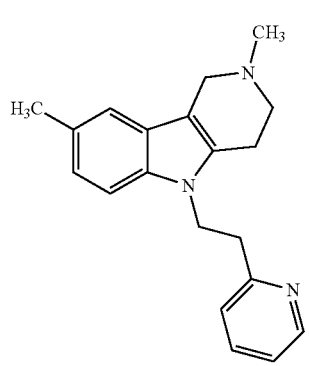
1.2.1(5)
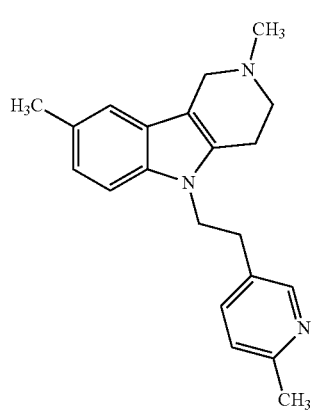
1.2.1(6)
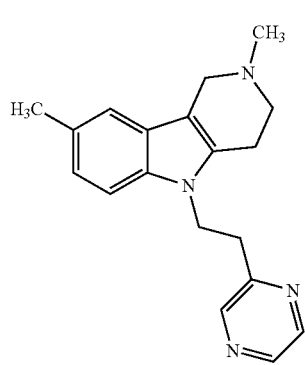
1.2.1(7)
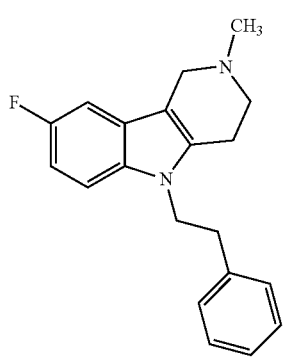
1.2.1(8)
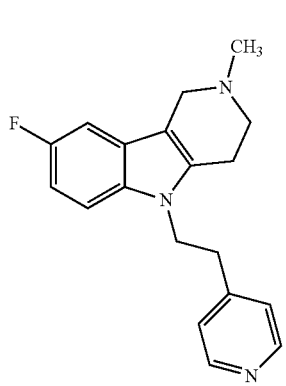
1.2.1(9)
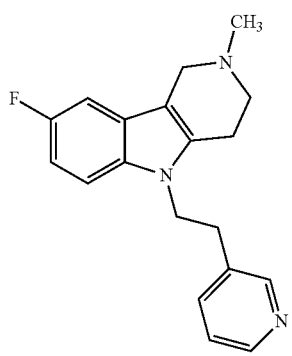
1.2.1(10)
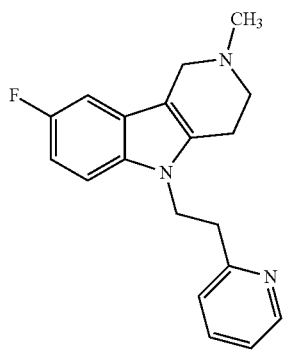

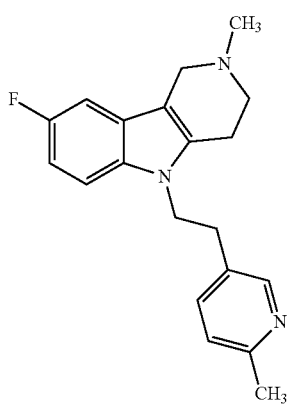 1.2.1(11)
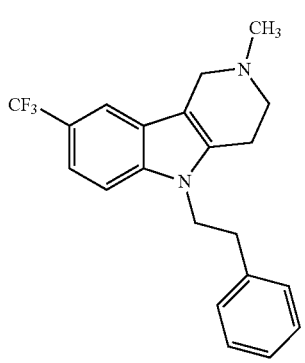 1.2.1(12)
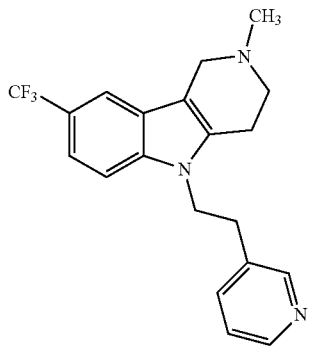 1.2.1(13)
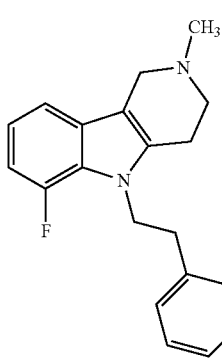 1.2.2(1)
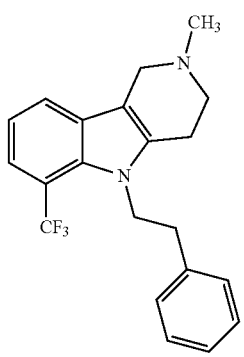 1.2.2(2)
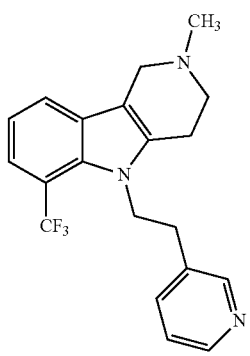 1.2.2(3)
The preferred antagonists are derivatives of 5-ethynyl-2,3,4,5-tetrahydro-1H-pyrido[4,3-b]indoles of the general formula 1.3,
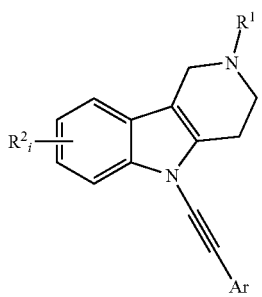 1.3
wherein:
R¹, R²$_i$ and Ar are as defined above.
The preferred antagonists are substituted 5-ethynyl-2,3,4,5-tetrahydro-1H-pyrido[4,3-b]indoles of the general formulas 1.3.1, 1.3.2,
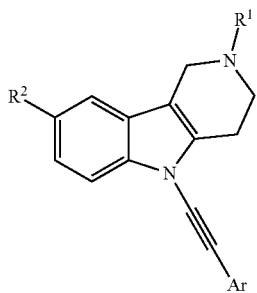 1.3.1

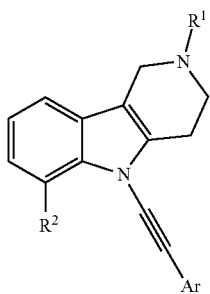

wherein:

$R^2$ is chosen from H, F, $CH_3$, $CF_3$, $OCF_3$;

$R^1$ and Ar are as defined above.

The preferred antagonists of the general formula 1.3 or the pharmaceutically acceptable salt thereof are selected from the group consisting of 2-methyl-5-phenylethynyl-2,3,4,5-tetrahydro-1H-pyrido[4,3-b]indole 1.3(1), 2-methyl-5-(pyridin-2-ylethynyl)-2,3,4,5-tetrahydro-1H-pyrido[4,3-b]indole 1.3(2), 2-methyl-5-(pyridin-3-ylethynyl)-2,3,4,5-tetrahydro-1H-pyrido[4,3-b]indole 1.3(3), 2-methyl-5-(pyridin-4-ylethynyl)-2,3,4,5-tetrahydro-1H-pyrido[4,3-b]indole 1.3(4), 2-methyl-5-(pyrimidin-5-ylethynyl)-2,3,4,5-tetrahydro-1H-pyrido[4,3-b]indole 1.3(5), 2-methyl-5-phenylethynyl-8-fluoro-2,3,4,5-tetrahydro-1H-pyrido[4,3-b]indole 1.3.1(1), 2-methyl-5-(pyridin-2-ylethynyl)-8-fluoro-2,3,4,5-tetrahydro-1H-pyrido[4,3-b]indole 1.3.1(2), 2-methyl-5-(pyridin-3-ylethynyl)-8-fluoro-2,3,4,5-tetrahydro-1H-pyrido[4,3-b]indole 1.3.1(3), 2-methyl-5-(pyridin-4-ylethynyl)-8-fluoro-2,3,4,5-tetrahydro-1H-pyrido[4,3-b]indole 1.3.1(4), 2-methyl-5-(pyridin-3-ylethynyl)-6-fluoro-2,3,4,5-tetrahydro-1H-pyrido[4,3-b]indole 1.3.2(1), 2,8-dimethyl-5-phenylethynyl-2,3,4,5-tetrahydro-1H-pyrido[4,3-b]indole 1.3.1(5), 2,8-dimethyl-5-(pyridin-2-ylethynyl)-2,3,4,5-tetrahydro-1H-pyrido[4,3-b]indole 1.3.1(6), 2,8-dimethyl-5-(pyridin-3-ylethynyl)-2,3,4,5-tetrahydro-1H-pyrido[4,3-b]indole 1.3.1(7), 2,8-dimethyl-5-(pyridin-4-ylethynyl)-2,3,4,5-tetrahydro-1H-pyrido[4,3-b]indole 1.3.1(8), 2-methyl-5-(pyridin-2-ylethynyl)-8-trifluoromethyl-2,3,4,5-tetrahydro-1H-pyrido[4,3-b]indole 1.3.1(9), 2-methyl-5-(4-methoxyphenylethynyl)-8-fluoro-2,3,4,5-tetrahydro-1H-pyrido[4,3-b]indole 1.3.1(10), 2-methyl-5-(4-fluorophenylethynyl)-8-fluoro-2,3,4,5-tetrahydro-1H-pyrido[4,3-b]indole 1.3.1(11), 2-methyl-5-(3-fluorophenylethynyl)-8-fluoro-2,3,4,5-tetrahydro-1H-pyrido[4,3-b]indole 1.3.1(12), 2-methyl-5-(4-trifluoromethylphenylethynyl)-8-fluoro-2,3,4,5-tetrahydro-1H-pyrido[4,3-b]indole 1.3.1(13), 2-methyl-5-(pyridin-3-ylethynyl)-8-trifluoromethyl-2,3,4,5-tetrahydro-1H-pyrido[4,3-b]indole 1.3.1(14), 2,8-dimethyl-5-(4-fluorophenylethynyl)-2,3,4,5-tetrahydro-1H-pyrido[4,3-b]indole 1.3.1(15), 2,8-dimethyl-5-(3-fluorophenylethynyl)-2,3,4,5-tetrahydro-1H-pyrido[4,3-b]indole 1.3.1(16), 2,8-dimethyl-5-(4-trifluoromethylphenylethynyl)-2,3,4,5-tetrahydro-1H-pyrido[4,3-b]indole 1.3.1(17), 2,8-dimethyl-5-(3-trifluoromethylphenyl-ethynyl)-2,3,4,5-tetrahydro-1H-pyrido[4,3-b]indole 1.3.1(18), 2,8-dimethyl-5-(2-trifluoromethylphenylethynyl)-2,3,4,5-tetrahydro-1H-pyrido[4,3-b]indole 1.3.1(19), 2,8-dimethyl-5-(2-fluorophenylethynyl)-2,3,4,5-tetrahydro-1H-pyrido[4,3-b]indole 1.3.1(20), 2,8-dimethyl-5-(4-methoxyphenylethynyl)-2,3,4,5-tetrahydro-1H-pyrido[4,3-b]indole 1.3.1(21), 2,8-dimethyl-5-(4-dimethylaminophenylethynyl)-2,3,4,5-tetrahydro-1H-pyrido[4,3-b]indole 1.3.1(22), 2,8-dimethyl-5-(3-methoxyphenylethynyl)-2,3,4,5-tetrahydro-1H-pyrido[4,3-b]indole 1.3.1(23), and 2,8-dimethyl-5-(2-methoxyphenylethynyl)-2,3,4,5-tetrahydro-1H-pyrido[4,3-b]indole 1.3.1(24), corresponding to the structures shown below:

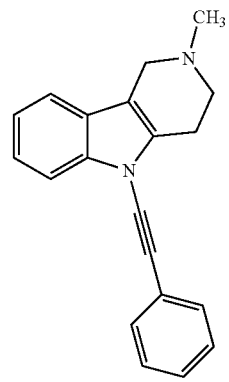

1.3(1)

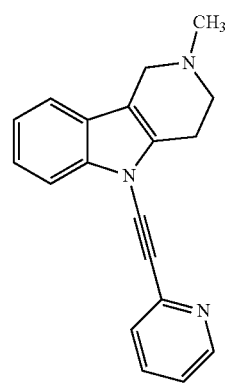

1.3(2)

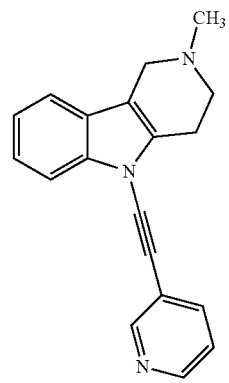

1.3(3)

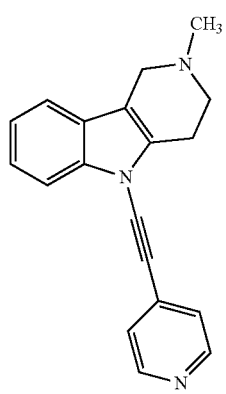 1.3(4)
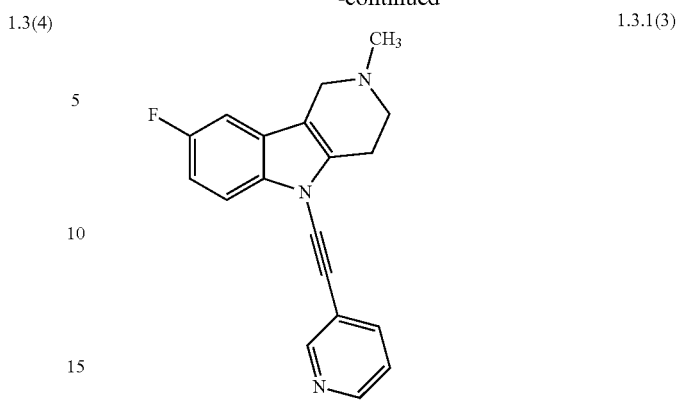 1.3.1(3)
1.3(5)
1.3.1(4)
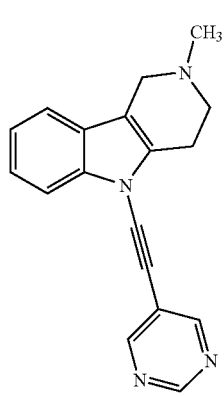 1.3.1(1)
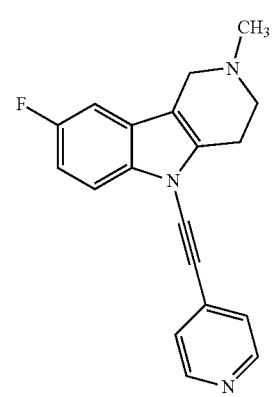 1.3.2(1)
1.3.1(2)
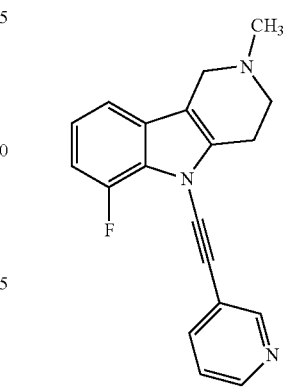
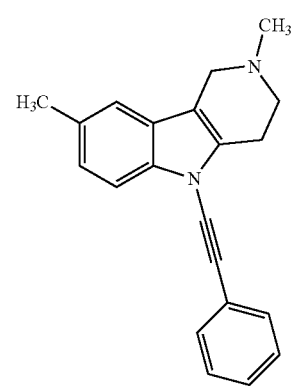 1.3.1(5)

1.3.1(6)
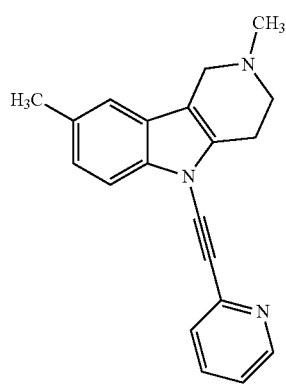
1.3.1(7)
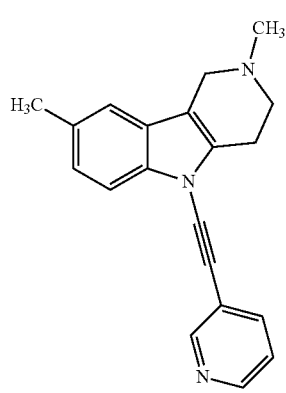
1.3.1(8)
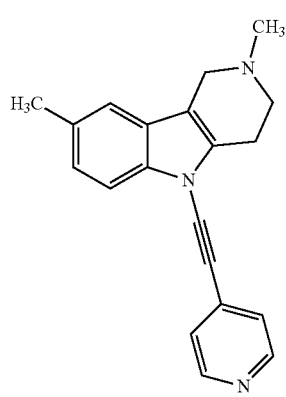
1.3.1(9)
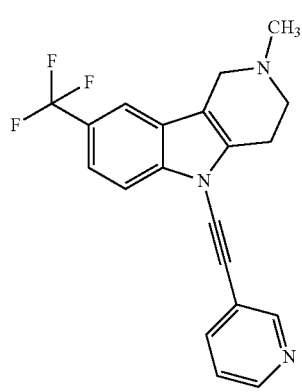
1.3.1(10)
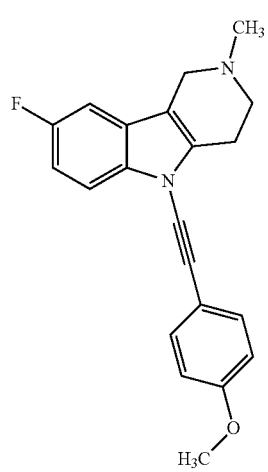
1.3.1(11)
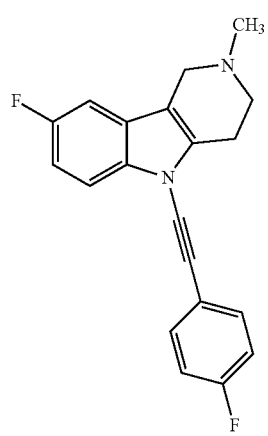
1.3.1(12)
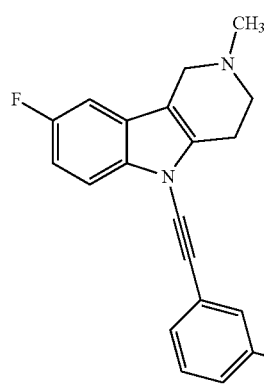

1.3.1(13)
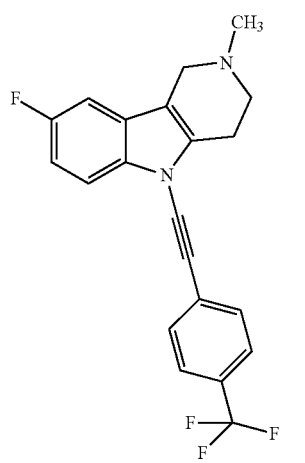
1.3.1(14)
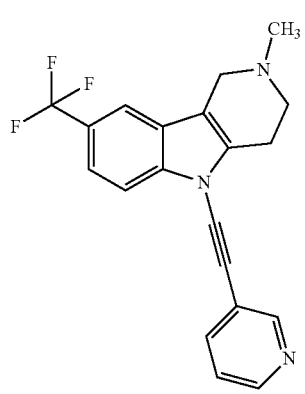
1.3.1(15)
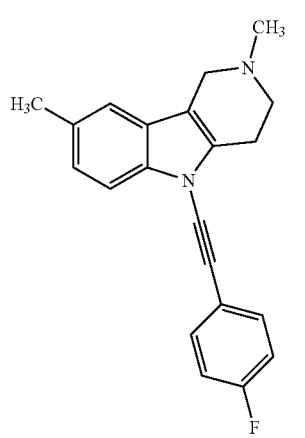
1.3.1(16)
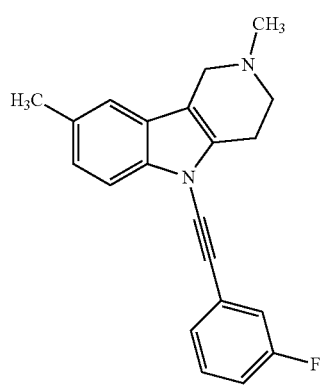
1.3.1(17)
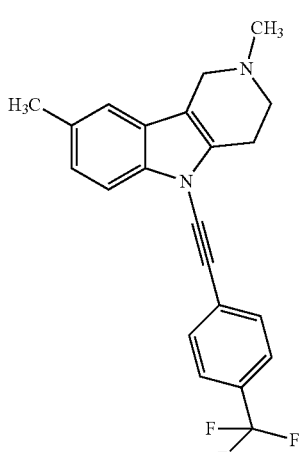
1.3.1(18)
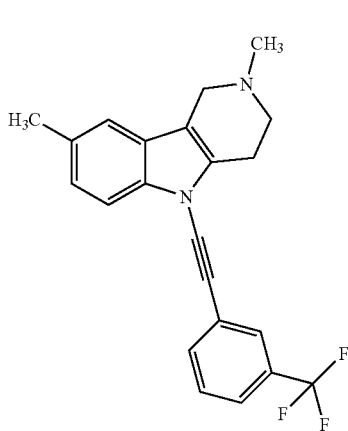
1.3.1(19)
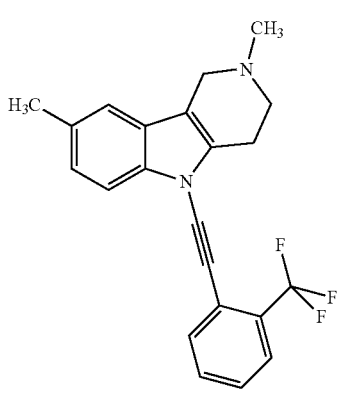
1.3.1(20)
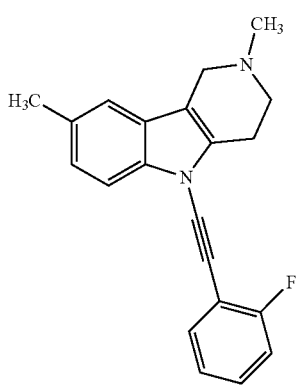

1.3.1(21)

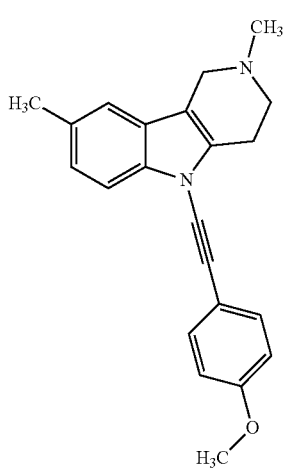

1.3.1(22)

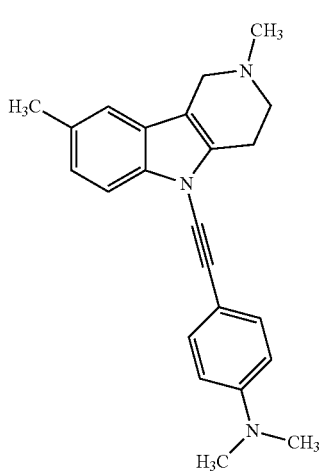

1.3.1(23)

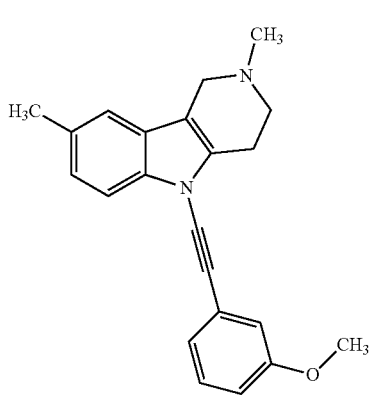

1.3.1(24)

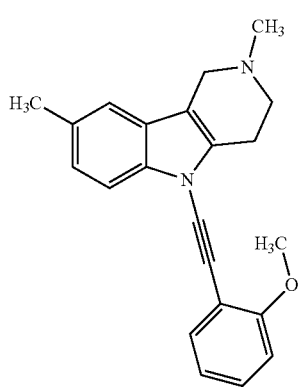

The purpose of the present invention is a new pharmaceutical composition, exhibiting properties of antagonist of 5-HT$_6$ receptors and modulators of Ca$^{+2}$ ions homeostasis in cells, for making medicines in various forms.

The object in view is achieved by the pharmaceutical composition comprising as an active substance an effective amount of at least one antagonist of 5-HT$_6$ receptors, chosen from substituted 2,3,4,5-tetrahydro-1H-pyrido[4,3-b]indoles of the general formula 1 or pharmaceutically acceptable salt and/or hydrate thereof.

The preferable pharmaceutical composition are the composition comprising as an active substance, at least, one substituted 5-[2-aryl(or azaheterocyclyl)ethenyl]-2,3,4,5-tetrahydro-1H-pyrido[4,3-b]indole of the general formula 1.1.

The preferable pharmaceutical composition is the composition comprising as an active substance, at least, one substituted 5-[2-aryl(or azaheterocyclyl)ethyl]-2,3,4,5-tetrahydro-1H-pyrido[4,3-b]indole of the general formula 1.2.

The preferable pharmaceutical composition is the composition comprising as an active substance, at least, one substituted 5-[2-aryl(or azaheterocyclyl)ethynyl]-2,3,4,5-tetrahydro-1H-pyrido[4,3-b]indole of the general formula 1.3.

Pharmaceutical compositions may include pharmaceutically acceptable excipients. Pharmaceutically acceptable excipients mean diluents, auxiliary agents and/or carriers applied in the sphere of pharmaceutics. According to the invention the pharmaceutical composition together with substituted 2,3,4,5-tetrahydro-1H-pyrido[4,3-b]indoles of the general formula 1 may include other active ingredients provided that they do not induce undesirable effects.

If required, according to the present invention, pharmaceutical compositions can be used in clinical practice in various forms prepared by mixing the compositions with traditional pharmaceutical carries, for example, peroral forms (such as, tablets, gelatinous capsules, pills, solutions or suspensions); forms for injections (such as, solutions or suspensions for injections, or a dry powder for injections which requires only addition of water for injections before utilization); local forms (such as, ointments or solutions).

The carriers used in pharmaceutical compositions, according to the present invention, include carriers which are applied in the sphere of pharmaceutics for preparation of the commonly used forms including: binding agents, greasing agents, disintegrators, solvents, diluents, stabilizers, suspending agents, colorless agents, taste flavors are used for peroral forms; antiseptic agents, solubilizers, stabilizers are used in forms for injections; base materials, diluents, greasing agents, antiseptic agents are used in local forms.

The purpose of the present invention is also the method for preparation of pharmaceutical compositions.

The object in view is achieved by combining at least one active substance as an antagonist of 5-HT6 receptors, chosen from substituted 2,3,4,5-tetrahydro-1H-pyrido[4,3-b]indoles of the general formula 1 or pharmaceutically acceptable salt and/or hydrate thereof with pharmaceutically acceptable carriers, diluents or excipients.

The subject of the invention is medicines in the form of a tablets, capsules or injections, placed in a pharmaceutically acceptable packing intended for the prophylaxis and treatment of cognitive disorders and neurodegenerative diseases, concerned with the $5\text{-HT}_6$ receptors and elevated intracellular concentration of $Ca^{+2}$ ions, which comprise effective amount of an antagonist selected from substituted 2,3,4,5-tetrahydro-1H-pyrido[4,3-b]indoles of the general formula 1 or pharmaceutically acceptable salts and/or hydrates thereof, with the exception of medicines intended for prophylaxis and treatment of Alzheimer's and Huntington's diseases comprising 2,8-dimethyl-5-[2-(6-methylpyridin-3-yl)ethyl]-2,3,4,5-tetrahydro-1H-pyrido[4,3-b]indole of the formula 1.2.1(5)HCl.

The preferable medicines are the medicines in the form of a tablets, capsules or injections placed in a pharmaceutically acceptable packing intended for the prophylaxis and treatment of Alzheimer's and Huntington's diseases, which comprise an effective amount of at least one antagonist of $5\text{-HT}_6$ receptors chosed from substituted 2,3,4,5-tetrahydro-1H-pyrido[4,3-b]indoles of the general formula 1 or pharmaceutically acceptable salts and/or hydrates thereof, with the exception of 2,8-dimethyl-5-[2-(6-methylpyridin-3-yl)ethyl]-2,3,4,5-terahydro-1H-pyrido[4,3-b]indole of the formula 1.2.1(5)HCl.

The preferable medicines are the medicines comprising 2,8-dimethyl-5-(2-phenylethyl)-2,3,4,5-tetrahydro-1H-pyrido[4,3-b]indole 1.2.1(1) as antagonist of $5\text{-HT}_6$ receptors.

The purpose of the present invention is also medicines in the form of tablets, capsules or injections placed in pharmaceutically acceptable packing intended for the prophylaxis and treatment of mental disorders and schizophrenia.

The object in view is achieved by medicines in the form of a tablets, capsules or injections placed in a pharmaceutically acceptable packing intended for the prophylaxis and treatment of mental disorders and schizophrenia, which comprise an effective amount of at least one antagonist of $5\text{-HT}_6$ receptors chosed from substituted 2,3,4,5-tetrahydro-1H-pyrido[4,3-b]indoles of the general formula 1 or pharmaceutically acceptable salts and/or hydrates thereof.

The preferable medicines are the medicines (antidepressants) intended for the prophylaxis and treatment of depressions which comprise effective amount of at least one $5\text{-HT}_6$ receptors antagonist chosed from substituted 2,3,4,5-tetrahydro-1H-pyrido[4,3-b]indoles of the general formula 1 or pharmaceutically acceptable salts and/or hydrates thereof.

The preferable medicines are antidepressants comprising effective amount of 2,8-dimethyl-5-(2-phenylethyl)-2,3,4,5-tetrahydro-1H-pyrido[4,3-b]indole 1.2.1(1) or pharmaceutically acceptable salts thereof as antagonist of $5\text{-HT}_6$ receptors.

The preferable medicines are the medicines (anxiolytics or tranquilizers) intended for the prophylaxis and treatment of anxious disorders which comprise effective amount of at least one antagonist of $5\text{-HT}_6$ receptors chosed from substituted 2,3,4,5-tetrahydro-1H-pyrido[4,3-b]indoles of the general formula 1 or pharmaceutically acceptable salts and/or hydrates thereof.

The preferable medicine is the anxiolytic (tranquilizer) comprising an effective amount of 2,8-dimethyl-5-[2-(6-methylpyridin-3-yl)ethyl]-2,3,4,5-tetrahydro-1H-pyrido[4,3-b]indole 1.2.1(5) or pharmaceutically acceptable salt thereof as antagonist of $5\text{-HT}_6$ receptors The preferable medicine is the anxiolytic (tranquilizer) comprising an effective amount of 2,8-dimethyl-5-(2-phenylethyl)-2,3,4,5-tetrahydro-1H-pyrido[4,3-b]indole 1.2.1 (1) or pharmaceutically acceptable salt thereof as antagonist of $5\text{-HT}_6$ receptors The preferable medicines are the medicines (nootropics) intended for the prophylaxis and treatment of hyperkinetic disorders, in particular, cognition enhancing, which comprise an effective amount of at least one antagonist of $5\text{-HT}_6$ receptors chosed from substituted 2,3,4,5-tetrahydro-1H-pyrido[4,3-b]indoles of the general formula 1 or pharmaceutically acceptable salts and/or hydrates thereof.

The more preferable medicine is the nootropic comprising an effective amount of 2,8-dimethyl-5-[2-(6-methylpyridin-3-yl)ethyl]-2,3,4,5-tetrahydro-1H-pyrido[4,3-b]indole 1.2.1 (5) or pharmaceutically acceptable salt thereof as antagonist of $5\text{-HT}_6$ receptors.

The preferable medicine is the nootropic comprising an effective amount of 2,8-dimethyl-5-(2-phenylethyl)-2,3,4,5-tetrahydro-1H-pyrido[4,3-b]indole 1.2.1(1) or pharmaceutically acceptable salt thereof as antagonist of $5\text{-HT}_6$ receptors.

The purpose of the present invention is also medicines in the form of tablets, capsules, injections placed in a pharmaceutically acceptable packing intended for the prophylaxis and treatment of obesity.

The subject of this invention is also therapeutic cocktails intended for the prophylaxis and treatment of various diseases, concerned with the $5\text{-HT}_6$ receptors and elevated intracellular concentration of $Ca^{+2}$ ions in humans and other mammals, which comprise medicines in the form of tablets, capsules or injections placed in a pharmaceutically acceptable packing on basis of pharmaceutical compositions comprising at least one substituted 2,3,4,5-tetrahydro-1H-pyrido[4,3,-b]indol of the general formula 1 or its pharmaceutically acceptable salt and/or hydrate as antagonist of serotonine $5\text{-HT}_6$ receptors.

Another subject of the invention is therapeutic cocktails intended for the prophylaxis and treatment of various diseases, patogenesis of which concerned with the elevated intracellular concentration of $Ca^{+2}$ ions, including neurological disorders, neuro-degenerative and cognitive disorders in humans and other mammals, among them the prophylaxis and treatment of Alzheimer's disease, Huntington's disease, psychotic disorders and schizophrenia, hypoxia, ischaemia, hypoglycemia, convulsions, brain injuries, latirism, amyotrophic lateral sclerosis, obesity and stroke, which comprise medicines in the form of tablets, capsules or injections placed in pharmaceutically acceptable packing on the basis of pharmaceutical compositions containing at least one substituted 2,3,4,5-tetrahydro-1H-pyrido[4,3,-b]indol of the general formula 1 or its pharmaceutically acceptable salt and/or hydrate as antagonist of serotonine $5\text{-HT}_6$ receptors.

The therapeutic cocktails intended for the prophylaxis and treatment of various diseases, pathogenesis of which is associated with the elevated intracellular concentration of $Ca^{+2}$ ions in humans and other mammals, including neurological disorders, neuro-degenerative and cognitive disorders in animals and people, among them for the prophylaxis and treatment of Alzheimer's disease, Huntington's disease, psychotic disorders and schizophrenia, hypoxia, ischaemia, hypoglycemia, convulsions, brain injuries, latirism, amyotrophic lateral sclerosis and stroke along with the medicines disclosed in the invention, may include other medicines, such as: non-steroidal anti-inflammatory drugs (Ortofen, Indometacin, Ibuprofen, etc.), inhibitors of acetylcholinesterase (Takrin, Amiridin, Fizostigmin, Arisept, Phenserine, etc.), estrogens (eg estradiol), NMDA-receptor antagonists (eg, Memantin, Neramexane); nootropic drugs (eg, Piracetam, Fenibut, etc.); AMRA receptor modulators (eg, Ampalex); antagonists of cannabinoid ST-1 receptors (for example, Rimonabant); monoaminooxidase MAO-B and/or MAO-A inhibitors (eg, Rasagiline); antiamiloidogen drugs (eg, Tramiprosate); substances lowering beta-amyloid neurotoxicity (eg, Indole-3-propionic acid), inhibitors of gamma- and/or beta-Sekretaza; agonists of M1 muscarine receptors (eg, Cevimeline); metals helatories (eg, Clioquinol); antagonists of GAMK (B) receptors (eg, CGP-36742); monoclonal antibodies (eg, Bapineuzumab); antioxidants; neurotrophic agents (eg, Tserebrolizin); antidepressants (eg, Imipramine, Sertralin etc.) and others.

Therapeutic cocktails for reducing extra weight and obesity treating along with medicines disclosed in the invention may also include other medicines such as: anorexic drugs (eg, Fepranon, Dezopimon, Mazindol), hormonal drugs (eg, Tireoidin), hypolipidemic drugs, such as fibrates (eg Fenofibrat), statines (eg, Lovastatin, Simvastatin, Pravastatin and Probukol), and also hypoglycemia drugs (sulfonylureas—for example, Butamid, Glibenklamid; biguanidines—for example, Buformin, Metmorfin), and drugs with other mechanism of action, such as antagonists of cannabinoid CB-1 receptors (Rimonabant), inhibitors of norepinephrine and serotonin reuptake (Sibutramine), inhibitors of enzymes of fatty acid synthesis (Orlistat), and others, along with antioxidants, food additives, etc.

According to the instant invention one of the embodiments is a method for treating a cognitive disorder or neurodegenerative disease, or obesity as well as various diseases and conditions, concerned with the 5-$HT_6$ receptors and elevated intracellular concentration of $Ca^{+2}$ ions in a subject in need thereof comprising administering an effective dose to the subject of a compound of formula 1, or a pharmaceutically acceptable salt thereof,

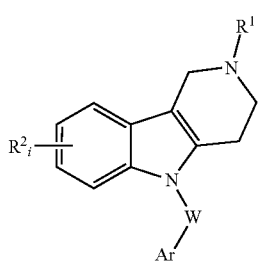

1 wherein: $R^1$ is a $C_1$-$C_5$ alkyl;
$R^2_i$ is independently hydrogen, halogen, a $C_1$-$C_3$ alkyl, $CF_3$, $OCF_3$ or $OCH_3$;
i is 1, 2, 3 or 4;
Ar is an unsubstituted phenyl or a substituted phenyl substituted with halogen, $C_1$-$C_6$ alkyl, $C_1$-$C_6$ alkoxy, substituted amino group or trifluoromethyl; or Ar is a substituted or unsubstituted 6-membered aromatic heterocycle with one or two nitrogen atoms in the heterocycle; and W is an ethylene group —$CH_2$—$CH_2$—, ethenyl group —CH═CH—, or ethynyl group —C≡C—.

The medicines could be administered perorally or parenterally (for example, intravenously, subcutaneously, intraperitoneally or locally). The clinical dosage of the antagonists of the general formula 1 could be corrected depending on: therapeutic efficiency and bioavailability of the active substances in an organism, rate of their exchange and deducing from organism, and depending on the age, sex and the severity of the patient's symptoms; the daily dosage for adults falls within the range of about 10 to about 500 mg of the active substance, preferably of about 50 to about 300 mg. Therefore, according to the present invention during the preparation of pharmaceutical compositions as units of dosage it is necessary to keep in mind the above effective dosage, so that each unit of dosage should contain of about 10 to about 500 mg of substituted 2,3,4,5-tetrahydro-1H-pyrido[4,3-b]indole of the general formula 1, preferably 50~300 mg. In accordance with the recommendation of a physician or pharmacist the above dosage can be taken several times during the definite time intervals (preferably—from one to six times).

The purpose of the present invention is novel substituted 2,3,4,5-tetrahydro-1H-pyrido[4,3-b]indoles possessing biological activity.

The object in view is achieved by substituted 2,3,4,5-tetrahydro-1H-pyrido[4,3-b]indoles of the general formula 1, pharmaceutically acceptable salts and/or hydrates thereof,

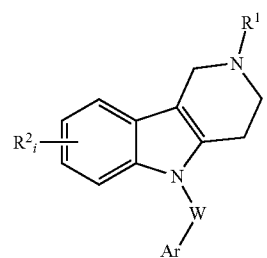

1 wherein:
$R^1$ is chosen from optionally substituted $C_1$-$C_5$ alkyls;
$R^2_i$ represents one or few equal or different substituents chosen from hydrogen, halogen, $C_1$-$C_3$ alkyl, $CF_3$ or $CF_3O$;
Ar represents unsubstituted phenyl or phenyl substituted by halogen, $C_1$-$C_6$ alkyl, $C_1$-$C_6$ alkoxy, optionally modified amino-group or $CF_3$; or optionally substituted 6-membered aromatic heterocycle containing 1 or 2 nitrogen atom in the cycle;
W represents ethylene group —$CH_2$—$CH_2$—, ethenyl group —CH═CH— or ethynyl group —C≡C—;
with the exception of: 2-methyl-5-phenethyl-2,3,4,5-tetrahydro-1H-pyrido[4,3-b]indole, 2-methyl-5-[2-(pyridin-2-yl)ethyl)]-2,3,4,5-tetrahydro-1H-pyrido[4,3-b]indole, 2-propyl-5-[2-(pyridin-2-yl)ethyl)]-2,3,4,5-tetrahydro-1H-pyrido[4,3-b]indole, 2-butyl-5-[2-(pyridin-2-yl)ethyl)]-2,3,4,5-tetrahydro-1H-pyrido[4,3-b]indole, 2-propyl-5-[2-(pyridin-4-yl)ethyl)]-2,3,4,5-tetrahydro-1H-pyrido[4,3-b]indole, 2-butyl-5-[2-(pyridin-4-yl)ethyl)]-2,3,4,5-tetrahydro-1H-pyrido[4,3-b]indole, 2-methyl-5-[2-(pyridin-4-yl)ethyl)]-2,3,4,5-tetrahydro-1H-pyrido[4,3-b]indole, 2-methyl-7-chloro-5-[2-(pyridin-4-yl)ethyl)]-2,3,4,5-tetrahydro-1H-pyrido[4,3-b]indole, 2-methyl-8-chloro-5-[2-(pyridin-4-yl)ethyl)]-2,3,4,5-tetrahydro-1H-pyrido[4,3-b]indole, 2,7- dimethyl-5-[2-(pyridin-4-yl)ethyl)]-2,3,4,5-tetrahydro-1H-pyrido[4,3-b]indole, 2,6-dimethyl-5-[2-(pyridin-4-yl)ethyl)]-2,3,4,5-tetrahydro-1H-pyrido[4,3-b]indole, 2,7,8-trimethyl-5-[2-(pyridin-4-yl)ethyl)]-2,3,4,5-tetrahydro-1H-pyrido[4,3-b]indole, 2,8,9-trimethyl-5-[2-(pyridin-4-yl)ethyl)]-2,3,4,5-tetrahydro-1H-pyrido[4,3-b]indole, 8-chloro-2-phenetyl-5-[2-(pyridin-4-yl)ethyl)]-2,3,4,5-tetrahydro-1H-pyrido[4,3-b]indole, 2,8-dimethyl-5-[2-(pyridin-4-yl)ethyl)]-2,3,4,5-tetrahydro-1H-pyrido[4,3-b]indole, 2-methyl-8-trifluoromethyl-5-[2-(pyridin-4-yl)ethyl)]-2,3,4,5-tetrahydro-1H-pyrido[4,3-b]indole, 2-methyl-8-carboxy-5-[2-(pyridin-4-yl)ethyl)]-2,3,4,5-tetrahydro-1H-pyrido[4,3-b]indole, 2-methyl-8-ethyloxycarbonyl-5-[2-(pyridin-4-yl)ethyl)]-2,3,4,5-tetrahydro-1H-pyrido[4,3-b]indole, 2-methyl-5-[2-(6-methylpyridin-3-yl)ethyl]-2,3,4,5-tetrahydro-1H-pyrido[4,3-b]indole, 8-methyl-5-[2-(6-methylpyridin-3-yl)ethyl]-2,3,4,5-tetrahydro-1H-pyrido[4,3-b]indole, 2-$C_1$-$C_5$ alkyl-5-[2-(6-methylpyridin-3-yl)ethyl]-2,3,4,5-tetrahydro-1H-pyrido[4,3-b]indoles, 2-$C_1$-$C_5$ alkyl-8-methyl-5-[2-(6-methylpyridin-3-yl)ethyl]-2,3,4,5-tetrahydro-1H-pyrido[4,3-b]indoles, 2-benzyl-5-[2-(6-methylpyridin-3-yl)ethyl]-2,3,4,5-tetrahydro-1H-pyrido[4,3-b]indole, 2-benzyl-8-chloro-5-[2-(6-methylpyridin-3-yl)ethyl]-2,3,4,5-tetrahydro-1H-pyrido[4,3-b]indole, 2-benzyl-8-methyl-5-[2-(6-methylpyridin-3-yl)ethyl]-2,3,4,5-tetrahydro-1H-pyrido[4,3-b]indole, 2,7-dimethyl-5-[2-(6-methylpyridin-3-yl)ethyl]-2,3,4,5-tetrahydro-1H-pyrido[4,3-b]indole, 7-chloro-2-methyl-5-[2-(6-methylpyridin-3-yl)ethyl]-2,3,4,5-tetrahydro-1H-pyrido[4,3-b]indole, 2-methyl-7-trifluoromethyl-5-[2-(6-methylpyridin-3-yl)ethyl]-2,3,4,5-tetrahydro-1H-pyrido[4,3-b]indole, 2,8-dimethyl-5-[2-(6-methylpyridin-3-yl)ethyl]-2,3,4,5-tetrahydro-1H-pyrido[4,3-b]indole, 8-bromo-2-methyl-5-[2-(6-methylpyridin-3-yl)ethyl]-2,3,4,5-tetrahydro-1H-pyrido[4,3-b]indole, 8-chloro-2-methyl-5-[2-(6-methylpyridin-3-yl)ethyl]-2,3,4,5-tetrahydro-1H-pyrido[4,3-b]indole, 2-methyl-8-trifluoromethyl-5-[2-(6-methylpyridin-3-yl)ethyl]-2,3,4,5-tetrahydro-1H-pyrido[4,3-b]indole, 8-chloro-2,6-dimethyl-5-[2-(6-methylpyridin-3-yl)ethyl]-2,3,4,5-tetrahydro-1H-pyrido[4,3-b]indole, 2,7,8-trimethyl-5-[2-(6-methylpyridin-3-yl)ethyl]-2,3,4,5-tetrahydro-1H-pyrido[4,3-b]indole, 7,8-dichloro-2-methyl-5-[2-(6-methylpyridin-3-yl)ethyl]-2,3,4,5-tetrahydro-1H-pyrido[4,3-b]indole, 7-chloro-2,8-dimethyl-5-[2-(6-methylpyridin-3-yl)ethyl]-2,3,4,5-tetrahydro-1H-pyrido[4,3-b]indole, 8-chloro-2,7-dimethyl-5-[2-(6-methylpyridin-3-yl)ethyl]-2,3,4,5-tetrahydro-1H-pyrido[4,3-b]indole, 2,8,9-trimethyl-5-[2-(6-methylpyridin-3-yl)ethyl]-2,3,4,5-tetrahydro-1H-pyrido[4,3-b]indole, 8-chloro-2-methyl-5-[2-(pyridin-3-yl)ethyl]-2,3,4,5-tetrahydro-1H-pyrido[4,3-b]indole and 2-methyl-5-[2-(2-methylpyridin-3-yl)ethyl]-2,3,4,5-tetrahydro-1H-pyrido[4,3-b]indole, or a pharmaceutically acceptable salt thereof.

The more preferred pyrido[4,3-b]indoles are derivatives of 5-ethenyl-2,3,4,5-tetrahydro-1H-pyrido[4,3-b]indoles of the general formula 1.1,

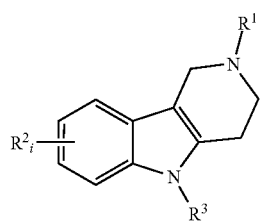

1.1 wherein:
$R^1$ and $R^2_i$ are as defined above;
$R^3$ represents a group —CH=CH—Ar, where Ar is as defined above.

The more preferred pyrido[4,3-b]indoles are substituted cis-5-ethenyl-2,3,4,5-tetrahydro-1H-pyrido[4,3-b]indoles of the general formulas 1.1.1, 1.1.2 and substituted trans-5-ethenyl-2,3,4,5-tetrahydro-1H-pyrido[4,3-b]indoles of the general formulas 1.1.3, 1.1.4,

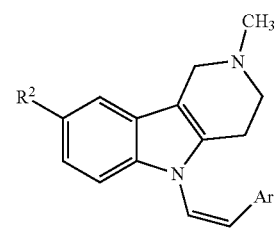

1.1.1

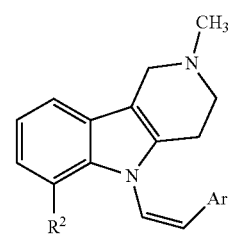

1.1.2

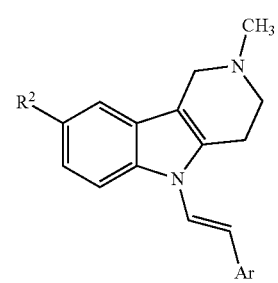

1.1.3

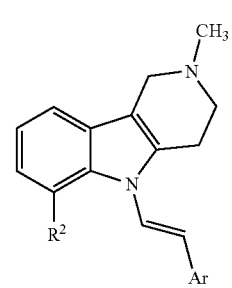

1.1.4 wherein:
$R^2$ is chosen from H, F, $CH_3$, $CF_3$;
Ar is as defined above.

The more preferred pyrido[4,3-b]indoles of the general formulas 1.1 or the pharmaceutically acceptable salt thereof are selected from the group consisting of cis-2-methyl-5-(2-phenylethenyl)-2,3,4,5-tetrahydro-1H-pyrido[4,3-b]indole 1.1(1), trans-2-methyl-5-(2-phenylethenyl)-2,3,4,5-tetrahydro-1H-pyrido[4,3-b]indole 1.1(2), trans-2-methyl-5-[2-(pyridin-4-yl)ethenyl]-2,3,4,5-tetrahydro-1H-pyrido[4,3-b]indole 1.1(3), cis-2-methyl-5-[2-(pyridin-3-yl)ethenyl]-2,3,4,5-tetrahydro-1H-pyrido[4,3-b]indole 1.1(4), trans-2-methyl-5-[2-(pyridin-2-yl)ethenyl]-2,3,4,5-tetrahydro-1H-pyrido[4,3-b]indole 1.1(5), cis-2-tert-butyl-5-[2-(pyridin-3-yl)ethenyl]-2,3,4,5-tetrahydro-1H-pyrido[4,3-b]indole 1.1(6), cis-2-methyl-5-(2-phenylethenyl)-8-fluoro-2,3,4,5-tetrahydro-1H-pyrido[4,3-b]indole 1.1.1(1), trans-2-methyl-5-(2-phenylethenyl)-8-fluoro-2,3,4,5-tetrahydro-1H-pyrido[4,3-b]indole 1.1.3(1), trans-2-methyl-5-[2-(pyridin-4-yl)ethenyl]-8-fluoro-2,3,4,5-tetrahydro-1H-pyrido[4,3-b]indole 1.1.3(2), cis-2-methyl-5-[2-(pyridin-3-yl)ethenyl]-8-fluoro-2,3,4,5-tetrahydro-1H-pyrido[4,3-b]indole 1.1.1(2), trans-2-methyl-5-[2-(pyridin-2-yl)ethenyl]-8-fluoro-2,3,4,5-tetrahydro-1H-pyrido[4,3-b]indole 1.1.3(3), cis-2,8-dimethyl-5-(2-phenylethenyl)-2,3,4,5-tetrahydro-1H-pyrido[4,3-b]indole 1.1.1(3), trans-2,8-dimethyl-5-(2-phenylethenyl)-2,3,4,5-tetrahydro-1H-pyrido[4,3-b]indole 1.1.3(4), cis-2,8-dimethyl-5-[2-(pyridin-3-yl)ethenyl]-2,3,4,5-tetrahydro-1H-pyrido[4,3-b]indole 1.1.1(4), trans-2,8-dimethyl-5-[2-(pyridin-4-yl)ethenyl]-2,3,4,5-tetrahydro-1H-pyrido[4,3-b]indole 1.1.3(5), cis-2-benzyl-5-[2-(pyridin-3-yl)ethenyl]-8-methyl-2,3,4,5-tetrahydro-1H-pyrido[4,3-b]indole 1.1.1(5), trans-2-methyl-5-[2-(4-fluorophenyl)ethenyl]-8-fluoro-2,3,4,5-tetrahydro-1H-pyrido[4,3-b]indole 1.1.3(6), cis-2-methyl-5-[2-(3-fluorophenyl)ethenyl]-8-fluoro-2,3,4,5-tetrahydro-1H-pyrido[4,3-b]indole 1.1.1(6), trans-2,8-dimethyl-5-[2-(4-trifluoromethylphenyl)ethenyl]-2,3,4,5-tetrahydro-1H-pyrido[4,3-b]indole 1.1.3(7), cis-2,8-dimethyl-5-[2-(3-trifluoromethylphenyl)ethenyl]-2,3,4,5-tetrahydro-1H-pyrido[4,3-b]indole 1.1.1(7), trans-2-methyl-5-[2-(4-trifluoromethylphenyl)ethenyl]-8-fluoro-2,3,4,5-tetrahydro-1H-pyrido[4,3-b]indole 1.1.3(8), cis-2-methyl-5-[2-(4-methoxyphenyl)ethenyl]-8-fluoro-2,3,4,5-tetrahydro-1H-pyrido[4,3-b]indole 1.1.1(8), cis-2-methyl-5-[2-(4-dimethylamino-phenyl)ethenyl]-8-fluoro-2,3,4,5-tetrahydro-1H-pyrido[4,3-b]indole 1.1.1(9), and trans-2,8-dimethyl-5-[2-(4-fluorophenyl)ethenyl]-2,3,4,5-tetrahydro-1H-pyrido[4,3-b]indole 1.1.3(9).

The more preferred pyrido[4,3-b]indoles are derivatives of 5-ethyl-2,3,4,5-tetrahydro-1H-pyrido[4,3-b]indoles of the general formula 1.2,

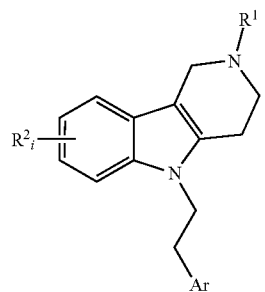

1.2 wherein:
$R^1$, $R^2_i$ and Ar are as defined above.

The more preferred pyrido[4,3-b]indoles are substituted 5-ethyl-2,3,4,5-tetrahydro-1H-pyrido[4,3-b]indoles of the general formulas 1.2.1, 1.2.2,

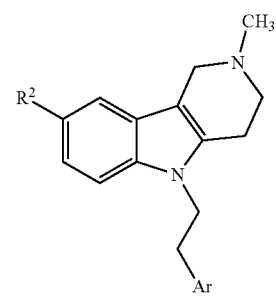

1.2.1

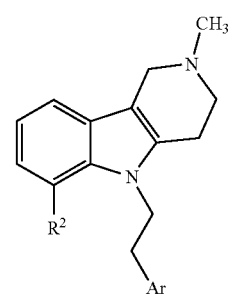

1.2.2 wherein:
$R^2$ is chosen from H, F, $CH_3$, $CF_3$, $OCF_3$;
Ar is as defined above.

The more preferred pyrido[4,3-b]indoles of the general formula 1.2 or pharmaceutically acceptable salts thereof are selected from the group consisting of 2,8-dimethyl-5-(2-phenylethyl)-2,3,4,5-tetrahydro-1H-pyrido[4,3-b]indole 1.2.1(1), 2,8-dimethyl-5-[2-(pyridin-2-yl)ethyl]-2,3,4,5-tetrahydro-1H-pyrido[4,3-b]indole 1.2.1(4), 2,8-dimethyl-5-[2-(pyrazin-2-yl)ethyl]-2,3,4,5-tetrahydro-1H-pyrido[4,3-b]indole 1.2.1(6), 2-methyl-5-(2-phenylethyl)-8-fluoro-2,3,4,5-tetrahydro-1H-pyrido[4,3-b]indole 1.2.1(7), 2-methyl-5-[2-(pyridin-4-yl)ethyl]-8-fluoro-2,3,4,5-tetrahydro-1H-pyrido[4,3-b]indole 1.2.1(8), 2-methyl-5-[2-(pyridin-3-yl)ethyl]-8-fluoro-2,3,4,5-tetrahydro-1H-pyrido[4,3-b]indole 1.2.1(9), 2-methyl-5-[2-(pyridin-2-yl)ethyl]-8-fluoro-2,3,4,5-tetrahydro-1H-pyrido[4,3-b]indole 1.2.1(10), 2-methyl-5-[2-(6-methylpyridin-3-yl)ethyl]-8-fluoro-2,3,4,5-tetrahydro-1H-pyrido[4,3-b]indole 1.2.1(11), 2-methyl-5-(2-phenylethyl)-8-trifluoromethyl-2,3,4,5-tetrahydro-1H-pyrido[4,3-b]indole 1.2.1(12), 2-methyl-5-[2-(pyridin-3-yl)ethyl]-8-trifluoromethyl-2,3,4,5-tetrahydro-1H-pyrido[4,3-b]indole 1.2.1(13), 2-methyl-5-(2-phenylethyl)-6-fluoro-2,3,4,5-tetrahydro-1H-pyrido[4,3-b]indole 1.2.2(1), 2-methyl-5-(2-phenylethyl)-6-trifluoromethyl-2,3,4,5-tetrahydro-1H-pyrido[4,3-b]indole 1.2.2(2), and 2-methyl-5-[2-(pyridin-3-yl)ethyl]-6-trifluoromethyl-2,3,4,5-tetrahydro-1H-pyrido[4,3-b]indole 1.2.2(3).

The more preferred pyrido[4,3-b]indoles are derivatives of 5-ethynyl-2,3,4,5-tetrahydro-1H-pyrido[4,3-b]indoles of the general formula 1.3,

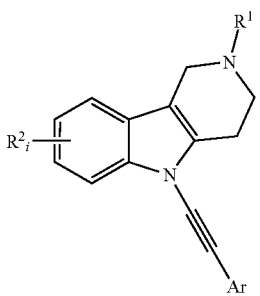

wherein:

$R^1$, $R^2_i$ and Ar are as defined above.

The more preferred pyrido[4,3-b]indoles are substituted 5-ethynyl-2,3,4,5-tetrahydro-1H-pyrido[4,3-b]indoles of the general formulas 1.3.1, 1.3.2,

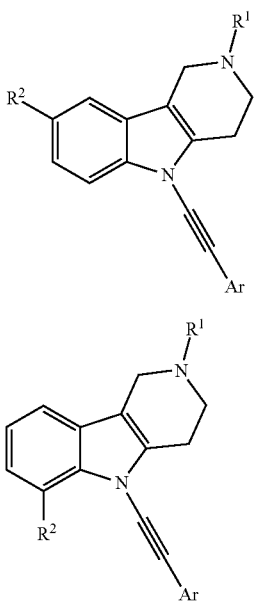

wherein:

$R^2$ is chosen from H, F, $CH_3$, $CF_3$;

$R^1$ and Ar are as defined above.

The more preferred pyrido[4,3-b]indoles of the general formulas 1.3 or the pharmaceutically acceptable salts thereof are selected from the group consisting of 2-methyl-5-phenylethynyl-2,3,4,5-tetrahydro-1H-pyrido[4,3-b]indole 1.3 (1), 2-methyl-5-(pyridin-2-ylethynyl)-2,3,4,5-tetrahydro-1H-pyrido[4,3-b]indole 1.3(2), 2-methyl-5-(pyridin-3-ylethynyl)-2,3,4,5-tetrahydro-1H-pyrido[4,3-b]indole 1.3 (3), 2-methyl-5-(pyridin-4-ylethynyl)-2,3,4,5-tetrahydro-1H-pyrido[4,3-b]indole 1.3(4), 2-methyl-5-(pyrimidin-5-ylethynyl)-2,3,4,5-tetrahydro-1H-pyrido[4,3-b]indole 1.3 (5), 2-methyl-5-phenylethynyl-8-fluoro-2,3,4,5-tetrahydro-1H-pyrido[4,3-b]indole 1.3.1(1), 2-methyl-5-(pyridin-2-ylethynyl)-8-fluoro-2,3,4,5-tetrahydro-1H-pyrido[4,3-b]indole 1.3.1(2), 2-methyl-5-(pyridin-3-ylethynyl)-8-fluoro-2,3,4,5-tetrahydro-1H-pyrido[4,3-b]indole 1.3.1(3), 2-methyl-5-(pyridin-4-ylethynyl)-8-fluoro-2,3,4,5-tetrahydro-1H-pyrido[4,3-b]indole 1.3.1(4), 2-methyl-5-(pyridin-3-ylethynyl)-6-fluoro-2,3,4,5-tetrahydro-1H-pyrido[4,3-b]indole 1.3.2(1), 2,8-dimethyl-5-phenylethynyl-2,3,4,5-tetrahydro-1H-pyrido[4,3-b]indole 1.3.1(5), 2,8-dimethyl-5-(pyridin-2-ylethynyl)-2,3,4,5-tetrahydro-1H-pyrido[4,3-b]indole 1.3.1(6), 2,8-dimethyl-5-(pyridin-2-ylethynyl)-2,3,4,5-tetrahydro-1H-pyrido[4,3-b]indole 1.3.1(7), 2,8-methyl-5-(pyridin-4-ylethynyl)-2,3,4,5-tetrahydro-1H-pyrido[4,3-b]indole 1.3.1(8), 2-methyl-5-(pyridin-3-ylethynyl)-8-trifluoromethyl-2,3,4,5-tetrahydro-1H-pyrido[4,3-b]indole 1.3.1(9), 2-methyl-5-(4-methoxyphenylethynyl)-8-fluoro-2,3,4,5-tetrahydro-1H-pyrido[4,3-b]indole 1.3.1(10), 2-methyl-5-(4-fluorophenylethynyl)-8-fluoro-2,3,4,5-tetrahydro-1H-pyrido[4,3-b]indole 1.3.1(11), 2-methyl-5-(3-fluorophenylethynyl)-8-fluoro-2,3,4,5-tetrahydro-1H-pyrido[4,3-b]indole 1.3.1(12), 2-methyl-5-(4-trifluoromethylphenylethynyl)-8-fluoro-2,3,4,5-tetrahydro-1H-pyrido[4,3-b]indole 1.3.1(13), 2-methyl-5-(pyridin-3-ylethynyl)-8-trifluoromethyl-2,3,4,5-tetrahydro-1H-pyrido[4,3-b]indole 1.3.1(14), 2,8-dimethyl-5-(4-fluorophenylethynyl)-2,3,4,5-tetrahydro-1H-pyrido[4,3-b]indole 1.3.1(15), 2,8-dimethyl-5-(3-fluorophenylethynyl)-2,3,4,5-tetrahydro-1H-pyrido[4,3-b]indole 1.3.1(16), 2,8-dimethyl-5-(4-trifluoromethylphenylethynyl)-2,3,4,5-tetrahydro-1H-pyrido[4,3-b]indole 1.3.1(17), 2,8-dimethyl-5-(3-trifluoromethylphenyl-ethynyl)-2,3,4,5-tetrahydro-1H-pyrido[4,3-b]indole 1.3.1(18), 2,8-dimethyl-5-(2-trifluoromethylphenylethynyl)-2,3,4,5-tetrahydro-1H-pyrido[4,3-b]indole 1.3.1(19), 2,8-dimethyl-5-(2-fluorophenylethynyl)-2,3,4,5-tetrahydro-1H-pyrido[4,3-b]indole 1.3.1(20), 2,8-dimethyl-5-(4-methoxyphenylethynyl)-2,3,4,5-tetrahydro-1H-pyrido[4,3-b]indole 1.3.1(21), 2,8-dimethyl-5-(4-dimethylaminophenylethynyl)-2,3,4,5-tetrahydro-1H-pyrido[4,3-b]indole 1.3.1(22), 2,8-dimethyl-5-(3-methoxyphenylethynyl)-2,3,4,5-tetrahydro-1H-pyrido[4,3-b]indole 1.3.1(23), and 2,8-dimethyl-5-(2-methoxyphenylethynyl)-2,3,4,5-tetrahydro-1H-pyrido[4,3-b]indole 1.3.1(24).

The purpose of the present invention is also methods for the synthesis of substituted 2,3,4,5-tetrahydro-1H-pyrido[4,3-b]indoles of the general formula 1, pharmaceutically acceptable salts and/or hydrates thereof.

According to the invention the method for the synthesis of substituted 5-ethenyl-2,3,4,5-tetrahydro-1H-pyrido[4,3-b]indoles of the general formula 1.1 consists in interaction of 2,3,4,5-tetrahydro-1H-pyrido[4,3-b]indoles of the general formula 2 with the corresponding acetylenes of the general formula 3 according to the following scheme 1.

Scheme 1

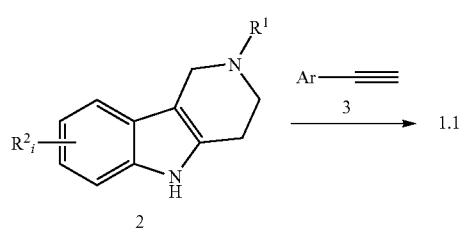

wherein: $R^1$, $R^2_i$ and Ar are as defined above.

According to the invention the method for the synthesis of substituted 5-[2-aryl(or heterocyclyl)ethyl]-2,3,4,5-tetrahydro-1H-pyrido[4,3-b]indoles of the general formula 1.2 consists in hydrogenation of substituted 5-ethenyl-2,3,4,5-tetrahydro-1H-pyrido[4,3-b]indoles of the general formula 1.1 according to the following scheme 2.

Scheme 2

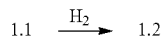

According to the invention the method for the synthesis of substituted 5-[2-aryl(or heterocyclyl)ethyl]-2,3,4,5-tetrahydro-1H-pyrido[4,3-b]indoles of the general formula 1.2 consists in interaction of 2,3,4,5-tetrahydro-1H-pyrido[4,3-b]indoles of the general formula 2 with substituted ethylene of the general formula 4 according to the following scheme 3.

Scheme 3

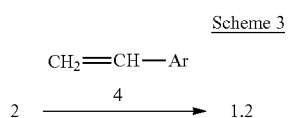

wherein: Ar is optionally substituted phenyl or optionally substituted 6-membered aromatic heterocycle containing 1 or 2 nitrogen atom in the cycle.

According to the invention the method for the synthesis of 5-ethynyl-2,3,4,5-tetrahydro-1H-pyrido[4,3-b]indoles of the general formula 1.3 consists in interaction of 2,3,4,5-tetrahydro-1H-pyrido[4,3-b]indoles of the general formula 2 with the corresponding halogenacetylenes of the general formula 5 according to the following scheme 4.

Scheme 4

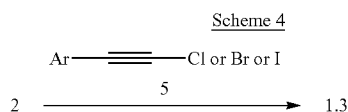

wherein: Hal are Cl, Br or I; Ar represents optionally substituted phenyl or optionally substituted 6-membered aromatic heterocycle containing 1 or 2 nitrogen atom in the cycle.

The starting 2,3,4,5-tetrahydro-1H-pyrido[4,3-b]indoles of the general formula 2 are prepared by the methods known in the art for the preparation of analogous compounds.

The starting 2,3,4,5-tetrahydro-1H-pyrido[4,3-b]indoles of the general formula 2 with different substituens in 2 and 8 positions are prepared by known Fisher indole synthesis. The reaction involves the interaction of substituted phenylhydrazine 2.1 (or their salts) and 1-substituted piperidine-4-ones 5, with the subsequent cyclization of the intermediate product as described in [N. Barbulescu, C. Bornaz, C. si Greff—Rev. Chim. (Bucuresti), 1971, v. 22, p. 269] according to the following scheme 5.

Scheme 5.

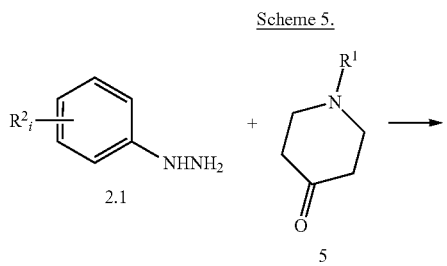

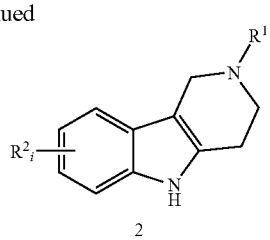

wherein: $R^1$ and $R^2_i$ are as defined above: in addition to $R^1$ may represent ethoxycarbonyl or tert-butyloxycarbonyl.

The starting compounds of the general formula 2 may also be prepared by interaction of 2,3,4,5-tetrahydro-1H-pyrido[4,3-b]indoles of the general formula 2.2 with isothiocyanates 2.3, 2.4 or sulfochlorides 2.5 according to the following scheme 6.

Scheme 6

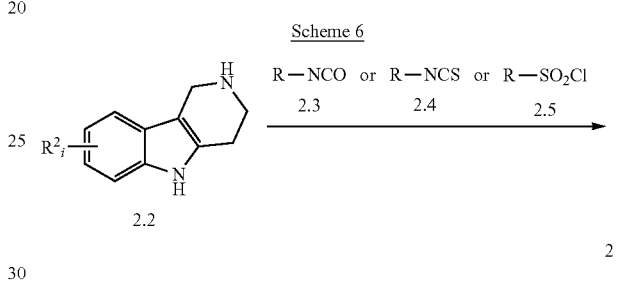

wherein: $R^2_i$ is as defined above; R represents the corresponding substituent.

Substituted 2,3,4,5-tetrahydro-1H-pyrido[4,3-b]indoles of the general formula 1 may form hydrates or pharmaceutically acceptable salts. Both organic and mineral acids could be used for salts preparation, for example, hydrochloric acid, hydrobromic acid, hydriodic acid, sulfuric acid, phosphoric acid, formic acid, acetic acid, propionic acid, trifluoroacetic acid, maleic acid, tartaric acid, methanesulphonic acid, benzenesulfonic acid, p-toluenesulfonic acid. Hydrates are usually formed during recrystallization of compounds of the general formula 1 or their salts from water or water containing solvents.

BEST EMBODIMENT OF THE INVENTION

The invention is illustrated by the following figures:

FIG. 1. The dependencies of the inhibition of the serotonine stimulated production of intracellular cAMP by the tested compounds. ■—1.1(1), □—1.1(2), ○—1.2.1(1)HCl, ●—1.3.1(1).

Figure 2:
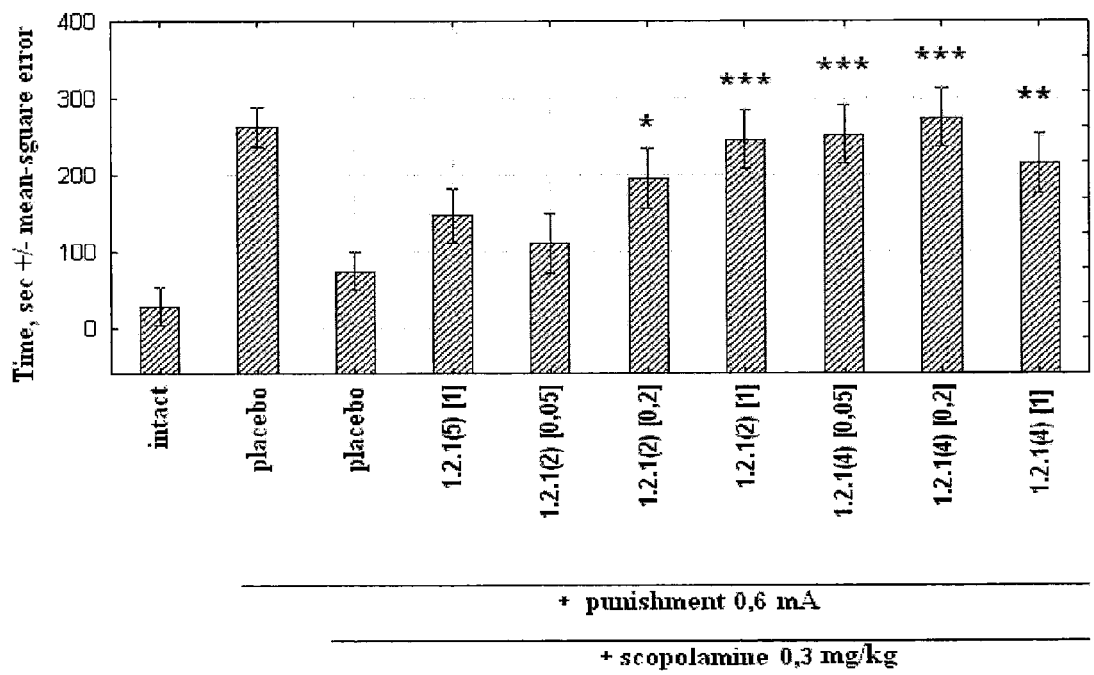

FIG. 2. The influence of antagonists of 5-HT$_6$ receptors 1.2.1(2)HCl, 1.2.1(4)HCl and 1.2.1(5)HCl on the latent period of the first calling at the dark section of the shuttle chamber in the test of passive avoidance at BALB/c mail mice. The figures in brackets mean the dosages in mg/kg. *—the statistically significant difference from the group of animals receiving a placebo at $p<0.05$, —at $p<0.01$, *—at $p<0.001$.

Figure 3:
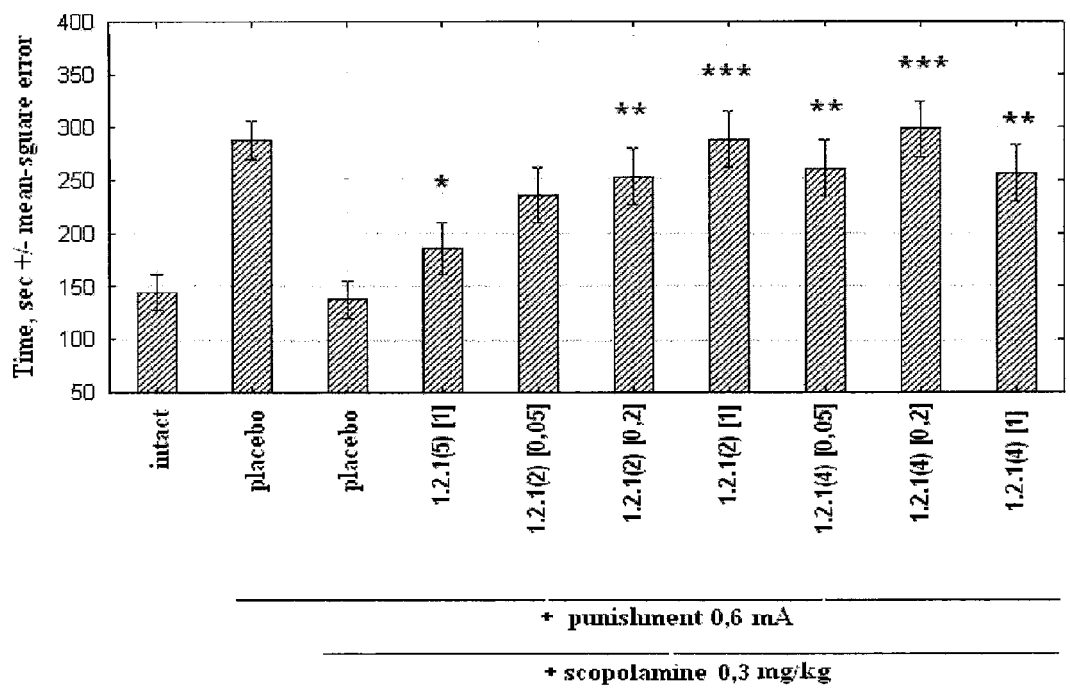

FIG. 3. The influence of antagonists of 5-HT$_6$ receptors 1.2.1(2)HCl, 1.2.1(4)HCl and 1.2.1(5)HCl on the time BALB/c male mice spent in the light section of the shuttle chamber in the test of passive avoidance. The figures in brackets mean the dosages in mg/kg. *—the statistically significant difference from the group of animals receiving a placebo at $p<0.05$, —at $p<0.01$, *—at $p<0.001$.

Figure 4:
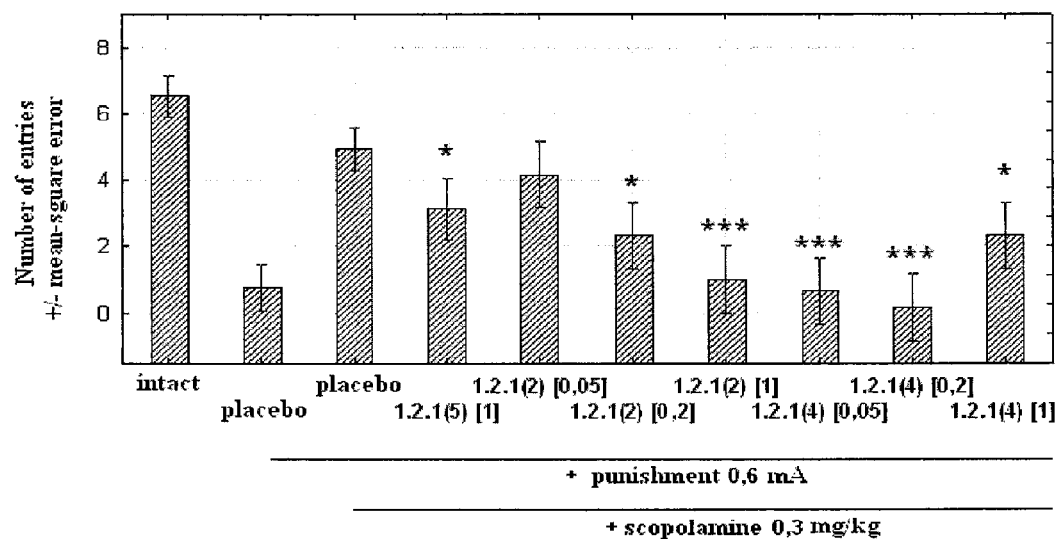

FIG. 4. The influence of antagonists of 5-HT$_6$ receptors 1.2.1(2)HCl, 1.2.1(4)HCl and 1.2.1(5)HCl on the number of callings at the dark section of the shuttle chamber in the test of passive avoidance with BALB/c male mice The numbers in brackets mean the dosages in mg/kg. *—the statistically significant difference from the group of animals receiving a placebo at $p<0.05$, ***—at $p<0.001$.

Figure 5:
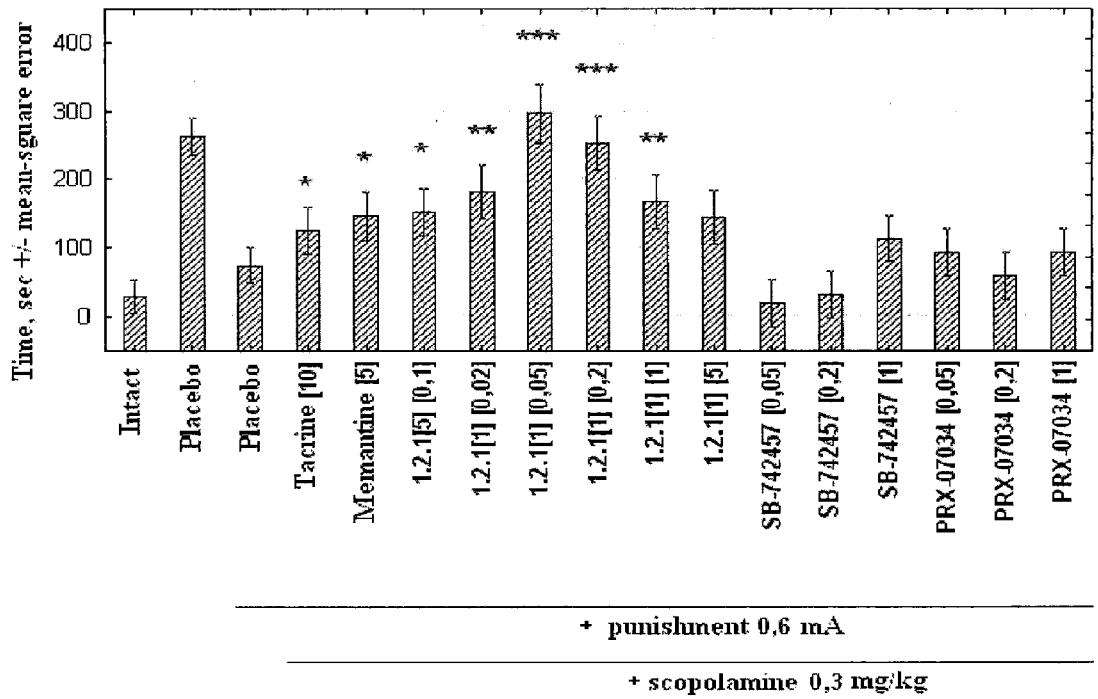

FIG. 5. The latent period of the first calling at the dark section of the shuttle chamber in the test of passive avoidance with BALB/c male mice. The numbers in brackets mean the dosages in mg/kg. *—the statistically significant difference from the group of animals receiving Scopolamine at $p<0.05$, —at $p<0.01$, *—at $p<0.001$.

Figure 6:
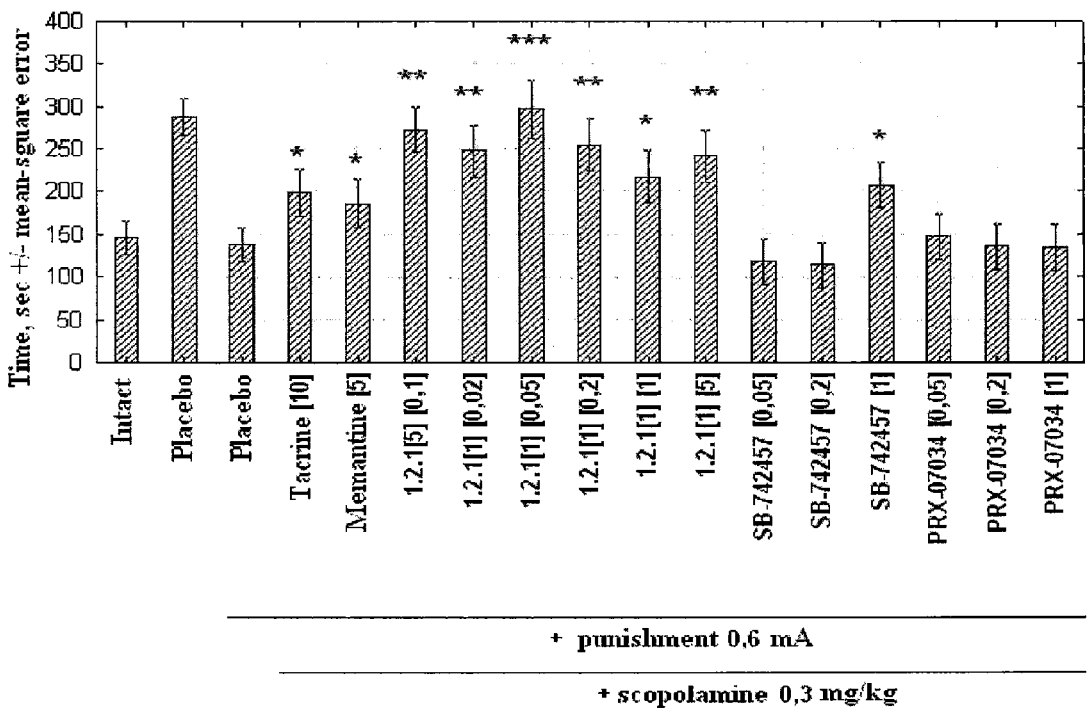

FIG. 6. The time spent by BALB/c male mice in the light section of the shuttle chamber in the test of passive avoidance. The numbers in brackets mean the dosages in mg/kg. *—the statistically significant difference from the group of animals receiving Scopolamine at $p<0.05$, —at $p<0.01$, *—at $p<0.001$.

Figure 7:
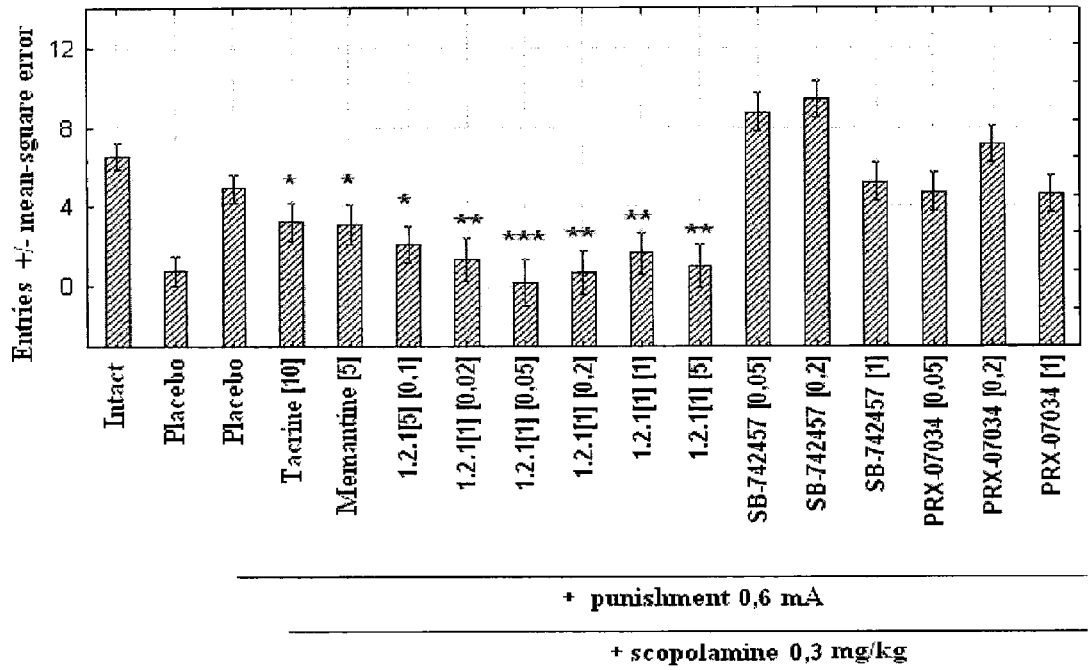

FIG. 7. The number of callings at the dark section of the shuttle chamber in the test of passive avoidance with BALB/c male mice. The numbers in brackets mean the dosages in mg/kg. *—the statistically significant difference from the group of animals receiving Scopolamine at $p<0.05$, ***—at $p<0.001$.

Figure 8:
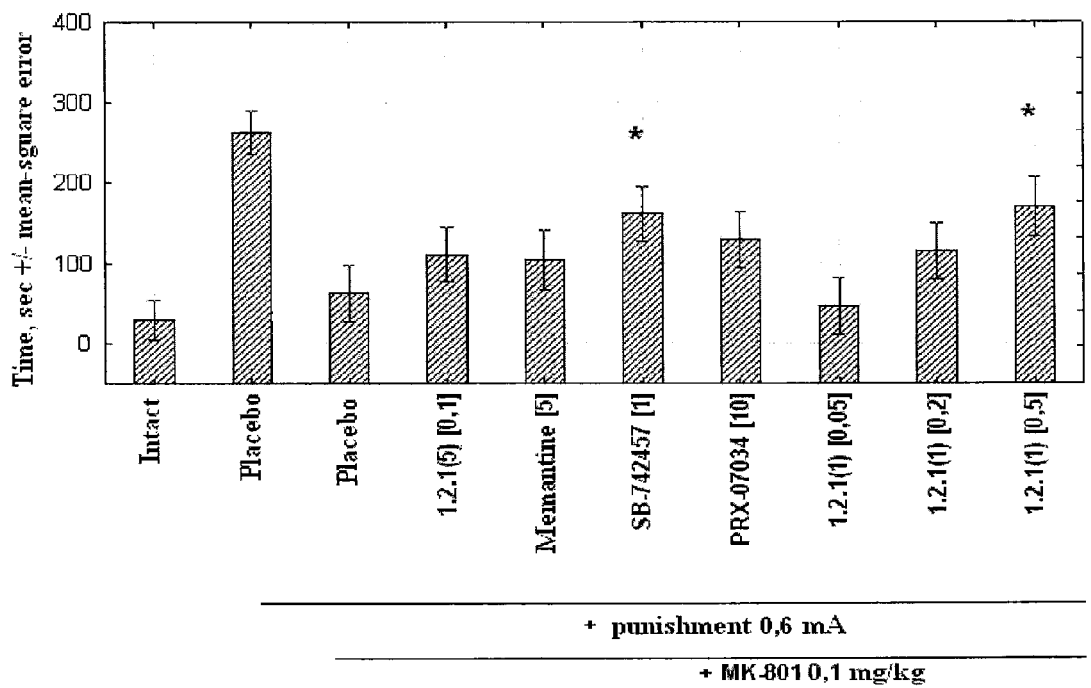

FIG. 8. The latent period of the first calling at the dark section of the shuttle chamber in the test of passive avoidance with BALB/c male mice. The numbers in brackets mean the dosages in mg/kg. *—the statistically significant difference from the group of animals receiving MK-801 at $p<0.05$.

Figure 9:
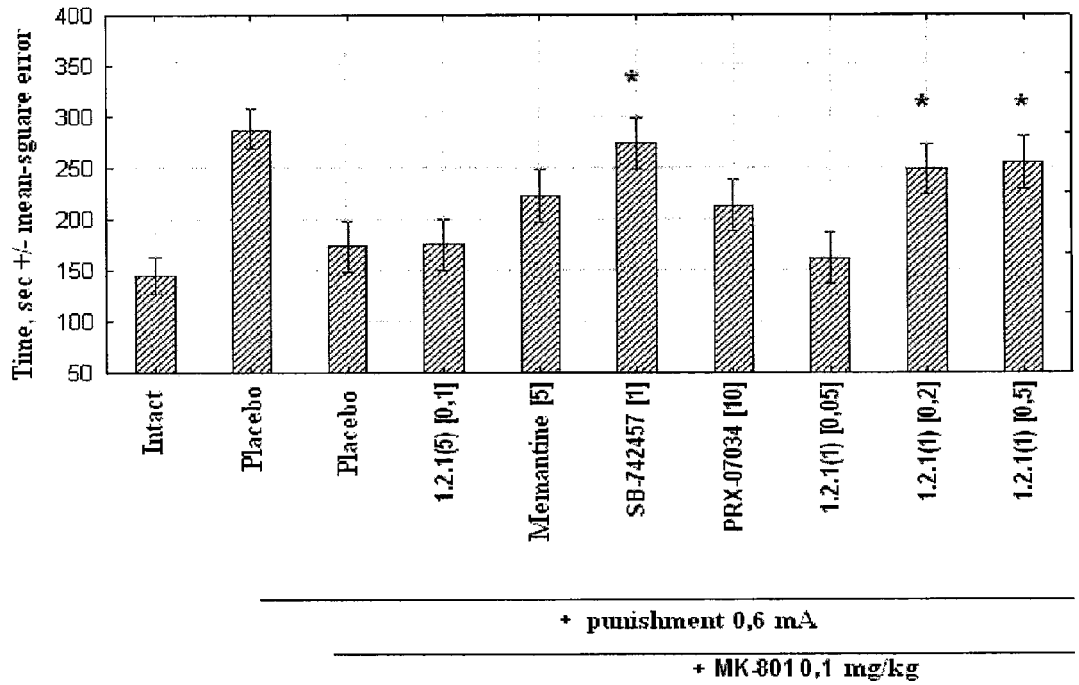

FIG. 9. The time spent in the light section of the shuttle chamber in the test of passive avoidance with BALB/c male mice. The numbers in brackets mean the dosages in mg/kg. *—the statistically significant difference from the group of animals receiving MK-801 at $p<0.05$.

Figure 10:
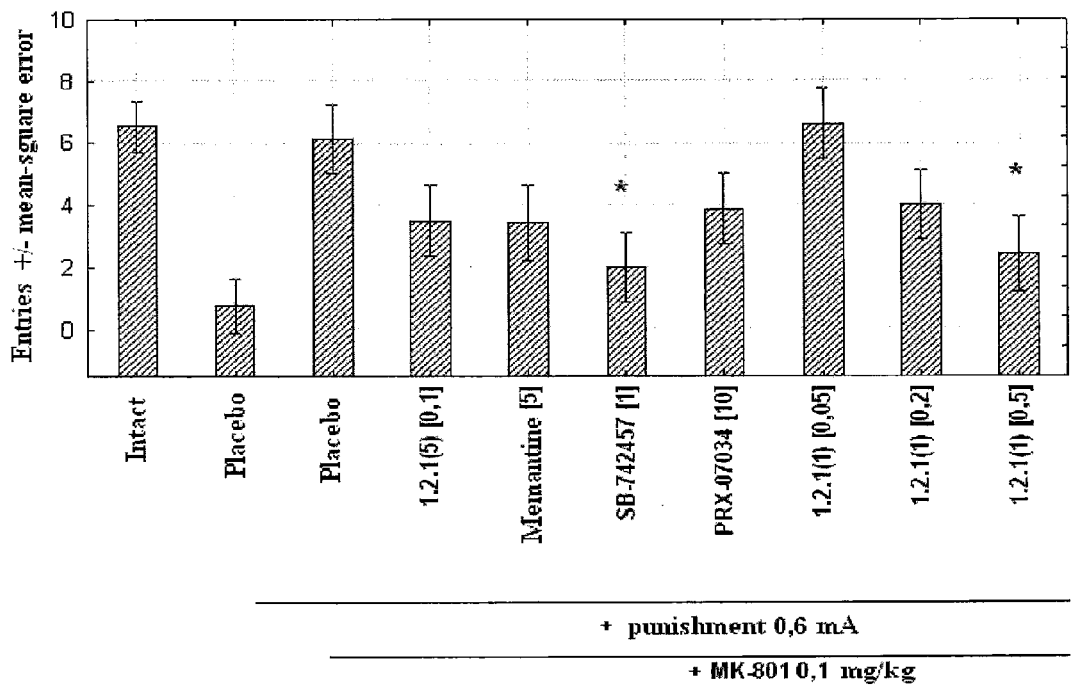

FIG. 10. The number of callings at the dark section of the shuttle chamber in the test of passive avoidance with BALB/c male mice. The numbers in brackets mean the dosages in mg/kg. *—the statistically significant difference from the group of animals receiving MK-801 at $p<0.05$.

Figure 11:
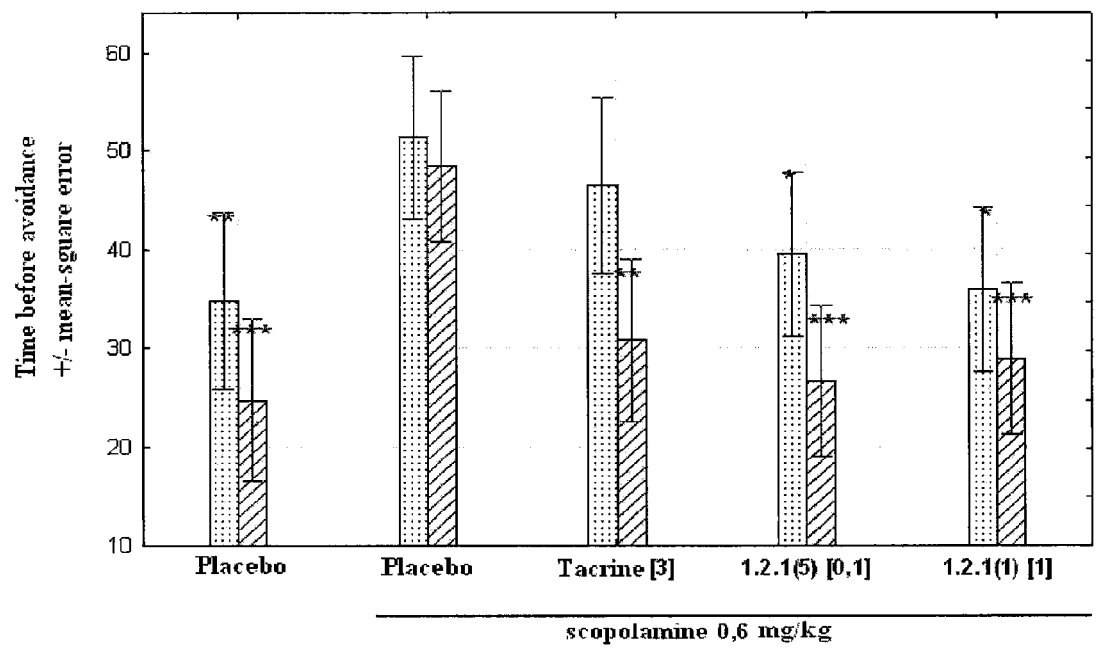

FIG. 11. The latent period of avoidance (climbing onto the platform, averaging over 4 combinations per day) in the first 2 days of mice training in the test of Morris water labyrinth. The numbers in brackets mean the dosages in mg/kg. ▭ Day 1 ▭ Day 2; *—the statistically significant difference from the group of animals receiving Scopolamine at $p<0.05$, —at $p<0.01$; *—at $p<0.001$.

Figure 12:
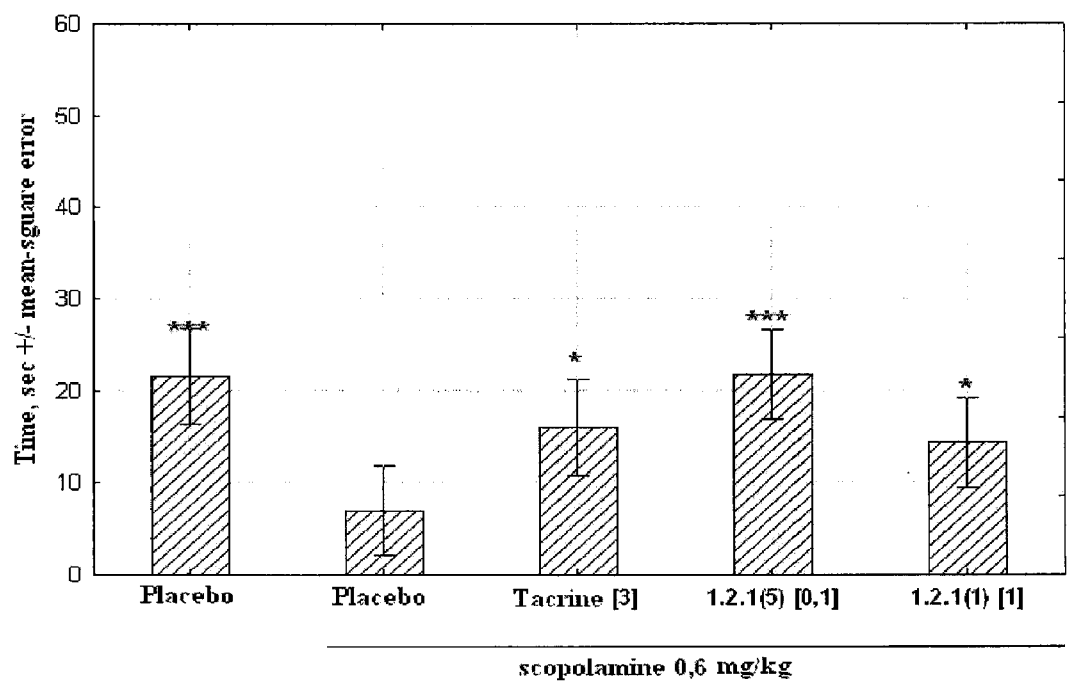

FIG. 12. The time spent in the area of the platform after two days of mice training in the Morris water labyrinth. The numbers in brackets mean the dosages in mg/kg. *—the difference from the group of animals receiving Scopolamine at $p<0.05$, ***—at $p<0.001$.

Figure 13:
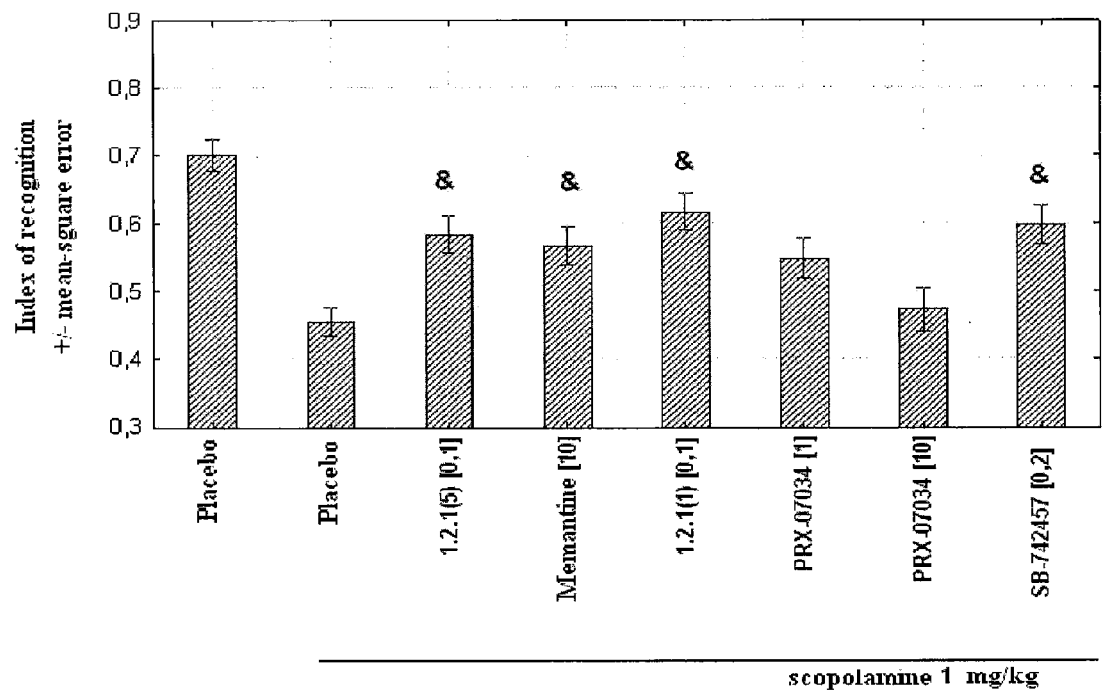

FIG. 13. Index of new object recognition at SHK male mice. The numbers in brackets mean the dosages in mg/kg. &—statistically significant difference from the group of animals receiving Scopolamine at $p<0.05$.

Figure 14:
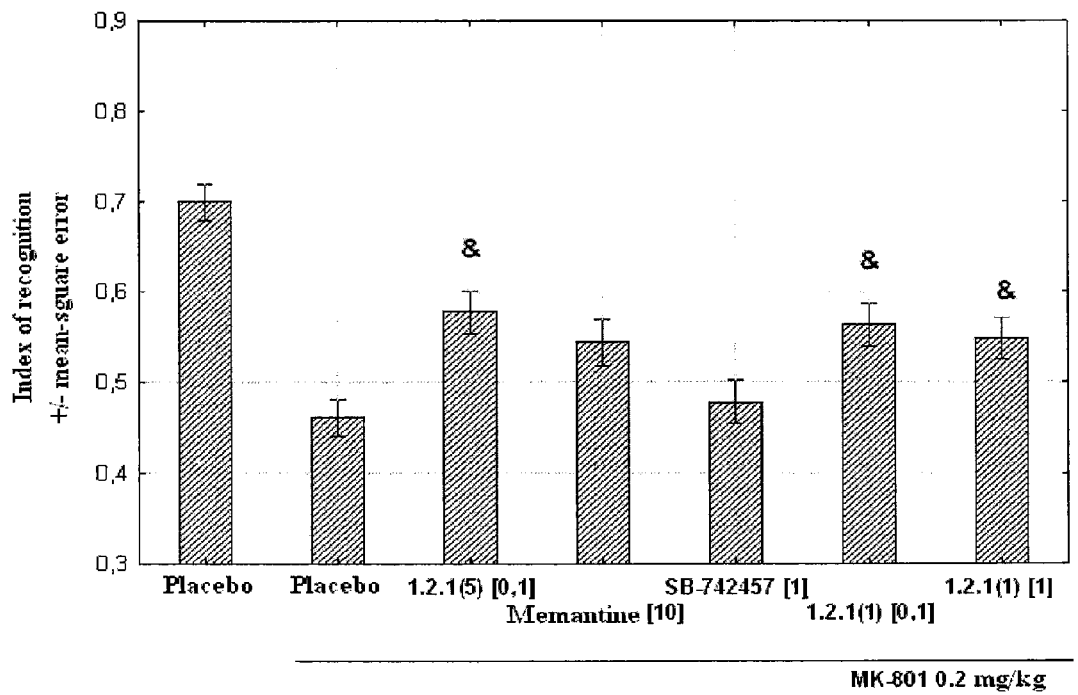

FIG. 14. Index of new object recognition at SHK male mice. The numbers in brackets mean the dosages in mg/kg. &—statistically significant difference from the group of animals receiving Scopolamine at $p<0.05$.

Figure 15:
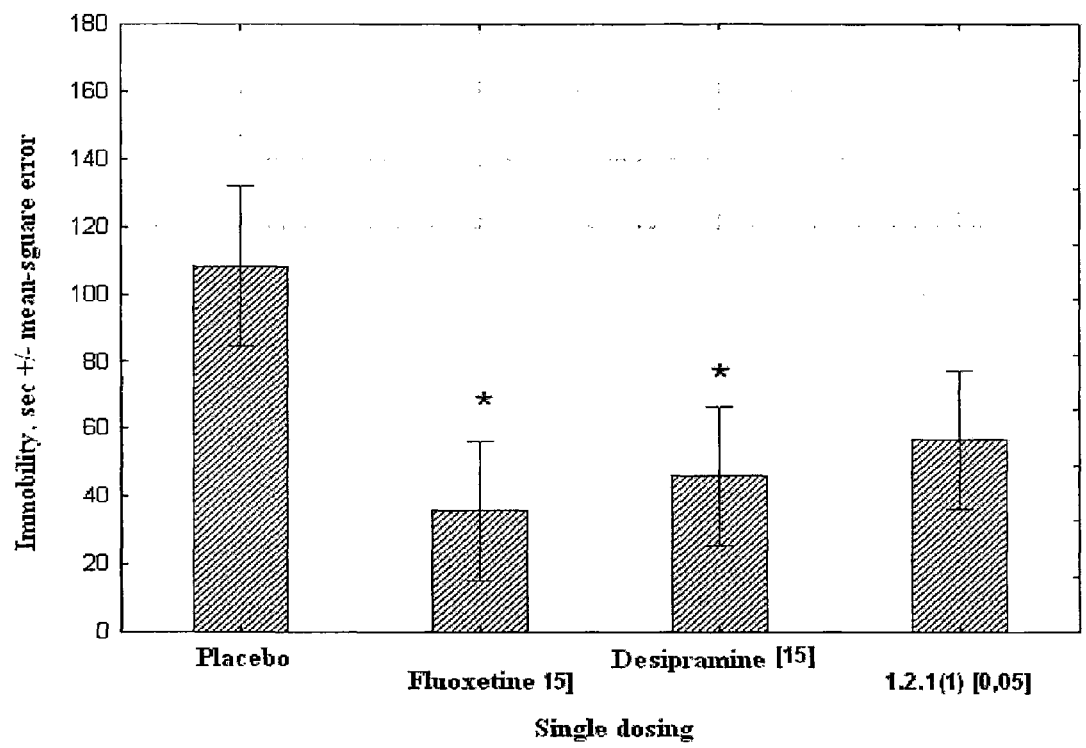

FIG. 15. The influence of standard antidepressants Fluoksetine, Dezipramine and antagonist of 5-HT$_6$ receptors 1.2.1(1)HCl on the total time of immobility in the Porsolt test. The numbers in brackets mean the dosages in mg/kg. *—statistically significant difference from the group of animals receiving a placebo at $p<0.05$.

Figure 16:
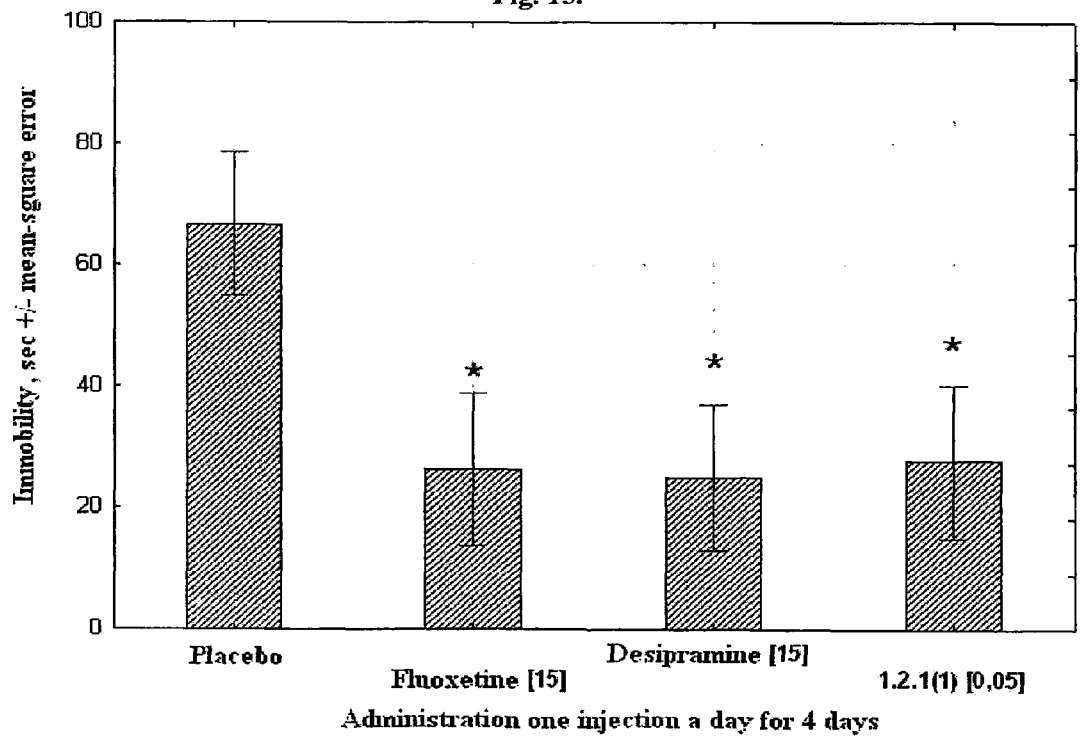

FIG. 16. The influence of the standard antidepressants Fluoksetine, Dezipramine and antagonist of 5-HT$_6$ receptors 1.2.1(1)HCl on the total time of immobility in the Porsolt test with BALB/c male mice. The numbers in brackets mean the dosages in mg/kg. *—statistically significant difference from the group of animals receiving a placebo at $p<0.05$.

Figure 17:
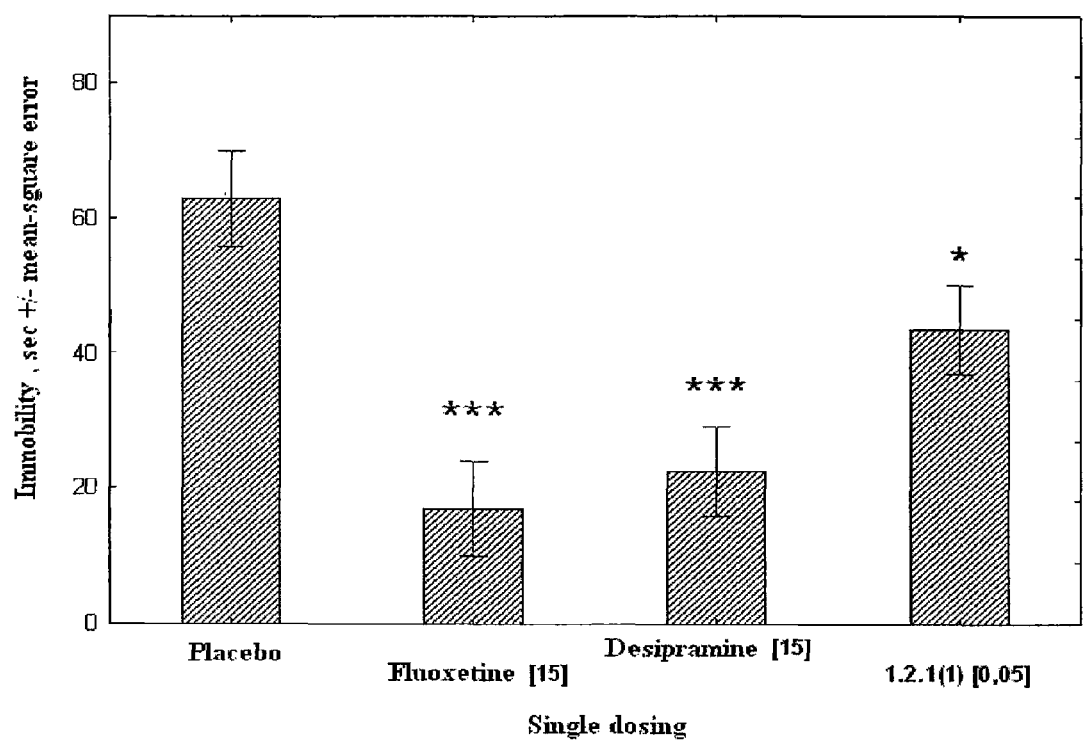

FIG. 17. The influence of the standard antidepressants Fluoksetine, Dezipramine and antagonist of 5-HT$_6$ receptors 1.2.1(1)HCl on the total time of immobility in the test of hanging by the tail with male mice of BALB/c line. The numbers in brackets mean the dosages in mg/kg. *—statistically significant difference from the group of animals receiving a placebo at $p<0.05$; ***—at $p<0.001$.

Figure 18:
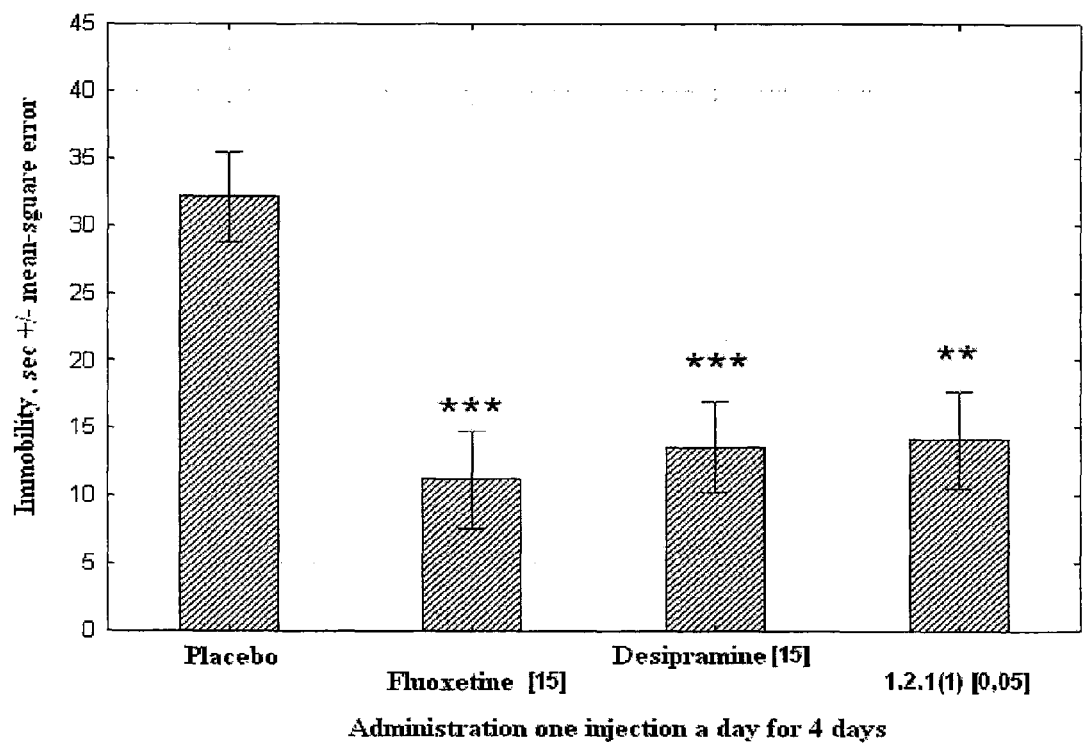

FIG. 18. The influence of the standard antidepressants Fluoksetine, Dezipramine and antagonist of 5-HT$_6$ receptors 1.2.1(1)HCl on the total time of immobility in the test of hanging by the tail with male mice of BALB/c line. The numbers in brackets mean the dosages in mg/kg. —statistically significant difference from the group with male mice of BALB/c line placebo at $p<0.01$; *—at $p<0.001$.

Figure 19:
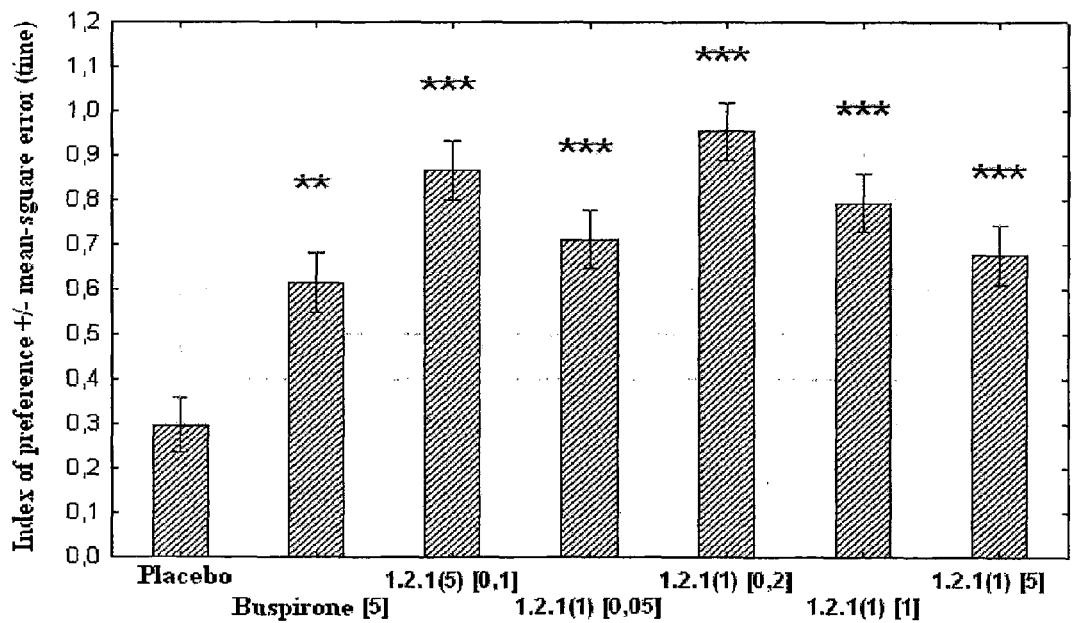

FIG. 19. The influence of the standard anxiolytic (tranquilizer) Buspirone and 1.2.1(1)HCl and antagonist of 5-HT$_6$ receptors 1.2.1(5)HCl on the preference index calculated on the time spent by BALB/c male mice in the open corridors of the labyrinth. The numbers in brackets mean the dosages in mg/kg. —statistically significant difference from the group of animals receiving a placebo at $p<0.05$; *—at $p<0.001$.

Figure 20:
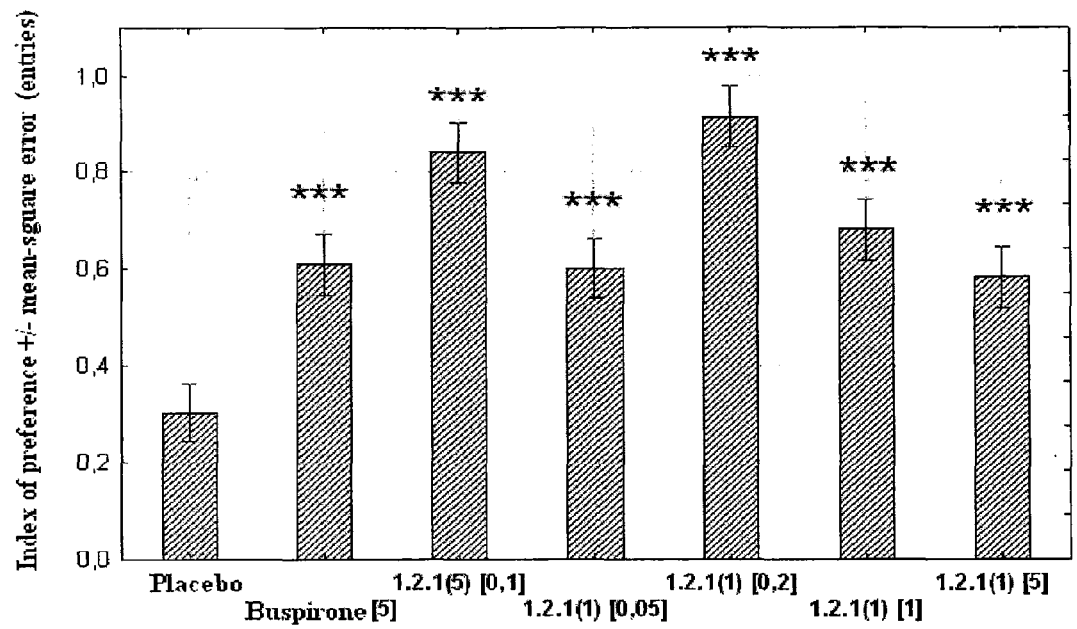
Figure 21:
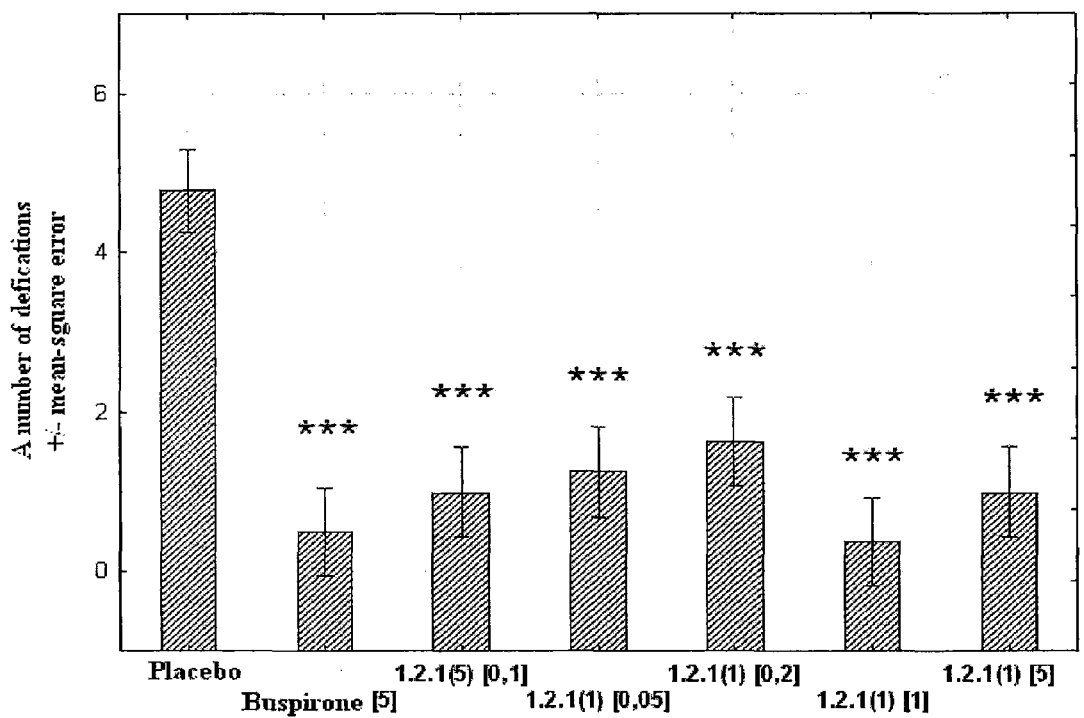

FIG. 20. The influence of the standard anxiolytic (tranquilizer) Buspirone and antagonist of 5-HT$_6$ receptors 1.2.1(1)HCl and 1.2.1(5)HCl on the preference index calculated on the number of times BALB/c male mice entered the open corridors of the labyrinth. The numbers in brackets mean the dosages in mg/kg. *—statistically significant difference from the group of animals receiving a placebo at $p<0.001$ FIG. 21. The influence of the standard anxiolytic (tranquilizer) Buspirone and 1.2.1(1)HCl and antagonist of 5-HT$_6$ receptor 1.2.1(5)HCl on the number of defecations by BALB/c male mice in the labyrinth. The numbers in brackets mean the dosages in mg/kg. *—statistically significant difference from the group of animals receiving a placebo at $p<0.001$ Below the invention is described by means of specific examples, which illustrate but not limit the scope of the invention.

Example 1. General Method for Preparation of 5-[2-aryl(or azaheterocyclyl)ethenyl]-2,3,4,5-tetrahydro-1H-pyrido[4,3-b]indoles of the General Formula 1.1

1 Mmol of 2,3,4,5-tetrahydro-1H-pyrido[4,3-b]indole 2, 1.5-2 mmol of aryl(or azaheterocyclyl)acetylene 3, 1 ml of dimethylsulfoxide, 3 ml of 60% water KOH solution and 100 mkl of 50% (Bu$_4$N)$_2$SO$_4$ water solution is stirred vigorously under argon atmosphere for 6-12 h at 20-80° C. Monitoring of the reaction is carried out by means of LCMS. Upon completion of the reaction the mixture is diluted with dichloromethane and washed with water. Organic layer is separated, dried over Na$_2$SO$_4$, and evaporated. The residue is purified by chromatography on silica gel impregnated with triethylamine eluting with hexane-chloroform-Et$_3$N mixture (6:3:1). 5-[2-Aryl(or azaheterocyclyl)ethenyl]-2,3,4,5-tetrahydro-1H-pyrido[4,3-b]indoles of the general formula 1.1 are prepared, among them:

cis-2-methyl-5-(2-phenylethenyl)-2,3,4,5-tetrahydro-1H-pyrido[4,3-b]indole 1.1(1), LCMS: m/z 289 [M+H], $^1$H NMR (400 MHz, DMSO-d$_6$): 7.46-7.43 (m, 1H), 7.23-7.19 (m, 3H), 7.12-7.05 (m, 3H), 6.99-6.95 (m, 2H), 6.97-6.95 (d, 1H, J=8.66 Hz), 6.71-6.69 (d, 1H, J=8.66 Hz), 3.60 (s, 2H), 2.65-2.62 (m, 2H), 2.55-2.54 (m, 2H), 2.43 (s, 3H); trans-2-methyl-5-(2-phenylethenyl)-2,3,4,5-tetrahydro-1H-pyrido[4,3-b]indole 1.1(2), LCMS: m/z 289 [M+H], $^1$H NMR (400 MHz, DMSO-d$_6$): 7.88-7.85 (m, 1H), 7.84-7.80 (d, 1H, J=14.65 Hz), 7.68-7.66 (m, 2H), 7.47-7.40 (m, 3H), 7.30-7.23 (m, 2H), 7.18-7.14 (m, 1H), 6.90-6.87 (d, 1H, J=14.65 Hz), 3.59 (s, 2H), 3.06-3.04 (m, 2H), 2.80-2.77 (m, 2H), 2.49 (s, 3H); trans-2-methyl-5-[2-(pyridin-4-yl)ethenyl]-2,3,4,5-tetrahydro-1H-pyrido[4,3-b]indole 1.1(3), LCMS: m/z 290 [M+H], $^1$H NMR (400 MHz, DMSO-d$_6$): 8.55-8.53 (m, 2H), 8.12-8.08 (d, 1H, J=15.02 Hz), 7.98-7.96 (m, 1H), 7.66-7.65 (m, 2H), 7.49-7.47 (m, 1H), 7.30-7.18 (m, 2H), 6.87-6.83 (d, 1H, J=15.02 Hz), 3.60 (s, 2H), 3.10-3.07 (m, 2H), 2.82-2.79 (m, 2H), 2.49 (s, 3H); cis-2-methyl-5-[2-(pyridin-3-yl)ethenyl]-2,3,4,5-tetrahydro-1H-pyrido[4,3-b]indole 1.1(4), LCMS: m/z 290 [M+H], $^1$H NMR (400 MHz, DMSO-d$_6$): 8.59-8.57 (m, 1H), 8.24-8.20 (d, 1H, J=14.65 Hz), 7.92-7.88 (m, 1H), 7.82-7.77 (m, 1H), 7.58-7.56 (m, 1H), 7.30-7.23 (m, 2H), 7.12-7.07 (m, 1H), 7.00-6.96 (d, 1H, J=14.65 Hz), 3.55 (s, 2H), 3.05-3.03 (m, 2H), 2.81-2.78 (m, 2H), 2.48 (s, 3H); trans-2-methyl-5-[2-(pyridin-2-yl)ethenyl]-2,3,4,5-tetrahydro-1H-pyrido[4,3-b]indole 1.1(5), LCMS: m/z 290 [M+H], $^1$H NMR (400 MHz, DMSO-d$_6$): 8.59-8.58 (m, 1H), 8.29-8.25 (d, 1H, J=14.28 Hz), 7.91-7.89 (m, 1H), 7.81-7.77 (m, 1H), 7.58-7.56 (m, 1H), 7.49-7.48 (m, 1H), 7.31-7.18 (m, 3H), 7.00-6.97 (d, 1H, J=14.28 Hz), 3.60 (s, 2H), 3.07-3.05 (m, 2H), 2.82-2.80 (m, 2H), 2.49 (s, 3H); cis-2-tert.butyl-5-[2-(pyridin-3-yl)ethenyl]-2,3,4,5-tetrahydro-1H-pyrido[4,3-b]indole 1.1(6), LCMS: m/z 332 [M+H]; cis-2-methyl-5-(2-phenylethenyl)-8-fluoro-2,3,4,5-tetrahydro-1H-pyrido[4,3-b]indole 1.1.1(1), LCMS: m/z 289 [M+H], trans-2-methyl-5-(2-phenylethenyl)-8-fluoro-2,3,4,5-tetrahydro-1H-pyrido[4,3-b]indole 1.1.3(1), LC-MS: m/z 289 [M+H]; trans-2-methyl-5-[2-(pyridin-4-yl)ethenyl]-8-fluoro-2,3,4,5-tetrahydro-1H-pyrido[4,3-b]indole 1.1.3(2), LC-MS: m/z 290 [M+H], $^1$H NMR (400 MHz, DMSO-d$_6$): 8.54-8.53 (m, 2H), 8.08-8.04 (d, 1H, J=14.65 Hz), 7.98-7.95 (m, 1H), 7.65-7.63 (m, 2H), 7.29-7.26 (m, 1H), 7.12-7.07 (m, 1H), 6.86-6.82 (d, 1H, J=14.65 Hz), 3.55 (s, 2H), 3.08-3.06 (m, 2H), 2.80-2.78 (m, 2H), 2.48 (s, 3H); cis-2-methyl-5-[2-(pyridin-3-yl)ethenyl]-8-fluoro-2,3,4,5-tetrahydro-1H-pyrido[4,3-b]indole 1.1.1(2), LCMS: m/z 290 [M+H], $^1$H NMR (400 MHz, DMSO-d$_6$): 8.40-8.38 (m, 1H), 8.22-8.21 (m, 1H), 7.27-7.17 (m, 3H), 7.13-7.11 (d, 1H, J=8.43), 7.02-7.98 (m, 1H), 6.90-6.85 (m, 1H), 6.77-6.75 (d, 1H, J=8.43 Hz), 3.57 (s, 2H), 2.69-2.66 (m, 2H), 2.60-2.55 (m, 2H), 2.44 (s, 3H); trans-2-methyl-5-[2-(pyridin-2-yl)ethenyl]-8-fluoro-2,3,4,5-tetrahydro-1H-pyrido[4,3-b]indole 1.1.3(3), LCMS: m/z 290 [M+H], $^1$H NMR (400 MHz, DMSO-d$_6$): 8.59-8.57 (m, 1H), 8.24-8.20 (d, 1H, J=14.65 Hz), 7.92-7.88 (m, 1H), 7.82-7.77 (m, 1H), 7.58-7.56 (m, 1H), 7.30-7.23 (m, 2H), 7.12-7.07 (m, 1H), 7.00-6.96 (d, 1H, J=14.65 Hz), 3.55 (s, 2H), 3.05-3.03 (m, 2H), 2.81-2.78 (m, 2H), 2.48 (s, 3H); cis-2,8-dimethyl-5-(2-phenylethenyl)-2,3,4,5-tetrahydro-1H-pyrido[4,3-b]indole 1.1.1(3), LCMS: m/z 303 [M+H]; trans-2,8-dimethyl-5-[2-phenylethenyl]-2,3,4,5-tetrahydro-1H-pyrido[4,3-b]indole 1.1.3(4), LCMS: m/z 303 [M+H]; cis-2,8-dimethyl-5-[2-(pyridin-3-yl)ethenyl]-2,3,4,5-tetrahydro-1H-pyrido[4,3-b]indole 1.1.1(4), LCMS: m/z 304 [M+H]; trans-2,8-dimethyl-5-[2-(pyridin-4-yl)ethenyl]-2,3,4,5-tetrahydro-1H-pyrido[4,3-b]indole 1.1.3(5), LCMS: m/z 304 [M+H]; cis-2-benzyl-8-methyl-5-[2-(pyridin-2-yl)ethenyl]-2,3,4,5-tetrahydro-1H-pyrido[4,3-b]indole 1.1.1(5), LCMS: m/z 380 [M+H]; trans-2-methyl-5-[2-(4-fluorophenyl)ethenyl]-8-fluoro-2,3,4,5-tetrahydro-1H-pyrido[4,3-b]indole 1.1.3(6), LCMS: m/z 325 [M+H]; cis-2-methyl-5-[2-(3-fluorophenyl)ethenyl]-8-fluoro-2,3,4,5-tetrahydro-1H-pyrido[4,3-b]indole 1.1.1(6), LC-MS: m/z 325 [M+H]; trans-2,8-dimethyl-5-[2-(4-trifluoromethylphenyl)ethenyl]-2,3,4,5-tetrahydro-1H-pyrido[4,3-b]indole 1.1.3(7), LCMS: m/z 371 [M+H]; cis-2,8-dimethyl-5-[2-(3-trifluoromethylphenyl)ethenyl]-2,3,4,5-tetrahydro-1H-pyrido[4,3-b]indole 1.1.1(7), LCMS: m/z 371 [M+H]; trans-2-methyl-5-[2-(4-trifluoromethylphenyl)ethenyl]-8-fluoro-2,3,4,5-tetrahydro-1H-pyrido[4,3-b]indole 1.1.3(8), LCMS: m/z 375 [M+H]; cis-2-methyl-5-[2-(4-methoxyphenyl)ethenyl]-8-fluoro-2,3,4,5-tetrahydro-1H-pyrido[4,3-b]indole 1.1.1(8), LCMS: m/z 337 [M+H]; cis-2-methyl-5-[2-(4-dimethylaminophenyl)ethenyl]-8-fluoro-2,3,4,5-tetrahydro-1H-pyrido[4,3-b]indole 1.1.1(9), LCMS: m/z 350 [M+H]; trans-2,8-dimethyl-5-[2-(4-fluorophenyl)ethenyl]-2,3,4,5-tetrahydro-1H-pyrido[4,3-b]indole 1.1.3(9), LCMS: m/z 321 [M+H] and others.

Example 2. General Method for Preparation of 5-[2-aryl(or azaheterocyclyl)ethyl]-2,3,4,5-tetrahydro-1H-pyrido[4,3-b]indoles of the General Formula 1.2

A. 200 mg of PtO$_2$ is added to a solution of 2 mmol of 5-[2-aryl(or azaheterocyclyl)ethenyl]-2,3,4,5-tetrahydro-1H-pyrido[4,3-b]indole of the general formula 1.1 in 40 ml of ethanol and the resultant mixture is hydrogenated by hydrogen at stirring and room temperature for 24 hs. Upon completion of the reaction (LCMS monitoring) the mixture is filtered or centrifugated. Filtrate is evaporated in vacuo, and the residue is purified by chromatography on silica gel impregnated with triethylamine eluting with CHCl$_3$-hexane-Et$_3$N mixture (3:6:1) or recrystallized from the proper solvent. 5-[2-Aryl(or azaheterocyclyl)ethyl]-2,3,4,5-tetrahydro-1H-pyrido[4,3-b]indoles of the general formular 1.2 are prepared.

B. A solution of 2,3,4,5-tetrahydro-1H-pyrido[4,3-b]indole 2 (7.5 mmol), 7.5 mmol of tetramethylguanidine and 15.0 mmol of aryl(or azaheterocyclyl)ethylene 4 in 7.5 ml of dimethylsulfoxide is stirred vigorously under argon atmosphere at 90° C. for 12 h. The mixture is diluted with water and extracted with benzene. The extract is washed with 5% K$_2$CO$_3$ water solution, dried over Na$_2$SO$_4$ and evaporated in vacuo. Product is washed with the proper solvent, recrystallised from a suitable solvent or purified by chromatography eluting with dichloromethan-THF-triethylamine mixture. 5-[2-Aryl(or azaheterocyclyl)ethyl]-2,3,4,5-tetrahydro-1H-pyrido[4,3-b]indoles of the general formula 1.2. are prepared, among them: 2-methyl-5-(2-phenylethyl)-2,3,4,5-tetrahydro-1H-pyrido[4,3-b]indole 1.2(1), LCMS: m/z 291 [M+H]; 2-methyl-5-[2-(pyridin-4-yl)ethyl]2,3,4,5-tetrahydro-1H-pyrido[4,3-b]indole 1.2(2), LCMS: m/z 292 [M+H]; 2-methyl-5-[2-(pyridin-3-yl)ethyl]-2,3,4,5-tetrahydro-1H-pyrido[4,3-b]indole 1.2(3), LCMS: m/z 292 [M+H]; 2-methyl-5-[2-(pyridine-2-yl)ethyl]-2,3,4,5-tetrahydro-1H-pyrido[4,3-b]indole 1.2(4), LC-MS: m/z 292 [M+H]; 2-tert.-butyl-5-[2-(pyridin-3-yl)ethyl]-2,3,4,5-tetrahydro-1H-pyrido[4,3-b]indole 1.2(5), LCMS: m/z 333 [M+H]; 2-methyl-5-[2-(6-methylpyridin-3-yl)ethyl]-2,3,4,5-tetrahydro-1H-pyrido[4,3-b]indole 1.2(6), LCMS: m/z 306 [M+H]; 2,8-dimethyl-5-(2-phenylethyl)-2,3,4,5-tetrahydro-1H-pyrido[4,3-b]indole 1.2.1(1), LCMS: m/z 305 [M+H]; 2,8-dimethyl-5-[2-(pyridin-4-yl)ethyl]-2,3,4,5-tetrahydro-1H-pyrido[4,3-b]indole 1.2.1(2), LCMS: m/z 306 [M+H]; 2,8-dimethyl-5-[2-(pyridin-3-yl)ethyl]-2,3,4,5-tetrahydro-1H-pyrido[4,3-b]indole 1.2.1(3), LCMS: m/z 306 [M+H]; 2,8-dimethyl-5-[2-(pyridin-2-yl)ethyl]-2,3,4,5-tetrahydro-1H-pyrido[4,3-b]indole 1.2.1(4), LCMS: m/z 306 [M+H]; 2,8-dimethyl-5-[2-(6-methylpyridin-3-yl)ethyl]-2,3,4,5-tetrahydro-1H-pyrido[4,3-b]indole 1.2.1(5), LCMS: m/z 320 [M+H]; 2,8-dimethyl-5-[2-(pyrazin-2-yl)ethyl]-2,3,4,5-tetrahydro-1H-pyrido[4,3-b]indole 1.2.1(6), LCMS: m/z 305 [M+H]; 2-methyl-5-(2-phenylethyl)-8-fluoro-2,3,4,5-tetrahydro-1H-pyrido[4,3-b]indole 1.2.1(7), LCMS: m/z 309 [M+H]; 2-methyl-5-[2-(pyridin-4-yl)ethyl]-8-fluoro-2,3,4,5-tetrahydro-1H-pyrido[4,3-b]indole 1.2.1(8), LCMS: m/z 310 [M+H]; 2-methyl-5-[2-(pyridin-3-yl)ethyl]-8-fluoro-2,3,4,5-tetrahydro-1H-pyrido[4,3-b]indole 1.2.1(9), LCMS: m/z 310 [M+H]; 2-methyl-5-[2-(pyridin-2-yl)ethyl]-8-fluoro-2,3,4,5-tetrahydro-1H-pyrido[4,3-b]indole 1.2.1(10), LCMS: m/z 310 [M+H]; 2-methyl-5-[2-(6-methylpyridin-3-yl)ethyl]-8-fluoro-2,3,4,5-tetrahydro-1H-pyrido[4,3-b]indole 1.2.1(11), LCMS: m/z 324 [M+H]; 2-methyl-5-(2-phenylethyl)-8-trifluoromethyl-2,3,4,5-tetrahydro-1H-pyrido[4,3-b]indole 1.2.1(12), LCMS: m/z 309 [M+H]; 2-methyl-5-[2-(pyridin-3-yl)ethyl]-8-trifluoromethyl-2,3,4,5-tetrahydro-1H-pyrido[4,3-b]indole 1.2.1(13), LCMS: m/z 310 [M+H]; 2-methyl-5-(2-phenylethyl)-6-fluoro-2,3,4,5-tetrahydro-1H-pyrido[4,3-b]indole 1.2.2(1), LCMS: m/z 310 [M+H]; 2-methyl-5-(2-phenylethyl)-6-trifluoromethyl-2,3,4,5-tetrahydro-1H-pyrido[4,3-b]indole 1.2.2(2), LCMS: m/z 310 [M+H]; 2-methyl-5-[2-(pyridin-3-yl)ethyl]-6-trifluoromethyl-2,3,4,5-tetrahydro-1H-pyrido[4,3-b]indole 1.2.2(3), LCMS: m/z 324 [M+H] and others.

Example 3. General Method for Preparation of 5-[2-aryl(or azaheterocyclyl)ethynyl]-2,3,4,5-tetrahydro-1H-pyrido[4,3-b]indoles of the General Formula 1.3

50 mg (0.2 mmol) of CuSO4×5H2O, 74 mg (0.4 mmol) of 1,10-phenanthroline, 890 mg of dry powdered $K_3PO_4$ and 2.2 mmol of halogenacetylene 5 is added to a solution of 2 mmol of ,3,4,5-tetrahydro-1H-pyrido[4,3-b]indole 2 in 3 ml of toluene under argon atmosphere. The mixture is stirred at temperature 80-85° C. for 12 hr. Monitoring of the reaction was carried out by means of LCMS. Upon completion of the reaction the reaction mixture is diluted with ester and filtered. The solvent is evaporated, the residue is purified by chromatography on silica gel impregnated with triethylamine eluting with hexane-chloroform-$Et_3N$ mixture (6:3:1). 5-[2-Aryl(or azaheterocyclyl)ethynyl]-2,3,4,5-tetrahydro-1H-pyrido[4,3-b]indoles 1.3 are prepared, among them: 2-methyl-5-phenylethynyl-2,3,4,5-tetrahydro-1H-pyrido[4,3-b]indole 1.3(1), LCMS: m/z 287 [M+H], $^1$H NMR (400 MHz, DMSO-$d_6$): 7.65-7.63 (m, 3H), 7.52-7.44 (m, 4H), 7.32-7.30 (m, 1H), 7.26-7.23 (m, 1H), 3.57 (br. s, 2H), 2.93-2.91 (m, 2H), 2.83-2.81 (m, 2H), 2.48 (s, 3H); 2-methyl-5-(pyridin-2-ylethynyl)-2,3,4,5-tetrahydro-1H-pyrido[4,3-b]indole 1.3(2), LCMS: m/z 288 [M+H]; 2-methyl-5-(pyridin-3-ylethynyl)-2,3,4,5-tetrahydro-1H-pyrido[4,3-b]indole 1.3(3), LCMS: m/z 288 [M+H]; 2-methyl-5-(pyridin-4-ylethynyl)-2,3,4,5-tetrahydro-1H-pyrido[4,3-b]indole 1.3(4), LCMS: m/z 288 [M+H]; 2-methyl-5-(pyrimidin-5-ylethynyl)-2,3,4,5-tetrahydro-1H-pyrido[4,3-b]indole 1.3(5), LCMS: m/z 289 [M+H]; 2-methyl-5-phenylethynyl-8-fluoro-2,3,4,5-tetrahydro-1H-pyrido[4,3-b]indole 1.3.1(1), LC-MS: m/z 305 [M+H], $^1$H NMR (400 MHz, DMSO-$d_6$): 7.65-7.61 (m, 3H), 7.50-7.45 (m, 3H), 7.35-7.32 (m, 1H), 7.17-7.12 (m, 1H), 3.54 (br. s, 2H), 2.93-2.91 (m, 2H), 2.83-2.81 (m, 2H), 2.48 (s, 3H); 2-methyl-5-(pyridin-2-ylethynyl)-8-fluoro-2,3,4,5-tetrahydro-1H-pyrido[4,3-b]indole 1.3.1(2), LCMS: m/z 306 [M+H]; 2-methyl-5-(pyridin-3-ylethynyl)-8-fluoro-2,3,4,5-tetrahydro-1H-pyrido[4,3-b]indole 1.3.1(3), LCMS: m/z 306 [M+H], $^1$H NMR (400 MHz, DMSO-$d_6$): 8.85-8.84 (m, 1H), 8.62-8.60 (m, 1H), 8.06-8.03 (m, 1H), 7.69-7.66 (m, 1H), 7.52-7.49 (m, 1H), 7.36-7.33 (m, 1H), 7.18-7.13 (m, 1H), 3.53 (s, 2H), 2.94-2.92 (m, 2H), 2.81-2.80 (m, 2H), 2.48 (s, 3H); 2-methyl-5-(pyridin-4-ylethynyl)-8-fluoro-2,3,4,5-tetrahydro-1H-pyrido[4,3-b]indole 1.3.1(4), LCMS: m/z 306 [M+H]; 2-methyl-5-(pyridin-3-ylethynyl)-6-fluoro-2,3,4,5-tetrahydro-1H-pyrido[4,3-b]-indole 1.3.2(1), LCMS: m/z 306 [M+H]; 2,8-dimethyl-5-phenylethynyl-2,3,4,5-tetrahydro-1H-pyrido[4,3-b]indole 1.3.1(5), LCMS: m/z 301 [M+H]; 2,8-dimethyl-5-(pyridin-2-ylethynyl)-2,3,4,5-tetrahydro-1H-pyrido[4,3-b]indole 1.3.1(6), LCMS: m/z 302 [M+H]; 2,8-dimethyl-5-(pyridin-3-ylethynyl)-2,3,4,5-tetrahydro-1H-pyrido[4,3-b]indole 1.3.1(7), LCMS: m/z 302 [M+H]; 2,8-dimethyl-5-(pyridin-4-ylethynyl)-2,3,4,5-tetrahydro-1H-pyrido[4,3-b]indole 1.3.1(8), LCMS: m/z 302 [M+H]; 2-methyl-5-(pyridin-3-ylethynyl)-8-trifluoromethyl-2,3,4,5-tetrahydro-1H-pyrido[4,3-b]indole 1.3.1(9), LCMS: m/z 352 [M+H]; 2-methyl-5-(4-methoxyphenylethynyl)-8-fluoro-2,3,4,5-tetrahydro-1H-pyrido[4,3-b]indole 1.3.1(10), LCMS: m/z 335 [M+H]; 2-methyl-5-(4-fluorophenylethynyl)-8-fluoro-2,3,4,5-tetrahydro-1H-pyrido[4,3-b]indole 1.3.1(11), LCMS: m/z 323 [M+H]; 2-methyl-5-(3-fluorophenylethynyl)-8-fluoro-2,3,4,5-tetrahydro-1H-pyrido[4,3-b]indole 1.3.1(12), LCMS: m/z 323 [M+H]; 2-methyl-5-(4-trifluoromethylphenylethynyl)-8-fluoro-2,3,4,5-tetrahydro-1H-pyrido[4,3-b]indole 1.3.1(13), LCMS: m/z 373 [M+H]; 2-methyl-5-(pyridin-3-ylethynyl)-8-trifluoromethyl-2,3,4,5-tetrahydro-1H-pyrido[4,3-b]indole 1.3.2(14), LCMS: m/z 356 [M+H]; 2,8-dimethyl-5-(4-fluorophenylethynyl)-2,3,4,5-tetrahydro-1H-pyrido[4,3-b]indole 1.3.1(15), LCMS: m/z 319 [M+H]; 2,8-dimethyl-5-(3-fluorophenylethynyl)-2,3,4,5-tetrahydro-1H-pyrido[4,3-b]indole 1.3.1(16), LCMS: m/z 319 [M+H]; 2,8-dimethyl-5-(4-trifluoromethylphenylethynyl)-2,3,4,5-tetrahydro-1H-pyrido[4,3-b]indole 1.3.1(17), LCMS: m/z 369 [M+H]; 2,8-dimethyl-5-(3-trifluoromethylphenylethynyl)-2,3,4,5-tetrahydro-1H-pyrido[4,3-b]indole 1.3.1(18), LCMS: m/z 369 [M+H]; 2,8-dimethyl-5-(2-trifluoromethyl-phenylethynyl)-2,3,4,5-tetrahydro-1H-pyrido[4,3-b]indole 1.3.1(19), LCMS: m/z 369 [M+H]; 2,8-dimethyl-5-(2-fluorophenylethynyl)-2,3,4,5-tetrahydro-1H-pyrido[4,3-b]indole 1.3.1(20), LCMS: m/z 319 [M+H]; 2,8-dimethyl-5-(4-methoxyphenylethynyl)-2,3,4,5-tetrahydro-1H-pyrido[4,3-b]indole 1.3.1(21), LCMS: m/z 331 [M+H]; 2,8-dimethyl-5-(4-dimethylaminophenylethynyl)-2,3,4,5-tetrahydro-1H-pyrido[4,3-b]indole 1.3.1(22), LCMS: m/z 344 [M+H]; 2,8-dimethyl-5-(3-methoxyphenylethynyl)-2,3,4,5-tetrahydro-1H-pyrido[4,3-b]indole 1.3.1(23), LCMS: m/z 331 [M+H]; 2,8-dimethyl-5-(2-methoxyphenylethynyl)-2,3,4,5-tetrahydro-1H-pyrido[4,3-b]indole 1.3.1(24), LCMS: m/z 331 [M+H] and others.

Example 4

General method for preparation of 2,3,4,5-tetrahydro-1H-pyrido[4,3-b]indoles of the general formulas 1.1, 1.2 in the form of salts. To a solution of 1 mmol of 2,3,4,5-tetrahydro-1H-pyrido[4,3-b]indole of the general formulas 1.1 or 1.2 in ester, dioxane or methanol 0.76 ml (2.1 mmol) of dioxane or methanol solution of HCl or HBr is added. The precipitated white solid is separated, washed with acetone and/or ester, dried in vacuo. It gives 2,3,4,5-tetrahydro-1H-pyrido[4,3-b] indoles of the general formulas 1.1, 1.2 in the form of salts, among them: cis-2-methyl-5-(2-phenylethenyl)-2,3,4,5-tetrahydro-1H-pyrido[4,3-b]indole hydrochloride 1.1(1)HCl, LCMS: m/z 289 [M+H]; trans-2-methyl-5-(2-phenylethenyl)-2,3,4,5-tetrahydro-1H-pyrido[4,3-b]indole hydrochloride 1.1(2)HCl, LCMS: m/z 289 [M+H]; trans-2-methyl-5-[2-(pyridin-4-yl)ethenyl]-2,3,4,5-tetrahydro-1H-pyrido[4,3-b]indole hydrochloride 1.1(3)HCl, LCMS: m/z 290 [M+H]; cis-2-methyl-5-[2-(pyridin-3-yl)ethenyl]-2,3,4,5-tetrahydro-1H-pyrido[4,3-b]indole hydrochloride 1.1(4)HCl, LCMS: m/z 290 [M+H]; trans-2-methyl-5-[2-(pyridin-2-yl)ethenyl]-2,3,4,5-tetrahydro-1H-pyrido[4,3-b]indole hydrochloride 1.1(5)HCl, LCMS: m/z 290 [M+H]; cis-2-tert.butyl-5-[2-(pyridin-3-yl)ethenyl]-2,3,4,5-tetrahydro-1H-pyrido[4,3-b]indole hydrochloride 1.1(6)HCl, LCMS: m/z 332 [M+H]; cis-2-methyl-5-(2-phenylethenyl)-8-fluoro-2,3,4,5-tetrahydro-1H-pyrido[4,3-b]indole hydrochloride 1.1.1(1)HCl, LCMS: m/z 289 [M+H]; trans-2-methyl-5-(2-phenylethenyl)-8-fluoro-2,3,4,5-tetrahydro-1H-pyrido[4,3-b]indole hydrochloride 1.1.3(1)HCl, LC-MS: m/z 289 [M+H]; trans-2-methyl-5-[2-(pyridin-4-yl)ethenyl]-8-fluoro-2,3,4,5-tetrahydro-1H-pyrido[4,3-b]indole hydrochloride 1.1.3(2)HCl, LCMS: m/z 290 [M+H]; cis-2-methyl-5-[2-(pyridin-3-yl)ethenyl]-8-fluoro-2,3,4,5-tetrahydro-1H-pyrido[4,3-b]indole hydrochloride 1.1.1(2)HCl, LCMS: m/z 290 [M+H]; trans-2-methyl-5-[2-(pyridin-2-yl)ethenyl]-8-fluoro-2,3,4,5-tetrahydro-1H-pyrido[4,3-b]indole hydrochloride 1.1.3(3)HCl, LCMS: m/z 290 [M+H]; cis-2,8-dimethyl-5-(2-phenylethenyl)-2,3,4,5-tetrahydro-1H-pyrido[4,3-b]indole hydrochloride 1.1.1(3)HCl, LCMS: m/z 303 [M+H]; trans-2,8-dimethyl-5-[2-phenylethenyl]-2,3,4,5-tetrahydro-1H-pyrido[4,3-b]indole hydrochloride 1.1.3(4)HCl, LCMS: m/z 303 [M+H]; cis-2,8-dimethyl-5-[2-(pyridin-3-yl)ethenyl]-2,3,4,5-tetrahydro-1H-pyrido[4,3-b]indole hydrochloride 1.1.1(4)HCl, LCMS: m/z 304 [M+H]; trans-2,8-dimethyl-5-[2-(pyridin-4-yl)ethenyl]-2,3,4,5-tetrahydro-1H-pyrido[4,3-b]indole hydrochloride 1.1.3(5)HCl, LCMS: m/z 304 [M+H]; trans-2-methyl-5-[2-(4-fluorophenyl)ethenyl]-8-fluoro-2,3,4,5-tetrahydro-1H-pyrido[4,3-b]indole hydrochloride 1.1.3(6)HCl, LCMS: m/z 325 [M+H]; cis-2-methyl-5-[2-(3-fluorophenyl)ethenyl]-8-fluoro-2,3,4,5-tetrahydro-1H-pyrido[4,3-b]indole hydrochloride 1.1.1(6)HCl, LCMS: m/z 325 [M+H]; trans-2, 8-dimethyl-5-[2-(4-trifluoromethylphenyl)ethenyl]-2,3,4,5-tetrahydro-1H-pyrido[4,3-b]indole hydrochloride 1.1.3(7)HCl, LCMS: m/z 371 [M+H]; cis-2,8-dimethyl-5-[2-(3-trifluoromethylphenyl)ethenyl]-2,3,4,5-tetrahydro-1H-pyrido[4,3-b]indole hydrochloride 1.1.1(7)HCl, LCMS: m/z 371 [M+H]; trans-2-methyl-5-[2-(4-trifluoromethylphenyl)ethenyl]-8-fluoro-2,3,4,5-tetrahydro-1H-pyrido[4,3-b]indole hydrochloride 1.1.3(8)HCl, LCMS: m/z 375 [M+H]; cis-2-methyl-5-[2-(4-methoxyphenyl)ethenyl]-8-fluoro-2,3,4,5-tetrahydro-1H-pyrido[4,3-b]indole hydrochloride 1.1.1(8)HCl, LCMS: m/z 337 [M+H]; cis-2-methyl-5-[2-(4-dimethylaminophenyl)ethenyl]-8-fluoro-2,3,4,5-tetrahydro-1H-pyrido[4,3-b]indole hydrochloride 1.1.1(9)HCl, LCMS: m/z 350 [M+H]; trans-2,8-dimethyl-5-[2-(4-fluorophenyl)ethenyl]-2,3,4,5-tetrahydro-1H-pyrido[4,3-b]indole hydrochloride 1.1.3(9)HCl, LCMS: m/z 321 [M+H]; 2-methyl-5-(2-phenylethyl)-2,3,4,5-tetrahydro-1H-pyrido[4,3-b]indole hydrochloride 1.2(1)HCl, LCMS: m/z 291 [M+H]; 2-methyl-5-(2-phenylethyl)-2,3,4,5-tetrahydro-1H-pyrido[4,3-b]indole hydrobromide 1.2(1)HBr, LCMS: m/z 291 [M+H]; 2-methyl-5-[2-(pyridin-4-yl)ethyl]-2,3,4,5-tetrahydro-1H-pyrido[4,3-b]indole hydrochloride 1.2(2)HCl, LCMS: m/z 292 [M+H]; 2-methyl-5-[2-(pyridin-3-yl)ethyl]-2,3,4,5-tetrahydro-1H-pyrido[4,3-b]indole hydrochloride 1.2(3)HCl, LCMS: m/z 292 [M+H]; 2-methyl-5-[2-(pyridin-2-yl)ethyl]-2,3,4,5-tetrahydro-1H-pyrido[4,3-b]indole hydrochloride 1.2(4)HCl, LCMS: m/z 292 [M+H]; 2-methyl-5-[2-(6-methylpyridin-3-yl)ethyl]-2,3,4,5-tetrahydro-1H-pyrido[4,3-b]indole hydrochloride 1.2(6)HCl, LCMS: m/z 306 [M+H]; 2,8-dimethyl-5-(2-phenylethyl)-2,3,4,5-tetrahydro-1H-pyrido[4,3-b]indole hydrochloride 1.2.1(1)HCl, LCMS: m/z 305 [M+H]; 2,8-dimethyl-5-(2-phenylethyl)-2,3,4,5-tetrahydro-1H-pyrido[4,3-b]indole hydrobromide 1.2.1(1)HBr, LCMS: m/z 305 [M+H]; 2,8-dimethyl-5-[2-(pyridin-4-yl)ethyl]-2,3,4,5-tetrahydro-1H-pyrido[4,3-b]indole hydrochloride 1.2.1(2)HCl, LCMS: m/z 306 [M+H]; 2,8-dimethyl-5-[2-(pyridin-3-yl)ethyl]-2,3,4,5-tetrahydro-1H-pyrido[4,3-b]indole hydrochloride 1.2.1(3)HCl, LCMS: m/z 306 [M+H]; 2,8-dimethyl-5-[2-(pyridin-2-yl)ethyl]-2,3,4,5-tetrahydro-1H-pyrido[4,3-b]indole hydrochloride 1.2.1(4)HCl, LCMS: m/z 306 [M+H]; 2,8-dimethyl-5-[2-(6-methylpyridin-3-yl)ethyl]-2,3,4,5-tetrahydro-1H-pyrido[4,3-b]indole hydrochloride 1.2.1(5)HCl, LCMS: m/z 320 [M+H]; 2,8-dimethyl-5-[2-(pyrazin-2-yl)ethyl]-2,3,4,5-tetrahydro-1H-pyrido[4,3-b]indole hydrochloride 1.2.1(6)HCl, LCMS: m/z 305 [M+H]; 2-methyl-5-(2-phenylethyl)-8 fluoro-2,3,4,5-tetrahydro-1H-pyrido[4,3-b]indole hydrochloride 1.2.1(7)HCl, LCMS: m/z 309 [M+H]; 2-methyl-5-(2-phenylethyl)-8-fluoro-2,3,4,5-tetrahydro-1H-pyrido[4,3-b]indole hydrobromide 1.2.1(7)HBr, LCMS: m/z 309 [M+H]; 2-methyl-5-[2-(pyridin-4-yl)ethyl]-8-fluoro-2,3,4,5-tetrahydro-1H-pyrido[4,3-b]indole hydrochloride 1.2.1(8)HCl, LCMS: m/z 310 [M+H]; 2-methyl-5-[2-(pyridin-3-yl)ethyl]-8-fluoro-2,3,4,5-tetrahydro-1H-pyrido[4,3-b]indole hydrochloride 1.2.1(9)HCl, LCMS: m/z 310 [M+H]; 2-methyl-5-[2-(pyridin-2-yl)ethyl]-8-fluoro-2,3,4,5-tetrahydro-1H-pyrido[4,3-b]indole hydrochloride 1.2.1(10)HCl, LCMS: m/z 310 [M+H]; 2-methyl-5-[2-(6-methylpyridin-3-yl)ethyl]-8-fluoro-2,3,4,5-tetrahydro-1H-pyrido[4,3-b]indole hydrochloride 1.2.1(11)HCl, LCMS: m/z 324 [M+H]; 2-methyl-5-(2-phenylethyl)-8-trifluoromethyl-2,3,4,5-tetrahydro-1H-pyrido[4,3-b]indole hydrochloride 1.2.1(12)HCl, LCMS: m/z 309 [M+H] and others.

Example 5

The biological activity test of the substances of the general formula 1. The compounds of the general formula 1 were tested as potential antagonists of histamine receptor H1 and as regulators of calcium ions $Ca^{+2}$ cytosolic concentration in the cells by means of blocking the calcium canals regulated by the intracellular calcium depot. SK—N—SH cells (ATCC, USA) were grown in DMEM medium (Invitrogen, USA) containing 10% fetal calf serum (FBS) and Penicillin-Streptomycin antibiotics, in $CO_2$ incubator (5% $CO_2$) until the cell density reached $1*10^5$ cells/$cm^2$. The cells were removed from the surface of the flask with TrypLE Express reagent (Invitrogen, USA), collected by means of centrifugation and resuspended in Hybridoma Serum Free Medium (HSFM, Sigma, USA) at the concentration of $4*10^6$ cells/ml. To measure the intracellar concentration of calcium the cells were loaded with the calcium-sensitive fluorescent dye Fura 2 AM (Invitrogen, USA) by incubating the cells with the dye in the suspension for 30 minutes at room temperature. The cells were collected by centrifugation and resuspended in HSFM; then incubated in the suspension for 15 minutes, recollected by centrifugation, washed twice with HSFM and resuspended in HSFM at the concentration of $4*10^6$ cells/ml. The calcium streams in the cells were registered with Shimadzu-RF5301PC spectrofluorometer. The cells were diluted with an operating buffer (NaCl 0.145 M, KCl 0.0054 M, $NaH_2PO_4$ 0.001 M, $MgSO_4$ 0.0008 M, CaCl$_2$ 0.0018 M, HEPES 0.03 M, D-glucose 0.0112 M pH 7.4) to the concentration of 1*10$^5$ cells/ml in a measuring cell with a magnet stirrer, after that the registration of fluorescence was carried out in the mode of two-wavelength excitement (340 and 380 nm, respectively) with an emission wavelength of 510 nm (F1 and F2, respectively). In 20 seconds after the beginning of registration, 10 mM of histamine water solution was added (a final concentration is 10 μM). In another 30 seconds after the intracellular concentration of calcium had reached its maximum, DMSO solution of the tested compound was added, and registration was continued for additional 3 minutes. To estimate the biological activity of the compounds, their serial DMSO dilutions were prepared and the correlation between the influence of the compound on the histamine induced calcium stream and its concentration was determined. The transformation of fluorescent signal into calcium concentration was carried out by means of the equation built in the program Super Ion Probe (Shimadzu) software. For this purpose the maximum concentration of free calcium was determined by adding 0.1 mg/ml of digitonine (Sigma, USA) up to 0.1 mg/ml, while the zero calcium concentration—by adding of ethylene-diamin-tetraacetate (EDTA) up to 10 mM. Kinetic curves of lowering intracellular calcium concentration after the addition of the tested compound in the presence of histamine were calculated with a single-phase exponential model using the Prism 4 software (Graph-Pad Software, Inc.):

$[Ca] = [Ca]_{max} * \exp(-K*T) + [Ca]_{min}$ where T is the time after the tested compound was added, $[Ca]_{max}$ and $[Ca]_{min}$ are the maximum (the peak value after the addition of histamine) and the minimum (the equilibrium level the curve approached after the addition of the tested compound) concentrations of intracellular calcium, K is the constant of intracellular calcium concentration lowering calculated by minimization of least square deviations.

The calculated constants of calcium concentration lowering (K) were used to determine their dependence of the tested compound concentration (C); and on this dependence by means of the program Prism 4 values $EC_{50}$ (the concentration of the tested compound corresponding to half-maximum increasing of the constant of intracellular calcium concentration lowering) were determined using a four parameter equation to the $$K = K_{Bkg} + \frac{K_{max} C^N}{EC_{50}^N + C^N},$$

where $K_{Bkg}$ and $K_{max}$ are the constants of intracellular calcium concentration lowering without and in the presence of infinitely large concentration of the tested compound, respectively; N is Hill's coefficient. Below table 3 presents the values of $EC_{50}$ for some of the tested compounds of the general formula 1.

TABLE 3

Biological activity of antagonists of serotonine 5-HT$_6$ receptors and of homeostasis regulators of calcium ions of the general formula 1.

| N° comp. | Formula | EC$_{50}$, μM (Phase 1) | EC$_{50}$, μM (Phase 2) |
| --- | --- | --- | --- |
| 1.2.1(5)HCl Dimebon | 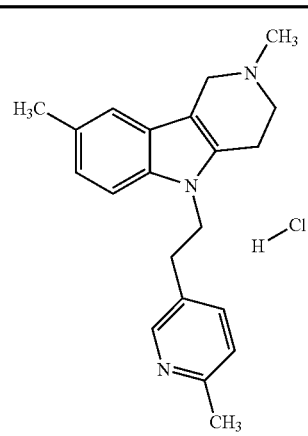 | 0.16 | 1.58 |
| 1.1(1) | 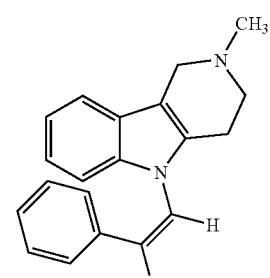 | 0.03 | 0.18 |

TABLE 3-continued
Biological activity of antagonists of serotonine 5-HT$_6$ receptors and of homeostasis regulators of calcium ions of the general formula 1.
| N° comp. | Formula | EC$_{50}$, μM (Phase 1) | EC$_{50}$, μM (Phase 2) |
| --- | --- | --- | --- |
| 1.1(2) | 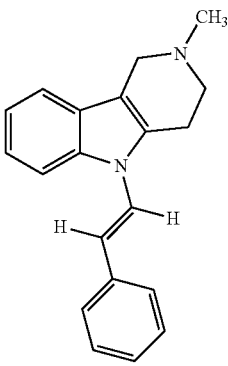 [SMILES: CN1CCc2c(c3ccccc3n2/C=C/c2ccccc2)C1] | 0.35 | 2.13 |
| 1.1(3) | 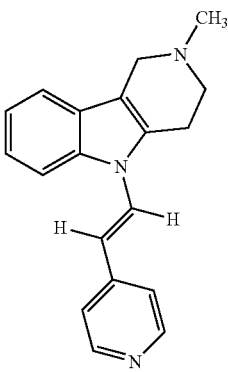 [SMILES: CN1CCc2c(c3ccccc3n2/C=C/c2ccncc2)C1] | >10 | >10 |
| 1.1(4) | 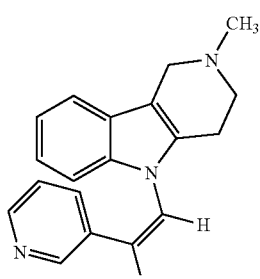 | >10 | >10 |
| 1.1(5) | 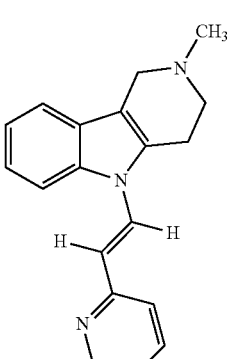 | >10 | >10 |

TABLE 3-continued

Biological activity of antagonists of serotonine 5-HT$_6$ receptors and of homeostasis regulators of calcium ions of the general formula 1.

| N° comp. | Formula | EC$_{50}$, μM (Phase 1) | EC$_{50}$, μM (Phase 2) |
|---|---|---|---|
| 1.1.1(1) | | 0.02 | 0.15 |
| 1.1.1(2) | | >10 | >10 |
| 1.1.1(3) | | 0.07 | 0.154 |
| 1.1.1(6) | | 0.035 | 0.19 |
| 1.2(2)HCl | | 0.12 | 0.5 |

TABLE 3-continued

Biological activity of antagonists of serotonine 5-HT$_6$ receptors and of homeostasis regulators of calcium ions of the general formula 1.

| N° comp. | Formula | EC$_{50}$, μM (Phase 1) | EC$_{50}$, μM (Phase 2) |
| --- | --- | --- | --- |
| 1.2(3)HCl | | 0.10 | 0.412 |
| 1.2(4)HCl | | 1.82 | 0.93 |
| 1.2.1(1)HCl | | 0.04 | 0.15 |
| 1.2.1(2)HCl | | 0.16 | 3.98 |

TABLE 3-continued
Biological activity of antagonists of serotonine 5-HT$_6$ receptors and of homeostasis regulators of calcium ions of the general formula 1.
| N° comp. | Formula | EC$_{50}$, μM (Phase 1) | EC$_{50}$, μM (Phase 2) |
|---|---|---|---|
| 1.2.1(3)HCl | 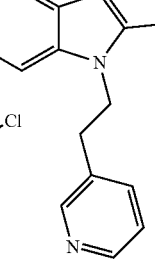 | 0.083 | 0.579 |
| 1.2.1(4)HCl | 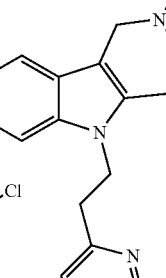 | 0.5 | 10 |
| 1.2.1(6) | 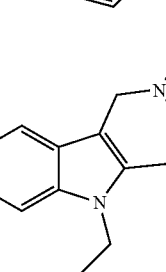 | 0.32 | 7.94 |
| 1.2.1(7)HCl | 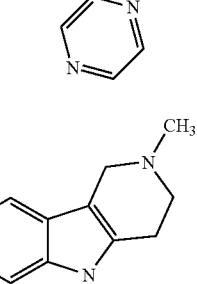 | 0.04 | 0.13 |

TABLE 3-continued

Biological activity of antagonists of serotonine 5-HT$_6$ receptors and of homeostasis regulators of calcium ions of the general formula 1.

| N° comp. | Formula | EC$_{50}$, μM (Phase 1) | EC$_{50}$, μM (Phase 2) |
|---|---|---|---|
| 1.2.1(8)HCl | | 0.12 | 0.47 |
| 1.2.1(9)HCl | | 0.09 | 0.297 |
| 1.2.1(10)HCl | | 0.94 | 0.61 |
| 1.2.1(11)HCl | | 0.113 | 0.73 |

TABLE 3-continued
Biological activity of antagonists of serotonine 5-HT$_6$ receptors and of homeostasis regulators of calcium ions of the general formula 1.
| N° comp. | Formula | EC$_{50}$, µM (Phase 1) | EC$_{50}$, µM (Phase 2) |
|---|---|---|---|
| 1.2.2(1)HCl | 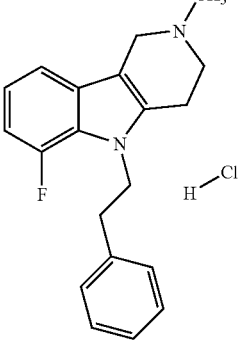 | 0.08 | 0.25 |
| 1.3(1) | 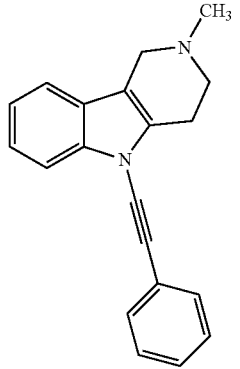 [SMILES: CN1CCc2c(c3ccccc3n2C#Cc2ccccc2)C1] | 9.56 | 10.1 |
| 1.3(3) | 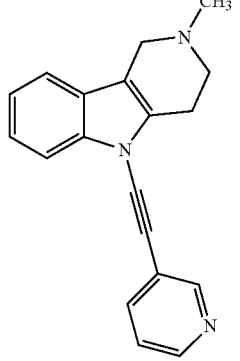 | >10 | >10 |
| 1.3.1(1) | 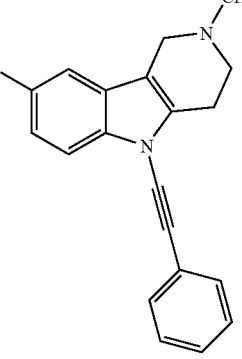 | >3 | |

TABLE 3-continued

Biological activity of antagonists of serotonine 5-HT$_6$ receptors and of homeostasis regulators of calcium ions of the general formula 1.

| N° comp. | Formula | EC$_{50}$, μM (Phase 1) | EC$_{50}$, μM (Phase 2) |
|---|---|---|---|
| 1.3.1(3) | [structure] | >10 | >10 |
| 1.3.1(5) | [structure] | >10 | >10 |
| 1.3.1(7) | [structure] | >10 | >10 |

As can be seen from table 3 compounds of the general formula 1 are effective blockers of the histamine receptor (Phase 1; the substances block calcium ions from entering the cells as a result of their antagonistic action on H1-receptors), and facilitate the discharge of intraplasmatic calcium (Phase 2), which evidences their anti-histamine (EC$_{50}$, μM (Phase 1)), neuro-protective and cognitive-stimulating effects (EC$_{50}$, μM ((Фаза 2)).

Example 6

The biological activity test of the compounds of the general formula 1. Compounds of the general formula 1 were tested for their ability to prevent the activation of 5-HT$_6$ receptors by serotonine. The cells HEK 293 (kidney cells of a human embryon) with an artificially expressed 5-HT$_6$ receptor, activation of which with serotonine results in intracellular cAMP increasing were used. The concentration of intracellular cAMP was determined using a LANCE cAMP reagent (PerkinElmer) by the method described by the manufacturer: [http://las.perkinelmer.com/content/Manuals/MAN_LANCEcAMP384KitUser.pdf].

The effectiveness of the compounds was estimated on the basis of their ability to reduce the concentration of intracellular cAMP induced by serotonine, FIG. 1. IC50 Values for some of the compounds of the general formula 1 are presented in table 4

TABLE 4

The ability of the compounds of the general formula 1 to prevent the activation of 5-HT$_6$ receptors by serotonine.

| N° comp. | Formula | IC$_{50}$, µM |
|---|---|---|
| 1.1(1) | | 7.2 |
| 1.1(2) | | 3.79 |
| 1.1(3) | | 26.7 |
| 1.1(4) | | >30 |

TABLE 4-continued

The ability of the compounds of the general formula 1 to prevent the activation of 5-HT$_6$ receptors by serotonine.

| N° comp. | Formula | IC$_{50}$, µM |
|---|---|---|
| 1.1(5) | | 45.9 |

TABLE 5

| N° comp. | Formula | IC$_{50}$, µM |
|---|---|---|
| 1.1.1(1) | | 14.6 |
| 1.1.1(2) | | >30 |
| 1.1.1(3) | | 0.172 |

TABLE 5-continued
| | | |
|---|---|---|
| 1.1.1(4) | 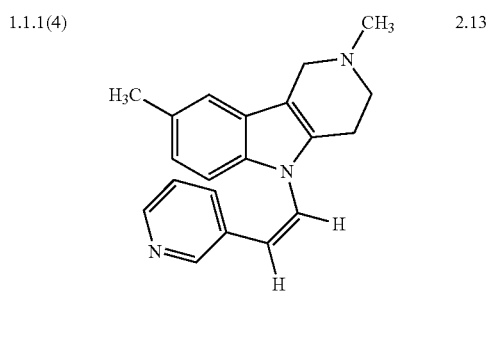 | 2.13 |
| 1.1.3(1) | 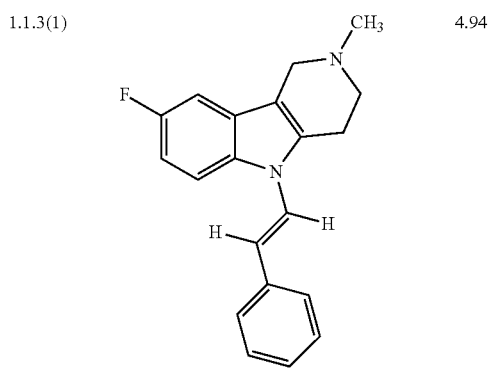 | 4.94 |
| 1.1.3(2) | 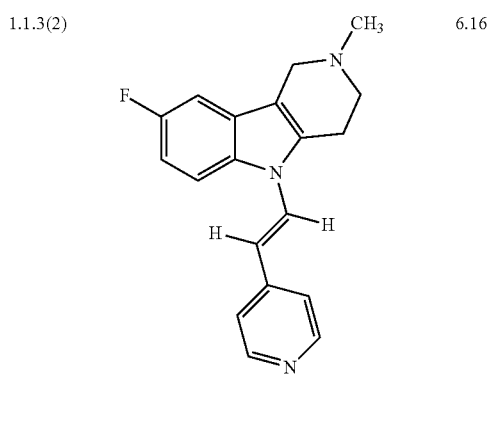 | 6.16 |
| 1.1.3(3) | 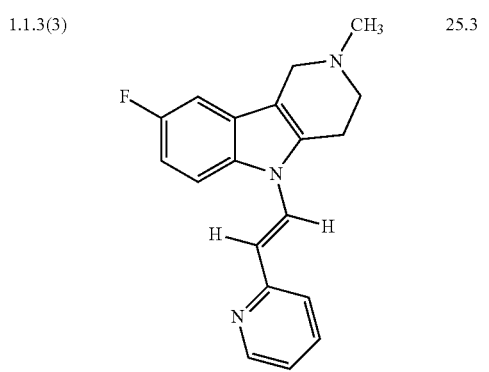 | 25.3 |
TABLE 5-continued
| | | |
|---|---|---|
| 1.1.3(4) | 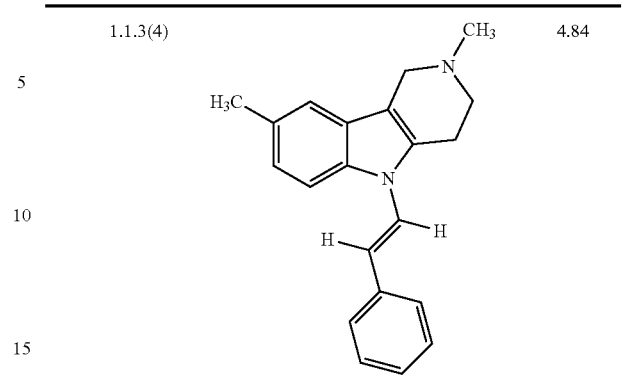 | 4.84 |
| 1.1.3(5) | 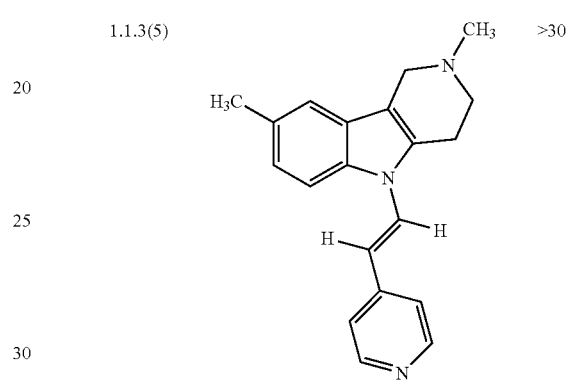 | >30 |
| 1.2(1)HCl | 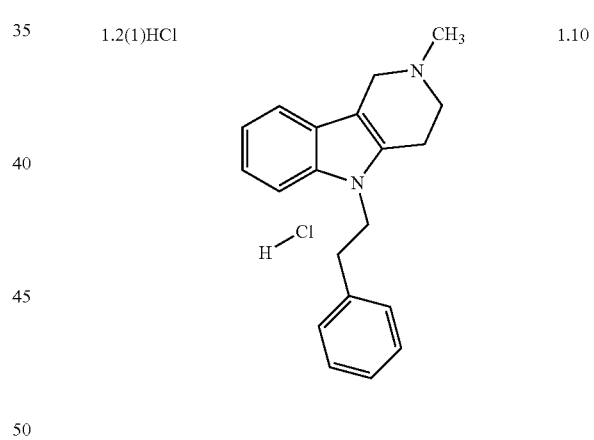 | 1.10 |
| 1.2.1(1)HCl | 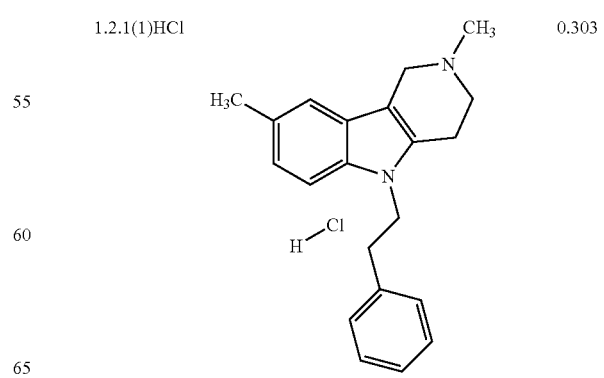 | 0.303 |

TABLE 5-continued
| 1.2.1(2)HCl | 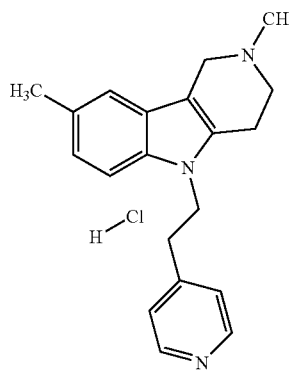 | 0.43 |
| 1.2.1(3)HCl | 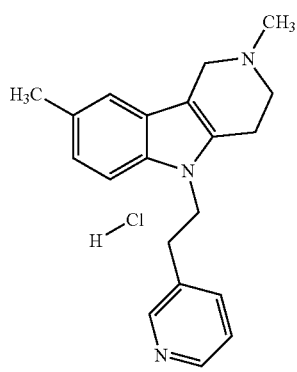 | 1.15 |
| 1.2.1(7)HCl | 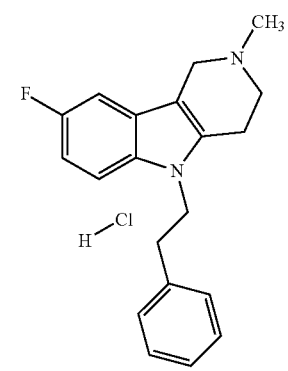 | 1.99 |
| 1.2.1(8)HCl | 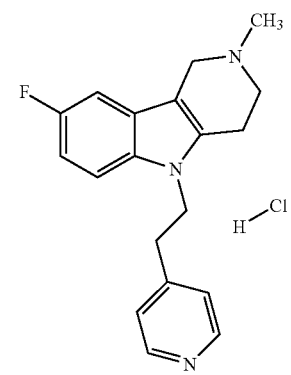 | 12.0 |
TABLE 5-continued
| 1.2.1(10)HCl | 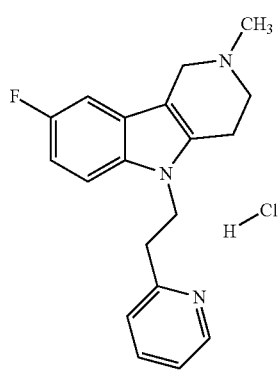 | 24.8 |
| 1.2.1(11)HCl | 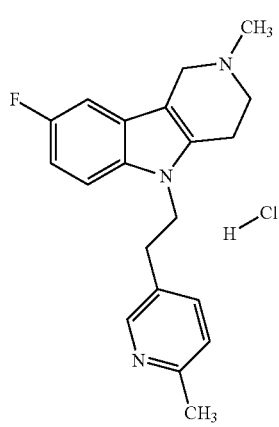 | 51.6 |
| 1.2.1(5)HCl Dimebon | 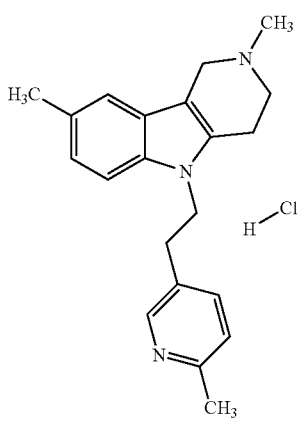 | 4.4 |
| 1.3(1) | 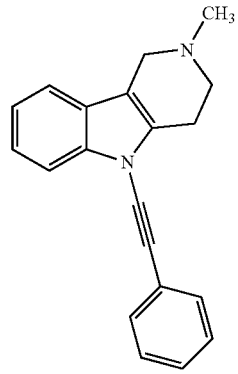 | 4.09 |

TABLE 5-continued

| | | |
|---|---|---|
| 1.3(3) | 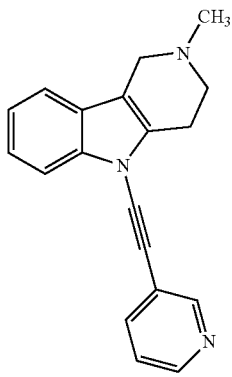 [SMILES: CN1CCc2c(c3ccccc3n2C#Cc2cccnc2)C1] | >30 |
| 1.3.1(1) | 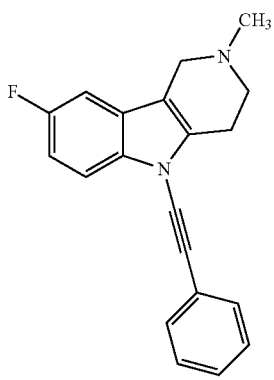 [SMILES: CN1CCc2c(c3cc(F)ccc3n2C#Cc2ccccc2)C1] | 5.77 |
| 1.3.1(3) | 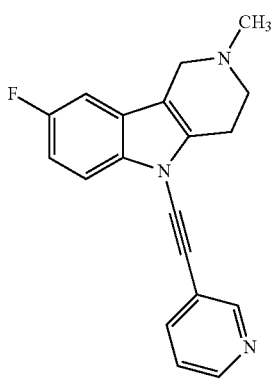 [SMILES: CN1CCc2c(c3cc(F)ccc3n2C#Cc2cccnc2)C1] | >30 |
| 1.3.1(5) | 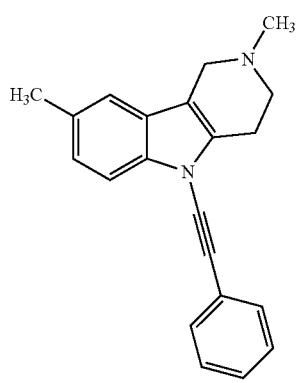 [SMILES: Cc1ccc2c(c1)c1c(n2C#Cc2ccccc2)CCN(C)C1] | 8.71 |
| 1.3.1(7) | 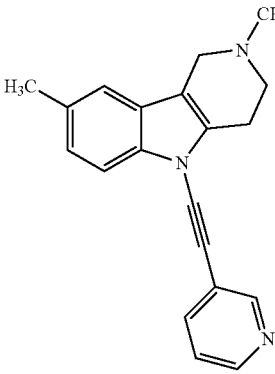 | >30 |

As can be seen from table 4 the compounds of the general formula 1 are effective antagonists of 5-HT6 serotonine receptors that proves the possibility of their use for treatment of Alzheimer's disease and other cognitive disorders.

Example 7

The nootropic action (memory enhancement disturbed by scopolamine) of antagonists of $5\text{-}HT_6$ receptors of the formulas 1.2.1(2)HCl, 1.2.1(4)HCl and 1.2.1(5)HCl in the test "Passive Avoidance of Mice in a Shuttle Chamber". A shuttle chamber (Ugo Basile, Italy) consisted of two sections was used. The walls of one section were opaque while the second section had a transparent cover. The sections were connected via a hole which could be shut with a vertical door. The floor was made of transverse metal bars on which DC current impulses could be fed. Experiments were carried out on aged male mice of line BALB/c weighing 20-24 grams.

On the first day of the experiment 30 minutes before training the mice were injected intraintestinally with physiological solution of scopolamine (0.3 mg/kg) or scopolamine in combination with antagonists of 5-HT6 receptors 1.2.1(2)HCl, 1.2.1(4)HCl or 1.2.1(5)HCl. Each group consisted of at least 8 animals. The animals were placed in the light section, and the latent period of the first entry into the dark chamber was registered. Then the vertical door was closed and the animal was punished by 0.6 mA DC current for 3 seconds. After that the animal was carried back to its living cell. In 22-24 hours the same animal was placed in the light section of the shuttle chamber once again and the latent period before its entry into the dark section, the total time of its stay in the light section and the number of entries into the dark section were registered. Each observation lasted for 5 minutes.

The experiment was carried out during the day time in an isolated laboratory using white noise at a level of about 70 decibel above the human hearing threshold.

Scopolamine causes the disturbance of training (memory loss) which results in an increased latent period of the first entry into the dark section, a longer stay in the light section and a decreased number of entries into the dark section.

The fact that $5\text{-}HT_6$ receptor antagonists can improve the learning ability that has been disturbed by scopolamine is regarded as evidence for their nootropic effect.

The obtained results (see FIGS. 2-4) confirm that 1.2.1 (2)HCl, 1.2.1(4)HCl and 1.2.1(5)HCl antagonists of $5\text{-}HT_6$ receptors exhibit a nootropic action which is the most prominent for 1.2.1(2)HCl and 1.2.1(4)HCl antagonists.

Example 8

The nootropic action (improvement of memory disturbed by scopolamine) of antagonists of 5-HT$_6$ receptors of the formulas 1.2.1(1)HCl and 1.2.1(5)HCl in the test "Passive Avoidance of Mice in a Shuttle Chamber". The experiment was carried out in the same way as in example 7. On the first day 30 minutes before training the mice were injected intra-intestinally with a physiological solution of scopolamine (0.3 mg/kg) or MK-801(0.1 mg/kg). Simultaneously the mice in the control groups were injected intra-intestinally with a physiological solution of scopolamine in addition with antagonist of 5-HT$_6$ receptors 1.2.1(1)HCl, 1.2.1(5)HCl, and scopolamine with control antagonists of 5-HT$_6$ receptors SB-742457 (1 mg/kg, 15 minutes before training) and PRX-07034 (10 mg/kg, 30 minutes before training).

The results of the experiment (FIGS. 5-10) show that anatagonists of 5-HT$_6$ receptors 1.2.1(1)HCl and 1.2.1(5)HCl exhibit a nootropic action which is the most prominent for 1.2.1(1)HCl and 1.2.1(5)HCl antagonists. Besides the test demonstrated the highest activity of 1.2.1(1)HCl antagonist, while the control antagonist SB-742457 proved to be inactive.

Example 9

The nootropic action (improvement of memory disturbed by scopolamine) of antagonists of 5-HT$_6$ receptors of the formulas 1.2.1(1)HCl and 1.2.1(5)HCl in the test "Training Mice in the Morris Water labyrinth". A circular pool of 100 cm diameter and of 30 cm sides was used. It was filled with water at 20-22° C. A circular ceramic platform of 14 cm height was placed in the pool. The behavior of the animals was registered using an automated computer video system in addition with software package of movement analyzer Anymaze (Stoelting Co., US). The experiments were carried out on aged male mice of BALB/c line weighing 20-24 grams. Before the experiments mice fit for learning were selected. This was done by placing the platform 1 cm above the water level and putting an animal on the platform for 20 seconds. Then the mouse was put in the water on the opposite side of the pool and allowed to find the platform and climb onto it for 60 seconds, where it was left for additional 20 seconds. After that the mouse was repeatedly immersed in the water on the opposite side of the pool and allowed to search for the platform. If it failed in finding the platform within 60 seconds the experimentator helped it to find the platform and climb onto it. If the mice couldn't find the platform itself in two consecutive attempts it was excluded from the experiment.

During the next two days the platform was placed 0.5 centimeters lower the water level. Every day the mice were given four attempts for finding the platform within 60 seconds. The time interval between the attempts was 20 seconds, during which the mice stayed on the platform. Every day before the first attempt the mice was placed on the platform for 20 seconds. The time needed for finding and climbing the platform was registered. The animals were sunk in water in two different places on the side of the pool opposite to the platform. On each day of the experiment 35-40 minutes before training the mice were injected intra-intestinally with scopolamine (0.6 mg/kg), scopolamine together with tacrine (3 mg/kg), scopolamine together with antagonist of 5-HT$_6$ receptors 1.2.1(5)HCl (0.1 mg/kg) or scopolamine together with antagonist of 5-HT$_6$ receptor 1.2.1(1)HCl (1 mg/kg).

The animals of the control group were injected with physiological solution. At least 8 animals were used in each group.

On the third day the platform was removed and each animal was placed in the pool once for a period of 60 seconds. The time each mouse spent in the area where the platform had been located during the previous days was registered. This time served as a measure of the effectiveness of the training carried out during the previous two days.

The animals of the control group were trained successfully over the first 2 days; that was confirmed by the prolonged periods of time they spent on the third day in the area where the platform had been. The administration of 0.6 mg/kg of scopolamine totally disrupted training under the above conditions, that was confirmed by the relatively short period of time the mice had been injected with scopolamine only spent in the area where the platform had been. Antagonists of 5-HT$_6$ receptors 1.2.1(1)HCl and 1.2.1(5)HCl and 3 mg/kg of tacrine caused a statistically significant improvement of mice's training (FIG. 11-12).

Example 10

The nootropic action (improvement of memory disturbed by scopolamine) of antagonists of 5-HT$_6$ receptors of the formulas 1.2.1(1)HCl and 1.2.1(5)HCl in the test "Recognition of New Objects by Mice Under Scopolamine and MK-801". The experiments were carried out in a closed cross shaped labyrinth which consisted of 4 peripheral sections connected with the central chamber via a 7×7 cm hole. The labyrinth was made of black plastic and its sections were of 14×14×14 cm size. The top cover of the labyrinth was transparent.

A mouse was placed in the central section of the labyrinth and allowed to investigate the environment. A mouse was considered to have entered a section once all of its four paws were inside the chamber. A test was considered to be completed when the mouse had moved 12 times between the sections, having made a total of 13 visits. The floor of the labyrinth was cleaned after each animal.

With each mouse the test was carried out twice with 1 hour interval.

During the first test, each section of the labyrinth contained a circular plastic cup of 3 cm height and 7 cm diameter. During the second test the cover in each of the two opposing sections was replaced by a conical glass bulb of 7 cm height and 4 cm across the bottom. The time that the mice spent in each section of the labyrinth was registered and the index of new object recognition was calculated as the ratio of the time spent in the sections with the bulbs to the time spent in all sections of the labyrinth. If no preference is given to the sections with new objects the index is 0.5.

When new objects appear the mice spend more time in the section containing them that results in an increased recognition index. Scopolamine (1 mg/kg) and MK-801 (0.2 mg/kg) disturbed learning (memory) that leads to lowering of the recognition index. The ability of antagonists of 5-HT$_6$ receptors 1.2.1(1)HCl and 1.2.1(5)HCl to improve new object recognition is regarded as evidence of their nootropic action.

The results obtained show the ability of memantine, SB-742457, 1.2.1(1)HCl and 1.2.1(5)HCl to nootropic action, the level of which is the most prominent for antagonist of 5-HT$_6$ receptor 1.2.1(1)HCl (FIG. 13-14).

Example 11

The antidepressant action of antagonist of 5-HT$_6$ receptor 1.2.1(1)HCl in the test "Mice Behavior in the Test of Porsolt Forced Swimming". A plastic vessel filled at 20-22° C. with water to height of 18 cm was used. The experiments were carried out on aged male mice of BALB/c line weighing 20-24 grams. Each animal was placed in water and duration time of motionless hanging in water was registered during 15 minutes—so named the behavior of "despair" which is the measure of a depressively-like condition. The last five minutes of the test are used in analysis. Automated computerized detection of motion with videosystem and Any-maze program were used in the experiment. This index is reduced when antidepressants are administered (FIGS. 15-16).

Example 12

The antidepressant action of antagonist of $5\text{-HT}_6$ receptor 1.2.1(1)HCl in the test "Hanging Mice by the Tail". The experiments were carried out on aged male mice of BALB/c line weighing 20-24 grams. In the test the mice were hung by the tail using a sticky tape on the holder over a horizontal surface at a height of 40 cm and during 3 minutes the total duration time of episodes of complete immobility was recorded. Automated computerized detection of motion with videosystem and Any-maze program were used in the experiment. Complete immobility is reduced when antidepressants are administered (FIGS. 17-18).

Example 13

The tranquilizing action of antagonists of $5\text{-HT}_6$ receptors 1.2.1(1)HCl and 1.2.1(5)HCl in the test "Mice Behavior an Elevated Cross Shaped Labyrinth". The length of each section in the labyrinth is 30 cm, the width is 5 cm, the height of the walls is 15 cm. Two opposite sections are closed by transparent walls on the sides and on the butt ends, the other two sections are lit and opened. A mouse was placed in the center of the labyrinth and for the next five minutes the number of entries the open and closed sections and the time spent in each type of section was registered. These data were used to calculate the indexes of preference for the open sections as the ratio of the number of the open corridor entries, as well as the total time spent there to the whole number of entries to all sections and the total time spent there. The animals usually avoid the open sections (the preference index is between 0.2 and 0.3). Compounds with tranquilizing action increase this index up to 0.5-0.6 or even more and reduce the number of defecations without altering the overall motion activity of the mice (the total number of their entries the sections).

The results obtained show (FIG. 19-21) that Buspiron, 1.2.1(1)HCl and 1.2.1(5)HCl exhibit a tranquilizing action, which is the most prominent for compound 1.2.1(1)HCl.

Example 14

Preparation of a medicine in the form of tablets. Mix together 1600 mg of starch, 1600 mg of grained lactose, 400 mg of talcum and 1000 mg of 2,8-dimethyl-5-[2-(pyridin-4-yl)ethyl]-2,3,4,5-tetrahydro-1H-pyrido[4,3-b]indole hydrochloride 1.2.1(2) and press together in a brick. Prepared brick was crushed to granules and riddled through sieves, gathering granules of 14-16 mesh size. The obtained granules were pelletised in the tablets of suitable form 560 mg by weight each. According to the invention pharmaceutical compositions in the form of tablets comprising as a biological active ingredient other substituted 2,3,4,5-tetrahydro-1H-pyrido[4,3-b]indoles of the general formula 1 could be prepared in a similar way.

Example 15

Preparation of a medicine in the form of capsules. Carefully mix 2,8-dimethyl-5-[2-(pyridin-4-yl)ethyl]-2,3,4,5-tetrahydro-1H-pyrido[4,3-b]indole hydrochloride 1.2.1(2) with a powder of lactose in ratio 2:1. The prepared powdery mixture was packed on 300 mg into gelatinous capsules of suitable size.

Example 16

Preparation of a medicine in the form of compositions for intramuscular, intraperitoneal or hypodermic injections. Mix 500 mg of 2,8-dimethyl-5-[2-(pyridin-4-yl)ethyl]-2,3,4,5-tetrahydro-1H-pyrido[4,3-b]indole hydrochloride 1.2.1(2) with 300 mg of chlorobutanole, 2 ml of propylene glycol and 100 ml of water for injections. The prepared solution was filtered and placed in 1 ml ampoules which were sealed up and sterilized in an autoclave.

INDUSTRIAL APPLICABILITY

The invention could be used in medicine, veterinary, biochemistry.

The invention claimed is:

1. A method of antagonizing a $5\text{-HT}_6$ serotonin receptor, comprising administering to a cell a compound of formula 1.2, or a pharmaceutically acceptable salt thereof,

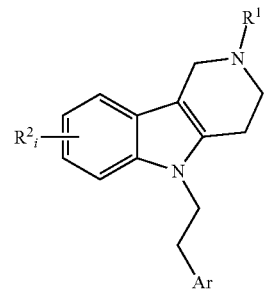

1.2 wherein: $R^1$ is a $C_1\text{-}C_5$ alkyl;
$R^2_i$ is independently hydrogen, halogen, a $C_1\text{-}C_3$ alkyl, $CF_3$, $OCF_3$ or $OCH_3$;
i is 1, 2, 3 or 4;
Ar is an unsubstituted phenyl or a substituted phenyl substituted with halogen, $C_1\text{-}C_6$ alkyl, $C_1\text{-}C_6$ alkoxy, substituted amino group or trifluoromethyl; or Ar is a substituted or unsubstituted 6-membered aromatic heterocycle with one or two nitrogen atoms in the heterocycle.

2. The method of claim 1, wherein the compound is:

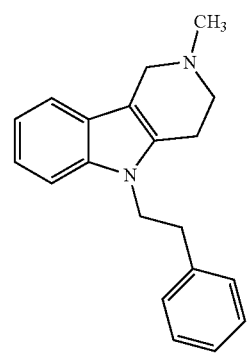

1.2(1)

1.2(2)
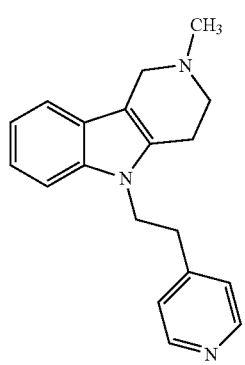
1.2(3)
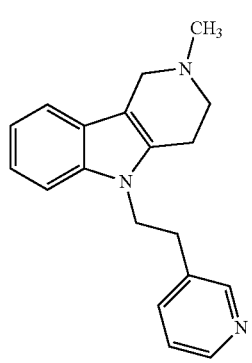
1.2(4)
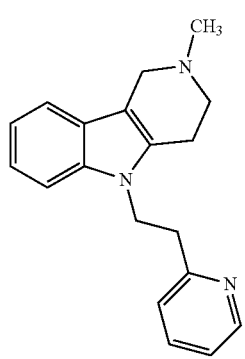
1.2(5)
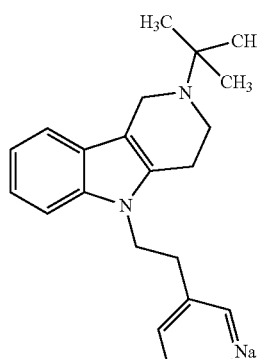
1.2(6)
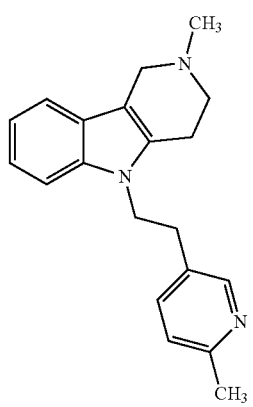
1.2.1(1)
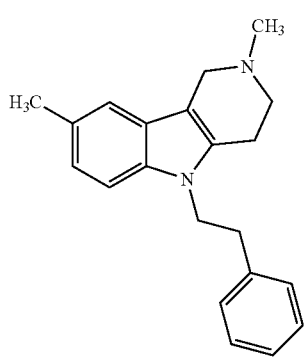
1.2.1(2)
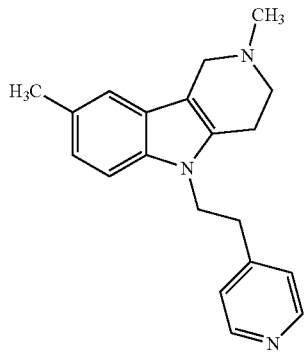
1.2.1(3)
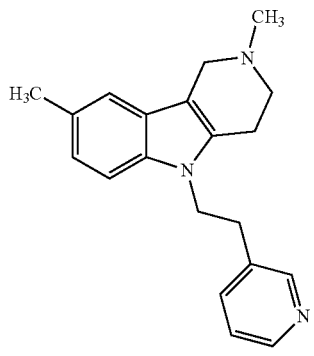

1.2.1(4)
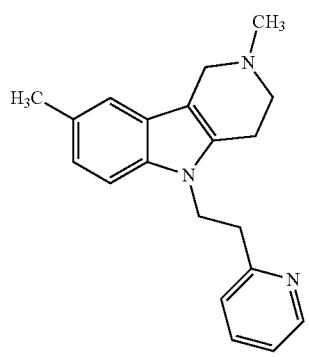
1.2.1(5)
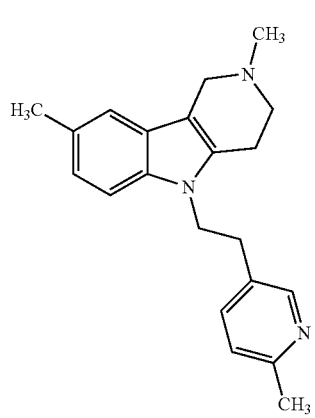
1.2.1(6)
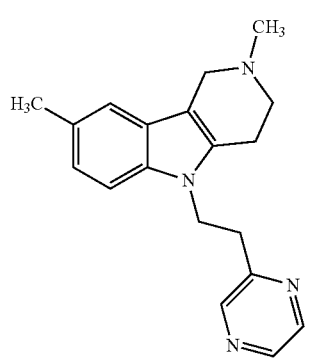
1.2.1(7)
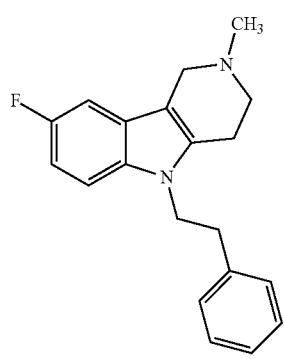
1.2.1(8)
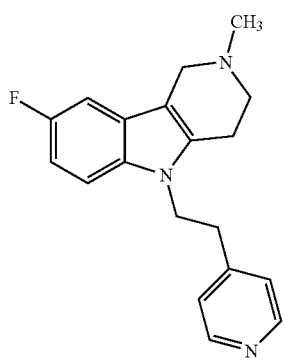
1.2.1(9)
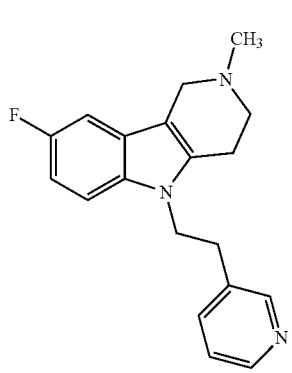
1.2.1(10)
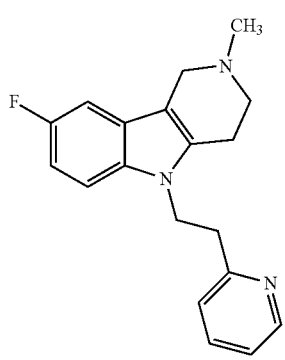
1.2.1(11)
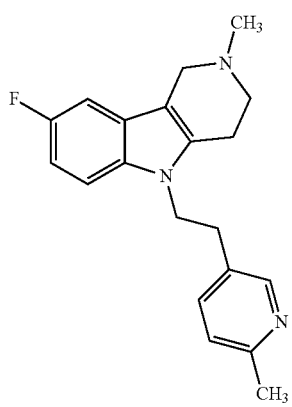

1.2.1(12)

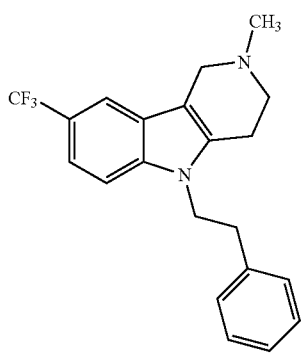

1.2.1(13)

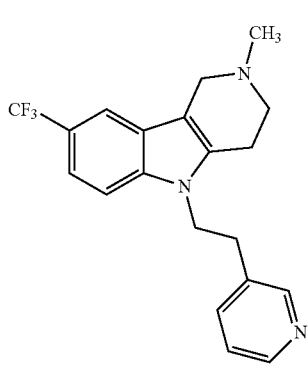

1.2.2(1)

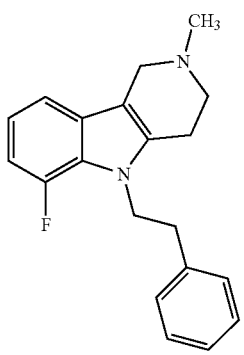

1.2.2(2)

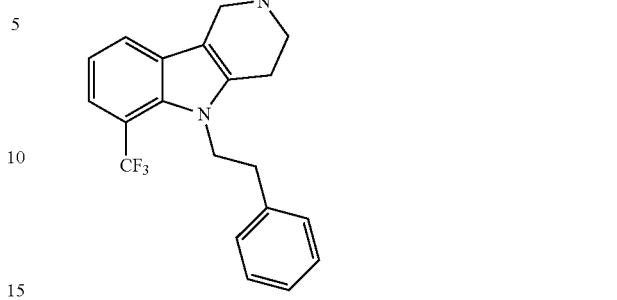

1.2.2(3)

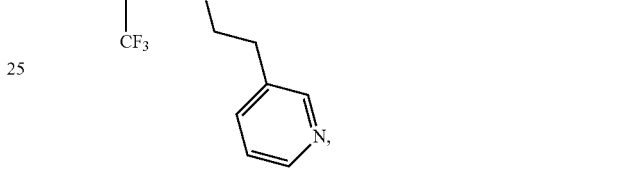

or a pharmaceutically acceptable salt thereof.

3. A pharmaceutical composition, for treatment of cognitive disorders and neurodegenerative diseases, pathogenesis of which is associated with serotonin 5-HT6 receptors comprising at least one compound of formula 1.2 in an effective amount, excluding hydrochloride of 2,8-dimethyl-5-[2-(6-methyl-pyridin-3-yl)ethyl]-2,3,4,5-tetrahydro-1H-pyrido[4,3-b]indole of formula 1.2.1(5).HCl.

4. A pharmaceutical composition according to claim 3 and at least one pharmaceutically acceptable carrier, inert, excipient or solvent.

5. The pharmaceutical composition according to claim 3 in the form of a tablet, capsule, or injection.

6. A method for treating a cognitive disorder and neurodegenerative disease in a subject in need thereof comprising administering an effective dose to the subject of the compound of formula 1.2 in an effective amount.

7. The method according to claim 6 for treating a psychotic disorder, schizophrenia, depression, an anxiety disorder, hypoxia-ischemia, a convulsive state, cerebral damage, lathyrism, amyotrophic lateral sclerosis, or premature senility in a subject in need thereof comprising administering an effective dose to the subject of the compound of formula 1.2 in an effective amount.

8. The method for treating Alzheimer's disease, Huntington's disease, in a subject in need thereof comprising administering an effective dose to the subject of the compound of formula 1.2 in an effective amount, excluding hydrochloride of 2,8-dimethyl-5-[2-(6-methyl-pyridin-3-yl)ethyl]-2,3,4,5-tetrahydro-1H-pyrido[4,3-b] indole of formula 1.2.1(5).HCl.

* * * * *